(12) United States Patent
Williams et al.

(10) Patent No.: US 7,629,308 B2
(45) Date of Patent: Dec. 8, 2009

(54) METHODS RELATING TO MUSCLE SELECTIVE CALCINEURIN INTERACTING PROTEIN (MCIP)

(75) Inventors: R. Sanders Williams, Dallas, TX (US); Beverly Rothermel, Bedford, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1874 days.

(21) Appl. No.: 09/782,953

(22) Filed: Feb. 13, 2001

(65) Prior Publication Data

US 2002/0150953 A1    Oct. 17, 2002

Related U.S. Application Data

(60) Provisional application No. 60/216,601, filed on Jul. 7, 2000.

(51) Int. Cl.
    *A61K 35/34*      (2006.01)
    *A31K 38/00*      (2006.01)
(52) U.S. Cl. .......................... 514/2; 530/350; 530/841; 424/278.1; 424/548
(58) Field of Classification Search ...................... 514/2, 514/278.1; 536/23.2, 23.1; 435/69.1, 320.1, 435/455; 436/94; 800/14; 530/350
See application file for complete search history.

(56) References Cited

U.S. PATENT DOCUMENTS

| | | | | |
|---|---|---|---|---|
| 4,330,557 | A * | 5/1982 | Cavazza | 514/547 |
| 5,651,980 | A * | 7/1997 | Lanza et al. | 424/424 |
| 5,869,318 | A * | 2/1999 | Palleja et al. | 435/252.3 |
| 5,958,404 | A * | 9/1999 | Selawry | 424/93.7 |
| 6,673,604 | B1 * | 1/2004 | Edge | 435/347 |

FOREIGN PATENT DOCUMENTS

| | | | |
|---|---|---|---|
| WO | WO 99 19473 A | 4/1999 |
| WO | WO 99 50410 A | 10/1999 |
| WO | WO 00 09667 A | 2/2000 |
| WO | WO 02/04491 | 1/2002 |

OTHER PUBLICATIONS

Rothermel, B. et al. (2000) A protein encoded within the Down syndrome critical region is enriched in striated muscles and inhibits calcineurin signaling. J. Biol. Chem. vol. 275, pp. 8719-8725.*
Fuentes, J. J. et al. (2000) DSCR1, overexpressed in Down syndrome, is an inhibitor of calcineurin-mediated signaling pathways. Human Mol. Genet. vol. 9, pp. 1681-1690.*
Miyazaki, T. et al. (1996) Molecular cloning of a novel thyroid hormone-responsive gene, ZAKI-4, in human skin fibroblasts. J. Biol. Chem. vol. 271, pp. 14567-1471.*
Chin E. R. et al. (1998) A calcineurin-dependent transcriptional pathway controls skeletal muscle fiber type. Genes Dev. vol. 12, pp. 2499-2509.*
Sussman, M. A. et al. (1998) Prevention of cardiac hypertrophy in mice by calcineurin inhibition. Science. vol. 281, pp. 1690-1693.*
Yang J. et al. (2000) Independent signals control expression of the calcineurin inhibitory proteins MCIP1 and MCIP2 in striated muscles. Circ Res. vol. 87, pp. e61-e68.*
Berchtold, M. W. et al. (2000) Calcium ion in skeletal muscle: its crucial role for muscle function, plasticity, and disease. Physiol Rev. vol. 80, pp. 1215-1265. Review.*
Dunn, S. E. et al. (2002) Calcineurin and skeletal muscle growth. Nat. Cell Biol. vol. 4, p. E46-47.*
Colao, A. et al. (1999) Effects of 1-year treatment with octreotide on cardiac performance in patients with acromegaly. J Clin Endocrinol Metab. vol. 84, pp. 17-23.*
Vega, R. B. et al. (2003) Dual roles of modulatory calcineurin-interacting protein 1 in cardiac hypertrophy. Proc Natl Acad Sci U S A. vol. 100, pp. 669-674.*
Ohkawa et al. (2003) Calcineurin-mediated pathway involved in the differentiated phenotype of smooth muscle cells.Biochem. Biophys. Res. Commun. vol. 301, No. 1, pp. 78-83.*
Kessen et al. (1999) Ca(2+)/calmodulin-independent activation of calcineurin from Dictyostelium by unsaturated long chain fatty acids. J. Biol. Chem. vol. 274, No. 53, pp. 37821-37826.*
Hilioti et al. (2003) GSK-3 kinases enhance calcineurin signaling by phosphorylation of RCNs, Genes Dev., vol. 18, No. 1, pp. 35-47.*
Beals et al., "Nuclear localization of NF-Atc by a calcineurin-dependent, cyclosporin-sensetive intramolecular interaction," *Genes Dev.*, 11:824-834, 1997.
Chin et al., "A calcineurin-dependent transcriptional pathway controls skeletal muscle fiber type," *Genes Dev.*, 12:2499-2509, 1998.
Crabtree, "Generic signals and specific outcomes: signaling through $Ca^{2+}$, calcineurin, and NF-AT," *Cell*, 96:611-614, 1999.
Ding et al., "Pressure overload induces severe hypertrophy in mice treated with cyclosporine, an inhibitor of calcineurin," *Circ Res.*, 84:729-734, 1999.
Dunn et al., "Calcineurin is required for skeletal muscle hypertrophy," *J Biol Chem.*, 274:21908-21912, 1999.
Eto et al., "Calcineurin is activated in rat hearts with physiological left ventricular hypertrophy induced by voluntary exercise training," *Circulation*, 101:2134-2137, 2000.
Friddle et al., "Expression profiling reveals distinct sets of genes altered during induction and regression of cardiac hypertrophy," *Proc. Natl. Acad. Sci. USA*, 97:6745-6750, 2000.
Fuentes et al., "Genomic organization, alternative splicing, and expression patterns of the DSCR1 (Down syndrome candidate region 1) gene," *Genomics*, 44:358-361, 1997.
Fuentes et al., "A new human gene from the Down syndrome critical region encodes a proline-rich protein highly expressed in fetal brain and heart," Abstract, *Hum. Mol. Genet.*, 4:1935-1944, 1995.

(Continued)

*Primary Examiner*—Kathleen Kerr Bragdon
*Assistant Examiner*—Samuel W Liu
(74) *Attorney, Agent, or Firm*—Fulbright & Jaworski

(57) ABSTRACT

The present invention relates to the polypeptides known as muscle calcineurin interacting proteins (MCIPs). These molecules binding to calcineurin and, in so doing, modulate its functions, which includes phosphate removal as part of a pathway coupling $Ca^{2+}$ to cellular responses in muscle. MCIPs form a physical complex with the catalytic subunit of calcineurin, and increased levels of MCIPs correspond to a reduced ability of calcineurin to stimulate transcription of certain target genes. Methods to exploit these observation are provided and include screening for modulators of MCIP expression and binding to calcineurin, methods of diagnosis of MCIP defects, and methods for treating cardiomyopathies, including cardiac hypertrophy.

4 Claims, 12 Drawing Sheets

OTHER PUBLICATIONS

Graef et al., "L-type calcium channels and GSK-3 regulate the activity of NF-Atc4 in hippocampal neurons," *Nature*, 401:703-8, 1999.

Grayson et al., "Synergistic interactions between heterologous upstream activation elements and specific TATA sequences in a muscle-specific promoter," *Mol-Cell Biol.*, 15(4):1870-1878, 1995.

Grayson et al., "Collaborative interactions between MEF-2 and Sp1 in muscle-specific gene regulation," *J. Cell. Biochem.*, 70:366-375, 1998.

Ho et al., "NFATc3, a lymphoid-specific NFATc family member that is calcium-regulated and exhibits distinct DNA binding specificity," *J. Biol. Chem.*, 270(34):19898-19907, 1995.

Ho et al., "Activation protein 1-dependent transctiptional activation of interleukin 2 gene by Ca2+/calmodulin kinase type IV/Gr," Abstract, *J. Exp. Med.*, 184:101-112, 1996.

Hoey et al., "Isolation of two new membes of the NF-AT gene family and functional characterization of the NF-AT proteins," Abstract, *Immunity*, 2:461-472, 1995.

Kashishian et al., "AKAP79 inhibits calcineurin through a site distinct from the immunophilin-binding region," *J. Biol. Chem.*, 273:27412-27419, 1998.

Kingsbury and Cunningham, "A conserved family of calcineurin regulators," *Genes Dev.*, 14(13):1595-1604, 2000.

Klauck et al., "Coordination of three signaling enzymes by AKAP79, a mammalian scaffold protein," *Science*, 271:1589-1592, 1996.

Klee et al., "Regulation of the calmodulin-stimulated protein phosphatase, calcineurin," *J. Biol. Chem.*, 273(22):13367-13370, 1998.

Lai et al., "Cain, a novel physiologic protein inhibitor of calcineurin," *J. Biol. Chem.*, 273(29):18325-18331, 1998.

Liu et al., "Cyclosporin A-sensetive induction of the Epstein-Barr virus lytic switch is mediated via a novel pathway involving a MEF2 family member," *EMBO J.*, 16:143-153, 1997.

Loh et al., "Calcineurin binds the transcription factor NFAT1 and reversibly regulates its activity," *J. Biol. Chem.*, 271:10884-10891, 1996.

Mann et al., "Construction of a retrovirus packaging mutant and its use to produce helper-free defective retrovirus", *Cell*, 33:153-159, 1983.

Mao and Wiedmann, "Calcineurin enhances MEF2 DNA binding activity in calcium-dependent survival of cerebellar granule neurons," *J. Biol. Chem.*, 274:31102-31107, 1999.

Mao et al., "Neuronal activity-dependent cell survival mediated by transcription factor MEF2," *Science*, 286:785-790, 1999.

Mesaeli et al., "Calreticulin is essential for cardiac development," *J. Cell Biol.*, 144:857-868, 1999.

Miyazaki et al., "Molecular cloning of a novel thyroid hormone-responsive gene, ZAKI-4, in human skin fibroblasts," *J Biol Chem.*, 271:14567-14571, 1996.

Molkentin et al., "A calcineurin-dependent transcriptional pathway for cardiac hypertrophy," *Cell*, 93:215-228, 1998.

Musaro et al., "IGF-1 induces skeletal myocyte hypertrophy through calcineurin in association with GATA-2 and NF-ATc1," *Nature*, 400:581-585, 1999.

Naya et al., "Stimulation of slow skeletal muscle fiber gene expression by calcineurin in vivo," *J. Biol. Chem.*, 275:4545-4548, 2000.

O'Keefe et al., "FK-506- and CsA-sensetive activation of the interleukin-2 promoter by calcineurin," *Nature*, 357:692-694, 1992.

Rothermel et al., "A protein encoded within the Down syndrome critical region is enriched in striated muscles and inhibits calcineurin signaling," *J Biol Chem.*, 275:8719-8725, 2000.

Rothermel et al., "Myocyte-enriched calcineurin-interacting protein, MCIP1, inhibits cardiac hypertrophy in vivo," *PNAS*, 98(6):3328-3333, 2001.

Schena et al., "Parallel human genome analysis: microarray-based expression monitoring of 1000 genes," *Proc Natl Acad Sci USA*, 93:10614-10619, 1996.

Semsarian et al, "Skeletal muscle hypertrophy is mediated by a Ca2+-dependent calcineurin signalling pathway," *Nature*, 400:576-581, 1999.

Shibasaki et al., "Role of kinases and the phosphatase calcineurin in the nuclear shuttling of transcription factor NF-AT4," *Nature*, 382:370-373, 1996.

Sigal et al., "Cyclophilin involved in the immunosuppressive and nephrotoxic mechanism of action of cyclosporin A?," *J. Exp. Med.*, 173:619-628, 1991.

Sun et al., "Cabin 1, a negative regulator for calcineurin signaling in T lymphocytes," *Immunity*, 8:703-711, 1998.

Sussman et al., "Prevention of cardiac hypertrophy in mice by calcineurin inhibition," *Science*, 281:1690-1693, 1998.

Wang et al.,"$Ca^{2+}$-induced apoptosis through calcineurin dephosphorylation of BAD," *Science*, 284:339-343, 1999.

Yang et al., "Independent signals control expression of the calcineurin inhibitory proteins MCIP1 and MCIP2 in striated muscles," *Circ. Res.*, 87:e61-e68, 2000.

Youn et al., "Apoptosis of T cells mediated by $Ca^{2+}$-induced release of the transcription factor MEF2," *Science*, 286:790-793, 1999.

Zhang et al., "Failure of calcineurin inhibitors to prevent pressure-overload left ventricular hypertrophy in rats," *Circ Res.*, 84:722-728, 1999.

Zhuo et al., "A selective role of calcineurin A$\alpha$ in synaptic depotentiation in hippocampus," *Proc. Nat'l Acad. Sci. USA*, 96:4650-4655, 1999.

Fuentes et al., "DSCR1, overexpressed in Down syndrome, is an inhibitor of calcerium-mediated signalling pathways," *Human Mol. Gen.*, 9:1681-1690, 2000.

Strippoli et al., "A new gene family including DSCR1 (Down syndrome candidate region 1) and ZAKI-4: Characterization from yeast to human and identification of DSCR1-like 2, a novel human member (DSCR1LR)," *Genomics*, 64:252-263, 2000.

Database Swissport 'Online!,"Calcipressin 1 (Down syndrome critical region protein 1) (Myocyte-enriched calcineurin interacting protein 1) (MCIP1) (Adapt78)," Database Accession No. P53805, XP002212253, Oct. 1, 1996.

Database EMBL 'Online! "Homo sapiens down syndrome candidate region 1 (DSCR1) gene, alternative exon 1, complete cds," Database Accession No. U85267, XP002212252, Jun. 21, 1997.

Database EMBL 'Online!, "Homo sapiens down syndrome candidate region 1 (DSCR1) gene, alternative exon 1, complete cds," Database Accesiion No. U85265, XP002212254, Jun. 21, 1997.

Database EMBL 'Online!,"Homo sapiens genomic DNA, chromosome 21q22.1, D21S226-AML region, clone B2344F14-f50E8, segment 5/9." Database Accession No. AP000169, XP002212286, May 14, 1999.

Database EMBL 'Online!, "Mus musculus myocyte-enriched calcineurin interactin protein 1 splice variant 4 mRNA, complete cds," Database Accesssion No. AF237790, XP002212249, Apr. 12, 2000.

Database EMBL 'Online!, "Mus musculus calcineurin inhibitor mRNA, complete cds, alternatively spliced," Database Accession No. AF263239, XP002212250, May 30, 2000.

Database EMBL 'Online!, "Mus musculus calcineurin inhibitor mRNA, complete cds, alternatively spliced," Database Accession No. AF263240, XP002212251, May 30, 2000.

Database EMBL 'Online!, "Mus musculus myocyte-enriched calcineurin interactin protein 1 splice variant 1 mRNA, complete cds," Database Accession No. AF237789, XP002212255, Apr. 12, 2000.

Database EMBL 'Online!, "Mus musculus Down syndrome candidate region 1 (DSCR1) mRNA, complete cds," Database Accession No. AF260717, XP002212256, May 17, 2000.

European Office Action, issued in Application No. 01 952 568. 2—2401, dated Apr. 17, 2009.

Rothermel et al., "The role of modulatory calcineurin-interacting proteins in calcineurin signaling." *Trends in Cardiovascular Medicine*, 13:15-21, 2003.

* cited by examiner

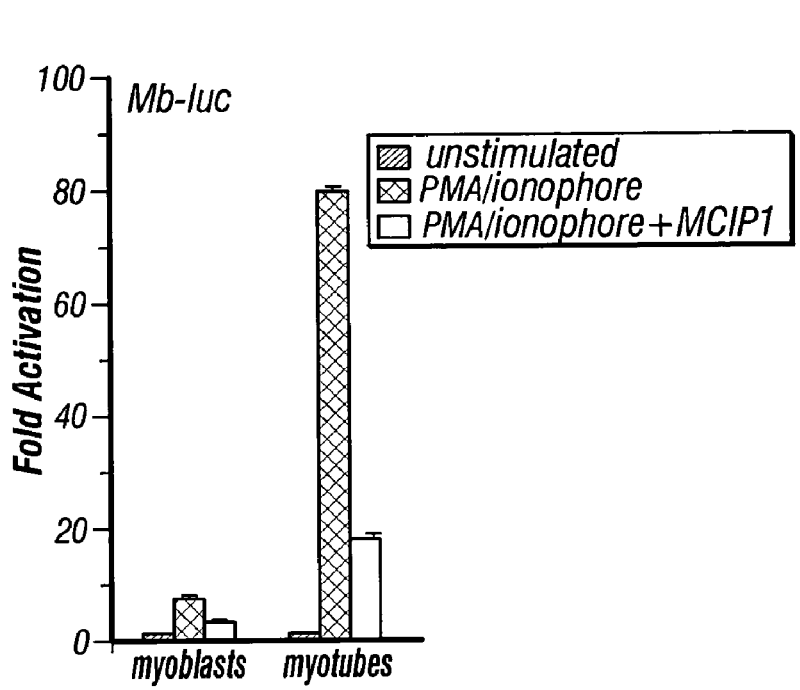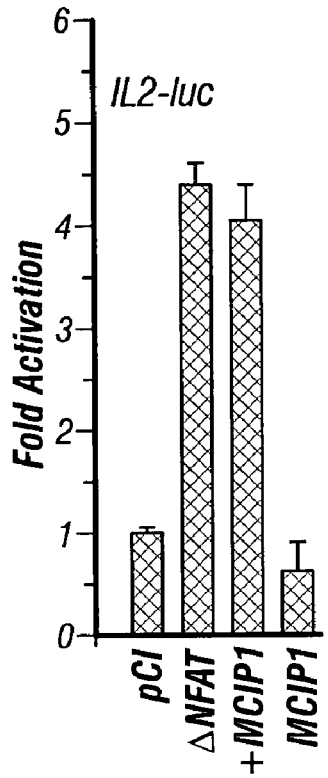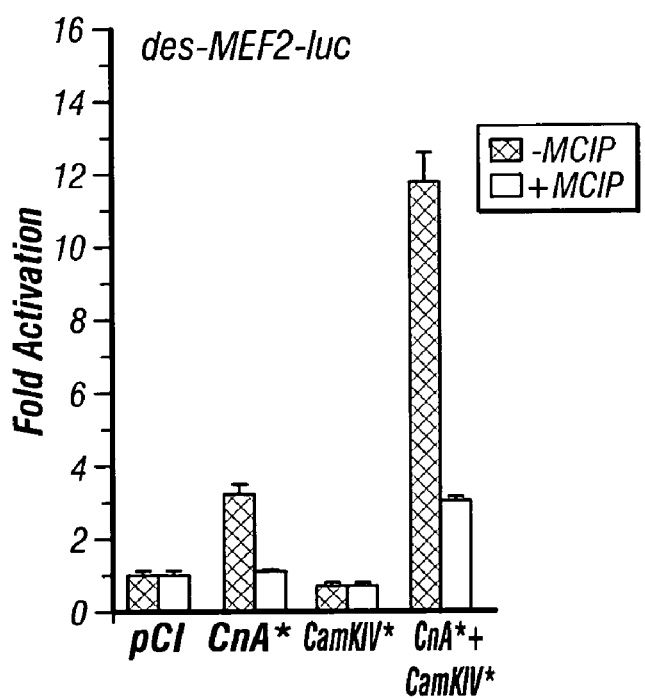
FIG. 2A
FIG. 2B
FIG. 2C

| Rank | Fold | Gene | Genbank ID |
|---|---|---|---|
| *hypertrophic α-MHC-CnA\* vs. wild-type* | | | |
| 1 | 8.1 | Calcineurin-A | AA245461 |
| 2 | 4.0 | ANF precursor type B | AA030805 |
| 3 | 3.3 | ANF precursor type A | W14325 |
| 4 | 3.1 | sk mus LIM protein (FHL1) | AA047966 |
| 5 | 3.0 | OSF-2 | W81878 |
| →6 | 2.7 | MCIP-1 | AA200984 |
| 7 | 2.7 | EST (mouse) | AA110791 |
| 8 | 2.3 | MCPSF (Mouse cleavage and polyadenylation factor) | AA221269 |
| *failing α-MHC-CnA\* vs. hypertophic α-MHC-CnA\** | | | |
| 1 | 3.3 | Procollagen XV | W83331 |
| 2 | 2.9 | OSF-2 | W81878 |
| 3 | 2.8 | EST (mouse) | AA124355 |
| 4 | 2.7 | Alpha-crystallin | AA231358 |
| →5 | 2.5 | MCIP-1 | AA200984 |
| 6 | 2.2 | Procollagen III | W89883 |
| 7 | 2.1 | p53BP2 | AA467287 |
| 8 | 2.1 | Calcineurin-A | AA245461 |

METHODS RELATING TO MUSCLE SELECTIVE CALCINEURIN INTERACTING PROTEIN (MCIP)

The present application claims priority from U.S. Provisional Patent Application Ser. No. 60/216,601 filed Jul. 7, 2000.

This invention was made with government support under grant number R01-AR40849 awarded by the National Institutes of Health. The government has certain rights in the invention.

BACKGROUND OF THE INVENTION

1. Field of the Invention

The present invention relates generally to the fields of developmental biology and molecular biology. More particularly, it concerns the proteins, classified here as MCIPs, identified as regulating calcineurin function.

2. Description of Related Art

Calcineurin is a serine/threonine protein phosphatase that plays a pivotal role in developmental and homeostatic regulation of a wide variety of cell types (Klee et al., 1998; Crabteee, 1999). The interaction of calcineurin with transcription factors of the NFAT family following activation of the T cell receptor in leukocytes provides the best characterized example of how calcineurin regulates gene expression (Rao et al., 1997). Changes in intracellular calcium promote binding of $Ca^{2+}$/calmodulin to the catalytic subunit of calcineurin (CnA), thereby displacing an autoinhibitory region and allowing access of protein substrates to the catalytic domain. Dephosphorylation of NFAT by activated calcineurin promotes its translocation from the cytoplasm to the nucleus, where NFAT binds DNA cooperatively with an AP1 heterodimer to activate transcription of genes encoding cytokines such as IL-2. This basic model of NFAT activation has been shown to transduce Ca2+ signals via calcineurin in many cell types and to control transcription of diverse sets of target genes unique to each cellular environment (Timmerman et al, 1996). In each case, NFAT acts cooperatively with other transcription factors that include proteins of the AP1 (Rao et al., 1997), cMAF (Ho et al., 1996), GATA (Mesaeli et al., 1999; Molkentin et al., 1998; Musaro et al., 1999), or MEF2 (Chin et al., 1998; Liu et al., 1997; Mao et al., 1999; Mao and Wiedmann, 1999) families. In addition to T cell activation, cellular responses controlled by calcineurin signaling include synaptic plasticity (Mao et al., 1999; Graef et al., 1999; Zhuo et al., 1999) and apoptosis (Wang et al., 1999; Youn et al., 1999).

Recent studies of calcineurin signaling in striated myocytes of heart and skeletal muscle have expanded the scope of important physiological and pathological events controlled by this ubiquitously expressed protein. Forced expression of a constitutively active form of calcineurin in hearts of transgenic mice promotes cardiac hypertrophy that progresses to dilated cardiomyopathy, heart failure, and death, in a manner that recapitulates features of human disease (Molkentin et al., 1998). Moreover, hypertrophy and heart failure in these animals, and in certain other animal models of cardiomyopathy, are prevented by administration of the calcineurin antagonist drugs cyclosporin A or FK-506 (Sussman et al., 1998). In skeletal muscles, calcineurin signaling is implicated both in hypertrophic growth stimulated by insulin-like growth factor-1 (Musaro et al., 1999; Semsarian et al., 1999), and in the control of specialized programs of gene expression that establish distinctive myofiber subtypes (Chin et al., 1998; Dunn et al., 1999). These observations have stimulated interest in the therapeutic potential of modifying calcineurin activity selectively in muscle cells while avoiding unwanted consequences of altered calcineurin signaling in other cell types (Sigal et al., 1991).

The activity of calcineurin in mammalian cells can be modulated by interactions with other proteins. These include not only immunophilins that are the targets of the immunosuppresant drugs cyclosporin A and FK-506, but two unrelated proteins (AKAP79 and cabin-1/cain) that were identified recently. AKAP79 binds calcineurin in conjunction with protein kinase C and protein kinase A, serving as a scaffold for assembly of a large hetero-oligomeric signaling complex (Kashishian et al., 1998). Cabin-1/cain binds both calcineurin and the transcription factor MEF2 (Sun et al., 1998; Lai et al., 1998). As a consequence of cabin-1 overexpression, calcineurin activity is inhibited and MEF2 is sequestered in an inactive state. Another calcineurin-binding protein is Rex1p (YKL159c) of *Saccharomyces cerevisiae*. A preliminary report noted that this small 24 kDa protein inhibits calcineurin signaling when overexpressed in yeast (Kingsbury and Cunningham, 1998).

The existence of calcineurin regulating proteins gives rise to potential therapeutic interventions targeting these molecules. Identifying new, more suitable candidates having the ability to modulate calcineurin function in cardiac tissue is an important goal of current research efforts.

SUMMARY OF THE INVENTION

Therefore, according to the present invention, there is provided a method of screening for a modulator of MCIP binding to calcineurin comprising (a) providing an MCIP and calcineurin; (b) admixing the MCIP and calcineurin in the presence of a candidate modulator; (c) measuring MCIP/calcineurin binding; and (d) comparing the binding in step (c) with the binding of MCIP and calcineurin in the absence of said candidate modulator, whereby a difference in the binding of MCIP and calcineurin in the presence of said candidate modulator, as compared to binding in the absence of said candidate modulator, identifies said candidate modulator as a modulator of MCIP binding to calcineurin. In one embodiment, the MCIP and calcineurin are part of a cell free system. In another embodiment, the MCIP and calcineurin are located within an intact cell, for example, in a animal. Useful cells include myocytes, cardiomyocytes, H9C2 cells, neonatal cardiomyocytes, 3T3 cells, 293 cells and myotube cells.

The modulator may increase or decrease MCIP binding to calcineurin. Either or both MCIP and calcineurin may be labeled, for example, one with a quenchable label and the other with a quenching agent. Alternatively, where both MCIP and calcineurin are labeled, the labels are not detectable unless brought into proximity of each other. The cell may be engineered to overexpress MCIP, calcineurin or both. The method may comprises immunologic detection of MCIP, calcineurin or both. The MCIP may be MCIP1, MCIP2 or MCIP3.

In another aspect of the invention, there is provided a method of screening for a modulator of MCIP dephosphorylation comprising (a) providing a phosphorylated MCIP and calcineurin; (b) admixing the MCIP and calcineurin in the presence of a candidate modulator; (c) assessing MCIP phosphorylation; and (d) comparing the phosphorylation state of MCIP in step (c) with the phosphorylation state of MCIP in the absence of the candidate modulator, whereby a difference in MCIP phosphorylation in the presence of said candidate modulator, as compared to phosphorylation in the absence of said candidate modulator, identifies said candidate modulator as a modulator of MCIP phosphorylation.

The modulator may increase or decrease MCIP dephosphorylation by calcineurin. The intact cell may express a protein selected from the group consisting of PKC, CaMK, GSK3 and MAPK, and isoforms and variants thereof. The intact cell also may be engineered to overexpress one or more of MCIP and calcineurin. The assessing may comprise detection of radiolabeled phosphorus, detection of changes of electrophoretic mobility, or detection of binding by antibodies that discriminate between phosphorylation states. The MCIP may be MCIP1, e.g., with phosphorylation at Ser108 assessed, MCIP2 or MCIP3.

In yet another aspect of the invention, there is provided a method of screening for a modulator of MCIP expression comprising (a) providing a cell expressing an MCIP and calcineurin; (b) administering to said cell a candidate modulator; (c) measuring MCIP expression; and (d) comparing the expression in step (c) with the expression of MCIP in the absence of the candidate modulator, whereby a difference in MCIP expression in the presence of said candidate modulator, as compared to expression in the absence of said candidate modulator, identifies said candidate modulator as a modulator of MCIP expression.

The cell may be a myocyte or a cardiomyocyte. The measuring of MCIP expression may comprise assessing transcription by Northern analysis, assessing transcription by quantitative RT-PCR, ELISA, or Western blot. The MCIP may be selected from the group consisting of MCIP1, MCIP2 and MCIP3. The modulator may increase or decrease MCIP expression.

In still yet another aspect of the invention, there is provided a method of screening for a modulator of muscle cell growth comprising (a) providing a cell expressing an MCIP and calcineurin; (b) administering to said cell a candidate modulator; (c) measuring transcription of a target molecule that is indicative of muscle cell growth; and (d) comparing the transcription in step (c) with the transcription of the target molecule in the absence of the candidate modulator, whereby a difference in muscle cell growth in the presence of said candidate modulator, as compared to growth in the absence of said candidate modulator, identifies said candidate modulator as a modulator of muscle cell growth.

The cell may be a myocyte or a cardiomyocyte. The method may further comprise measuring transcription of the target molecule in the absence of the candidate inhibitor, for example, MEF2. The MCIP may be MCIP1, MCIP2 or MCIP3. The modulator may increase or decrease muscle cell growth. The cell may be located in a mammal.

In each of the preceding screening embodiments, there also is provided similar methods for the production of a modulator, comprising each of the aforementioned screening steps, followed by the additional step of producing the modulator so identified.

In another aspect of the invention, there is provided a method of modulating muscle cell growth comprising (a) providing a modulator of MCIP binding to calcineurin; and (b) administering said modulator to a muscle cell, whereby administration of said modulator results in modulation of muscle cell growth.

In another aspect of the invention, there is provided a method of modulating muscle cell growth comprising (a) providing a modulator of MCIP dephosphorylation by calcineurin; and (b) administering said modulator to a muscle cell, whereby administration of said modulator results in modulation of muscle cell growth.

In another aspect of the invention, there is provided a method of modulating muscle cell growth comprising (a) providing a modulator of MCIP expression; and (b) administering said modulator to a muscle cell, whereby administration of said modulator results in modulation of muscle cell growth.

The muscle cell may be located in a mammal. The modulator may be an agonist of muscle cell growth, for example, a small molecule, or an expression cassette comprising a DNA segment encoding an MCIP operably linked to a promoter active in said muscle cell. The promoter may be myosin light chain-2 promoter, alpha actin promoter, troponin 1 promoter, $Na^+/Ca^{2+}$ exchanger promoter, dystrophin promoter, creatine kinase promoter, alpha7 integrin promoter, brain natriuretic peptide promoter, alpha B-crystallin/small heat shock protein promoter, atrial natriuretic factor promoter or alpha myosin heavy chain. The expression cassette may further comprise a polyadenylation signal or an origin of replication. The expression construct may be a viral expression construct, for example, an adenoviral construct, a retroviral construct, an adeno-associated viral construct, a herpesviral construct, a vaccinia viral construct, a polyoma viral construct, or a Sindbis viral vector. The method further comprises administering to said mammal a pharmaceutical agent used to treat cardiac disease.

In a further aspect of the invention, there is provided an isolated and purified DNA segment encoding a MCIP1 promoter, such as that isolatable from the sequence of SEQ ID NO:11. Also provided is an expression cassette comprising 50-1000 base pairs of SEQ ID NO:11 operably linked to a DNA segment encoding a polypeptide other than MCIP1. The polypeptide may be screenable marker protein. A host cell comprising an expression cassette comprising 50-1000 base pairs of SEQ ID NO:11 operably linked to a DNA segment encoding a polypeptide other than MCIP1 also is provided.

In yet a further aspect of the invention, there is provided a method for screening for modulators of MCIP1 expression comprising (a) providing a cell transformed with an expression cassette comprising 50-1000 base pairs of SEQ ID NO:11 operably linked to a DNA segment encoding a screenable marker protein; (b) administering to said cell a candidate modulator; (c) measuring expression of said marker protein; and (d) comparing the expression of said marker protein in step (c) with the expression of said marker protein in the absence of said candidate modulator, whereby a difference in marker protein expression in the presence of said candidate modulator, as compared to expression in the absence of said candidate modulator, identifies said candidate modulator as a modulator of MCIP expression.

In still yet a further aspect of the invention, there is provided a method of treating cardiac hypertrophy or heart failure comprising administering to a subject suffering from cardiac hypertrophy or heart failure an agent that promotes MCIP binding to calcineurin. The method may further comprise treating said subject with an ionotrope, a beta blocker, an antiarrhythmic, a diuretic, a vasodilator, a hormone antagonist, an endothelin antagonist, an angiotensin type 2 antagonist or a cytokine inhibitor/blocker. The agent may be a phosphatase that acts on Ser 108 of MCIP, an inducer of a phosphatase that acts on Ser108 of MCIP, a MCIP analogue that binds calcineurin but lacks a removable phosphate at Ser108, or an expression cassette comprising an MCIP coding sequence under the control of a promoter active in cardiac tissue. The agent may be administered intravenously or orally, may be in a delayed release formulation. The agent may be a small molecule modulator.

In another aspect of the invention, there is provided an isolated and purified nucleic acid encoding an MCIP 1 polypeptide that lacks sequences encoded by Exons 1, 2 and 3. The nucleic acid may further comprise a promoter, for example, a muscle specific promoter, for example, myosin light chain-2 promoter, alpha actin promoter, troponin 1 promoter, $Na^+/Ca^{2+}$ exchanger promoter, dystrophin promoter, creatine kinase promoter, alpha7 integrin promoter, brain natriuretic peptide promoter, or alpha B-crystallin/small heat shock protein promoter, alpha myosin heavy chain promoter, or atrial natriuretic factor promoter. Alternatively, the promoter may be the native MCIP1 promoter. The nucleic acid may further comprise an origin of replication. The nucleic acid may a non-viral vector or a viral vector.

In still another aspect of the invention, there is provided an isolated and purified nucleic acid encoding an MCIP1 polypeptide lacking residues 1-80 of SEQ ID NO:2, optionally, comprising a promoter. In a related aspect of the invention, there is provided an isolated and purified MCIP 1 polypeptide lacking amino acid residues corresponding to Exons 1, 2 and 3. In another related aspect of the invention, there is provided an isolated and purified MCIP1 polypeptide lacking residues 1-80 of SEQ ID NO:2.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: myoblasts harvested 24 h after transfection or myotubes harvested 72 h after transfection. FIG. 1B: myotubes harvested 72 h after cotransfection with a luciferase reporter under the control of three copies of a Gal4p binding site (UASg-TATA-luc), and plasmids encoding Gal4-VP16 fusion protein or MCIP1.

FIGS. 2A-C—The inhibitory effect of MCIP1 is on calcineurin itself rather than on downstream effectors of calcineurin signaling. FIG. 2A: MCIP1 inhibits the transcriptional response to activation of endogenous calcineurin. C2C12 cells were transfected with the Mb-luc reporter plus or minus MCIP1. The transfected cells were stimulated with 1 µM ionomycin and 10 ng/ml PMA 4.5 h prior to harvesting. Data were calculated as described in FIGS. 1A-B. FIG. 2B: MCIP1 fails to inhibit the transcriptional response to a constitutively active (calcineurin-independent) form of NFATc. C2C12 cells were cotransfected with the IL-2-luc reporter and plasmids encoding MCIP or a constitutively active form of NFATc (NFAT) as indicated. Cells were harvested 24 h after transfection. FIG. 2C: MCIP1 inhibits calcineurin-dependent stimulation of the transactivating function of MEF2. C2C12 cells were transfected with a luciferase reporter containing three copies of a high affinity MEF2 binding site from the desmin gene (des-MEF2-luc). The reporter was stimulated by cotransfection with plasmids encoding constitutively active forms of calcineurin (CnA*), calmodulin-dependent protein kinase IV (CaMKIV) and MCIP1 as indicated. Cells were harvested 48 h after transfection. All results are corrected for variations in transfection efficiency by normalization to expression of a co-transfected pCMV-lacZ plasmid.

FIG. 4A: schematic depiction of functional domains of calcineurin A, as defined by previous studies (1), and including the catalytic domain, binding sites for calcineurin B (B) and calmodulin (M), and the carboxyl-terminal autoinhibitory domain (I). Truncated forms of calcineurin A are identified by their termination at specific amino acid (aa) residues corresponding to positions within the full-length protein, and by their binding to MCIP1. FIG. 4B: calcineurin A proteins were translated in rabbit reticulocyte lysates and labeled with [$^{35}$S]methionine. Recombinant GST-MCIP1 was purified from bacteria and coupled to glutathione-agarose beads. Binding of truncated forms of calcineurin A to GST-MCIP1 was compared with GST alone, and to 25% of the total pool of metabolically labeled protein included in the binding reaction (Input). Luciferase failed to interact with GST-MCIP1, serving as a negative control (data not shown). Proteins were separated by SDS-PAGE and visualized by autoradiography.

FIG. 5A: schematic depiction of MCIP1 illustrating amino acid sequence motifs conserved with yeast Rex1p (24) and mammalian NFAT (3) proteins, and including an SP repeat region and calcineurin docking motif (P). Truncated forms of MCIP1 are identified by their termination at specific amino acid (aa) residues corresponding to positions within the full-length protein, and by their binding to calcineurin A. FIG. 5B: calcineurin A (amino acids 1-398) was translated in rabbit reticulocyte lysates and labeled with [$^{35}$S]methionine. Recombinant full-length or truncated forms of GST-MCIP1 were purified from bacteria and coupled to glutathione-agarose beads. Binding of calcineurin A to each variant of GST-MCIP1 was compared with GST alone, and to 25% of the total pool of metabolically labeled protein included in the binding reaction (input). Proteins were separated by SDS-PAGE and visualized by autoradiography.

FIG. 6A: Northern blots demonstrating expression of a 2.2-kB pair MCIP1 transcript, and two MCIP2 transcripts of 3.4 and 1.4 kB pairs in tissues of adult mice. Both genes are more highly expressed in heart and soleus skeletal muscles than in other tissues, with the exception that MCIP2 transcripts are also abundant in brain. Each lane was loaded with 20 µg of total RNA, and equivalent loading was confirmed by ethidium bromide staining. FIG.

6B: Northern blot demonstrating increased expression of MCIP1 during differentiation of C2C12 myogenic cells in culture.

FIG. 7—Gene expression profiling by microarray analysis (Incyte Genomics). Listed are the eight genes found to be potently up-regulated during compensated hypertrophy (upper panel) and in the transition to overt heart failure (lower panel) that are characteristic of this model (3), along with accession numbers and estimated fold-change in mRNA abundance. Calcineurin A is the transgene product in this model and up-regulation of atrial natriuretic factor gene expression is a well-defined marker of cardiac hypertrophy. MCIP1 (arrows) is one of the genes most strongly activated in hypertrophic, non-failing hearts of aMHC-CnA* animals, and is up-regulated further in hearts of animals that have progressed to overt cardiac failure.

Figure 8A:
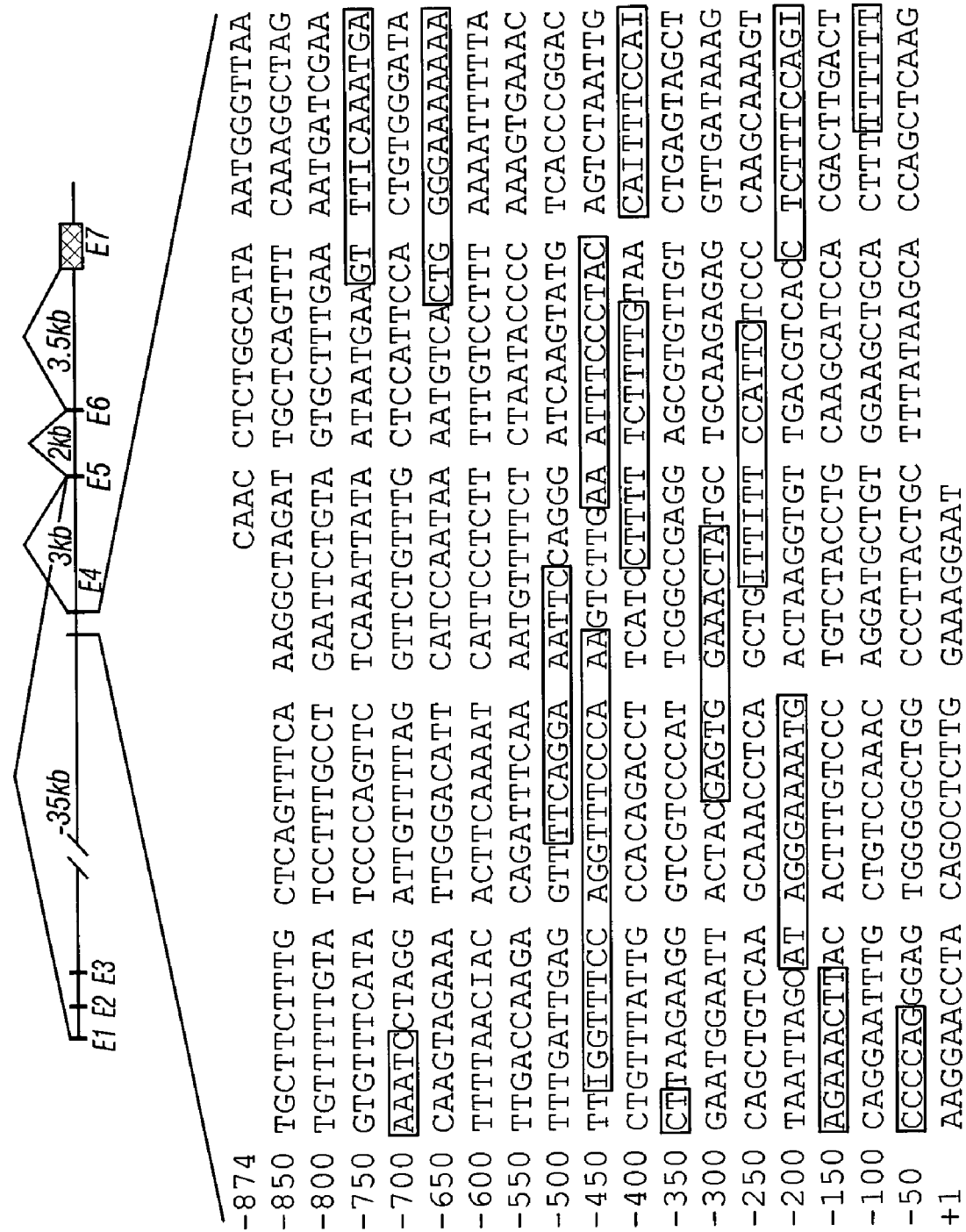
Figure 8B:
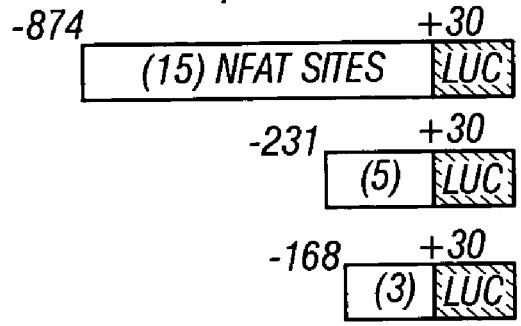
Figure 8C:
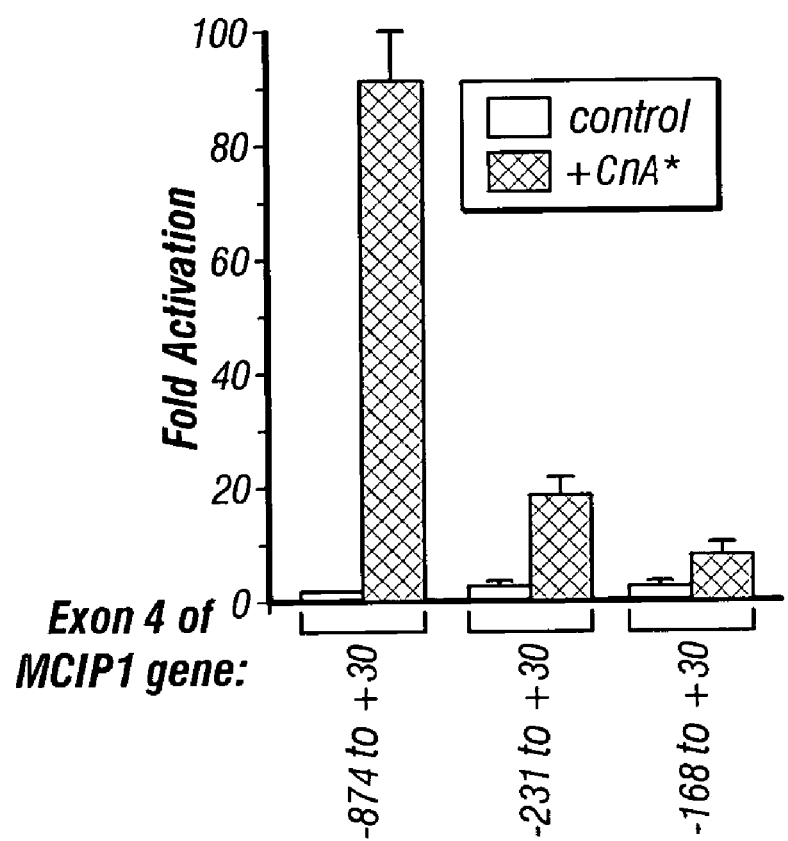

FIGS. 8A-C—An intragenic calcineurin response element from the MCIP1 gene. FIG. 8A. Schematic representation of the organization of the human MCIP1 (DSCR1) gene, indicating four alternative initial exons (E1-E4) and three exons common to all forms of MCIP1 mRNA (E5-E7)34. The nucleotide sequence flanking Exon 4 is shown to illustrate the presence of 15 consensus binding sites for NF-AT transcription factors (boxes). The first nucleotide of exon 4 is designated as +1. FIG. 8B. MCIP1 -luciferase reporter plasmids. Plasmids were constructed to link defined genomic segments proximal to exon 4 of the human MCIP1 gene to a luciferase reporter gene. The numbers of NF-AT consensus binding sites contained within each segment are shown in parenthesis. FIG. 8D. Transient transfection assays of MCIP1 -luciferase reporter plasmids. Results were corrected for variations in transfection efficiency by normalization to expression of a co-transfected pCMV-lacZ plasmid. Fold activation was determined relative to the basal activity of the *874 to +30 MCIP1 -luciferase reporter construct. Histograms represent mean values + SEM of 3 independent transfections of C2C12 myogenic cells.

Figure 9:
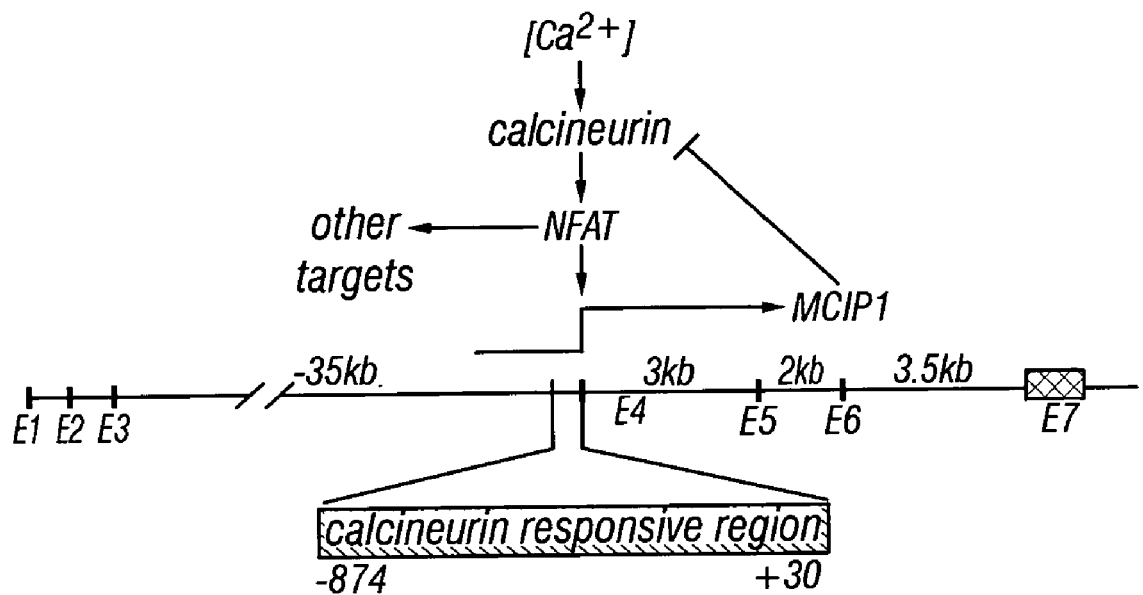

FIG. 9—A negative feedback loop for regulation of calcineurin activity. Evidence presented in this paper identifies MCIP1 as a target for positive transcriptional regulation by calcineurin in heart and skeletal muscles, probably as a direct consequence of NF-AT binding to a calcineurin responsive region in proximity to exon 4 of the MCIP1 gene. Since MCIP1 is capable of inhibiting the enzymatic activity of calcineurin (24), it is likely that this regulatory circuit serves to inhibit calcineurin activity under conditions of sustained stimulation by calcium/calmodulin, thereby to protect cells from deleterious effects of unrestrained calcineurin activation.

Figure 10:
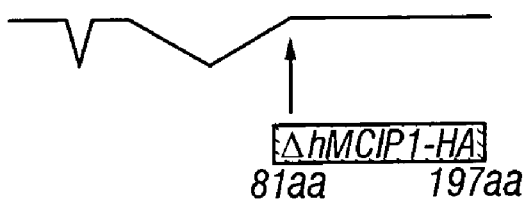

FIG. 10—Design and expression of the α-MHC-hMCIP1 transgene. Schematic illustration of components of the transgene, including a 5.5 kb α-MHC promoter fragment with three non-coding exons (E1, E2, E3) and intervening non-transcribed segments of the α-MHC gene, followed by a full length human MCIP1 cDNA with a carboxyl terminal epitope tag (HA) and a polyadenylation (pA) signal from the human growth hormone gene. The lower line illustrates the unexpected pattern of mRNA splicing observed in vivo, resulting in translation of a truncated protein (DhMICP1) initiated at amino acid 81 relative to the wild-type (WT) protein.

Figure 11:
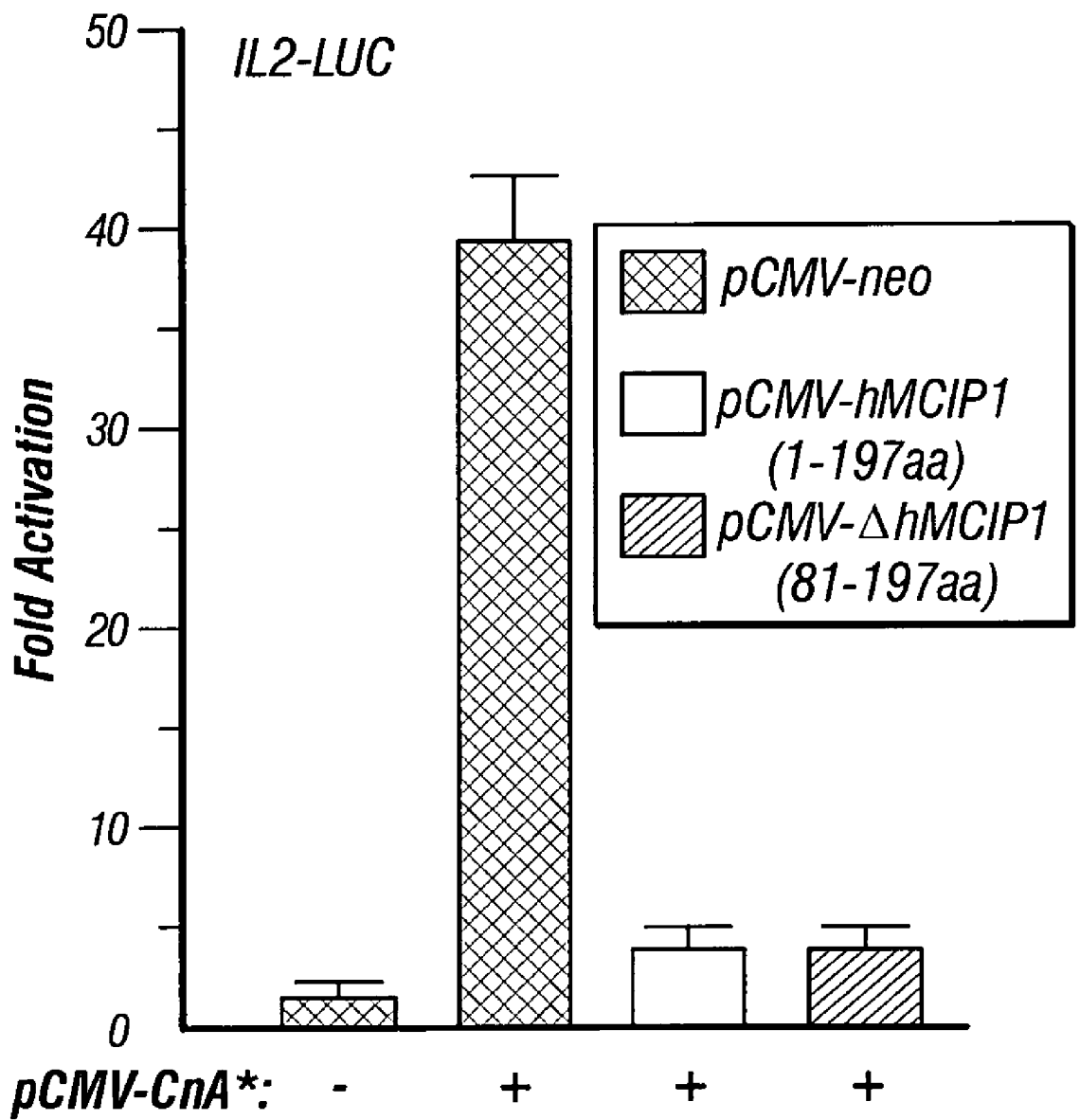

FIG. 11—Functional activity of the truncated DhMCIP1 protein product compared to full length hMCIP1, assessed by inhibition of calcineurin-dependent activation in C2C12 myoblasts. C2C12 cells were transfected with a luciferase reporter gene driven by a calcineurin-responsive IL-2 promoter (IL-2-Luc). Cells were cotransfected with a constitutively active calcineurin expression plasmid (pCMV-CnA*) and either an empty control vector (pCMV-neo) or the indicated MCIP encoding plasmid (pCMV-hMCIP1 or pCMV-ΔhMCIP 1).

Figure 12:
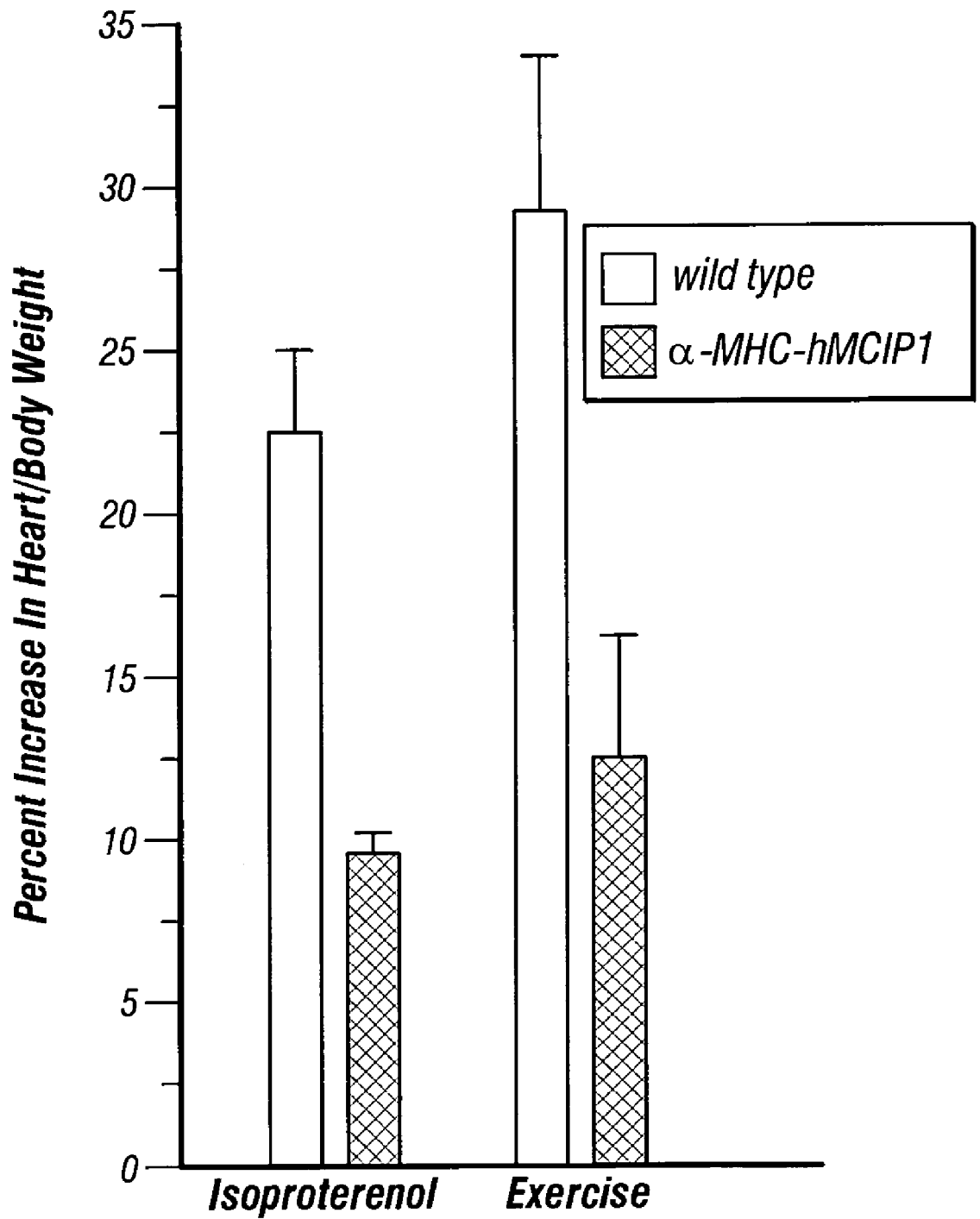

FIG. 12—Effects of hMCIP1 on cardiac hypertrophy in response to b-adrenergic receptor stimulation or exercise in intact animals. The graph indicates the percent increase in htw/bw of male wild-type (n=7) and α-MHC-hMCIP1 transgenic (n=9) mice subjected to chronic infusion of isoproterenol over seven days or the percent increase in htw/bw of male wil-type (n=4) and α-MHC-hMCIP1 transgenic (n=4) mice after 28 days of voluntary wheel running exercise. The α-MHC-hMCIP1 mice developed significantly less cardiac hypertrophy in response to either isoproterenol or exercise.

DESCRIPTION OF ILLUSTRATIVE EMBODIMENTS

Heart failure—the inability of the heart to pump blood at a rate sufficient to sustain homeostasis—is a major health issue in the world today. This is true not only due to the untimely deaths caused by heart disease, but the tremendous expense incurred due to required patient support, including prolonged hospitalization. Thus, there remains a great need to address this costly and debilitating disease.

The present inventors now report that the mammalian MCIPs (myocyte-enriched calcineurin interacting proteins) are capable of binding and inhibiting the catalytic subunit of calcineurin. MCIP proteins are structurally distinct from immunophilins, AKAP79 and cabin-1/cain proteins that have been shown previously to modulate the signaling function of calcineurin. Moreover, MCIPs are expressed most abundantly in striated myocytes of the heart and skeletal muscles, a pattern that is unique among this set of known calcineurin-interacting proteins.

In particular, cabin-1/cain is expressed at lower levels in striated muscles than in other tissues (Sun et al., 1998; Lai et al., 1998). AKAP79 and cabin-1/cain are larger proteins that appear to function as molecular scaffolds upon which hetero-oligomeric complexes that include calcineurin are assembled (Sun et al., 1998; Lai et al., 1998; Klauck et al., 1996). The contrastingly small size (22 kDa) of MCIPs suggests a different mechanism of action.

As discussed above, Rex1p (YKL159c) is a calcineurin-binding protein of *Saccharomyces cerevisiae*. A preliminary report noted that this small 24 kDa protein inhibited calcineurin signaling when overexpressed in yeast (Kingsbury and Cunningham 1998). A 30-amino acid segment of Rex1p shares homology to two different genes identified in the human gene sequence data base, DSCR1 and ZAKI-4. DSCR1 was so designated because it resides within the "Down syndrome critical region" of human chromosome 21 (Fuentes et al., 1997). Individuals trisomic for this region, which is estimated to encode 50-100 different proteins, display features of the Down syndrome phenotype. ZAKI-4 was identified from a human fibroblast cell line in a screen for genes that are transcriptionally activated in response to thyroid hormone (Miyazaki et al., 1996).

The inventors were stimulated by these observations and undertook a detailed analysis of the proteins encoded by these genes with respect to calcineurin signaling in mammalian cells. Based on these studies, DSCR1 (MCIP1) and ZAKI-4 (MCIP2) genes are capable of inhibiting calcineurin-dependent transcriptional responses in murine myocytes. MCIPs represent unique targets for efforts to regulate calcineurin signaling selectively in cardiac and skeletal myocytes.

MCIP proteins exhibit structural motifs that are shared both with Rex1p and with NFAT, the most intensively characterized phosphoprotein substrate for calcineurin. These conserved motifs within MCIP appear to have functional importance, since truncated forms of MCIP1 from which these regions have been removed are defective for binding calcineurin. MCIP1 binds within the catalytic domain of calcineurin A that is discrete from the carboxyl-terminal region required for binding of calmodulin. This result suggests that MCIP1 may contact the active site of calcineurin, perhaps functioning to inhibit access of NFAT and other phosphoprotein substrates.

MCIP1 transcripts are increased several-fold in hearts of transgenic mice overexpressing a constitutively active form of calcineurin under the control of a cardiac-specific promoter. Microarray analysis of these hearts, compared to wild-type, ranks MCIP1 as the single gene that is most dramatically upregulated. In contrast, MCIP2 transcription does not change in response to increases in calcineurin activity, suggesting that MCIP1, but not MCIP2, functions in a negative feedback loop in response to calcineurin activity. However, MCIP2 is upregulated by thyroid hormone.

Since transcription of MCIP1 is regulated so potently by calcineurin activity, the MCIP1 gene promoter becomes a valuable reagent for high throughput drug screens to identify compounds that alter calcineurin signalling. An 700 bp intragenic segment of the MCIP1 gene contains a uniquely dense cluster of 15 NFAT binding elements immediately upstream (5') to Exon 4, and the form of MCIP1 induced by calcineurin is initiated from Exon 4. This genomic organization is likely to provide the basis for the exquisite sensitivity of MCIP1 transcription to calcineurin activity. Transcription of MCIP 1 also is responsive to oxidative stress, peaking around four hours after stimulation. MCIP2 levels do not change at four hours, but decline as MCIP1 levels peak.

In particular, the inventors have identified a phosphoserine residue at amino acid 108 of MCIP1 as a substrate for calcineurin phosphatase activity. A priming phosphorylation of a serine at amino acid 112 of MCIP1 by a mitogen activited protein kinase (MAPK) is required for subsequent phosphorylation of serine 108 by glycogen synthase kinase-3 (GSK3). Calcineurin can dephosphorylate serine 108, but not remove the phosphate at serine 112. However, a mutant MCIP1 with serine 108 converted to alanine still inhibits calcineurin.

Recently, additions to the human genome data base includes a third MCIP gene, with two splice variants. This gene is located on chromosome 1, with the variants having accession numbers AF176116 (SEQ ID NOS:16 and 17) and AF176117 (SEQ ID NOS:5 and 6). These gene products are termed MCIP3a and MCIP3b by the inventors. There also appears to be a splice variant of MCIP2, now called MCIP2a and MCIP2b.

The discovery of proteins that function to regulate calcineurin-dependent signaling cascades is important, both for advancing the basic understanding of cell regulation and to provide novel targets for drug discovery. The ability of MCIPs to inhibit calcineurin activity potentially adds a level of complexity to the regulation of calcineurin signaling in those cell types in which MCIP proteins are expressed. MCIPs themselves may be subject to regulation by protein phosphorylation and dephosphorylation, and thereby may serve to integrate other signaling inputs with the calcineurin pathway. The inventors speculate that these proteins serve as negative regulators to prevent adverse consequences of unrestrained calcineurin activity in muscle tissues (Molkentin et al., Musaro et al., 1999; Semsarian et al., 1999; Dunn et al., 1999). However, it also is possible that the interaction with MCIP directs calcineurin to specific intracellular locales or to specific phosphoprotein substrates.

Current results indicate that the interaction between MCIP and calcineurin is pertinent to the pathobiology, and ultimately to the therapy, of human disease, For example, familial forms of hypertrophic cardiomyopathy are caused by mutations in genes encoding proteins of the sarcomere (Seidman and Seidman, 1998), in a manner that is likely to involve calcineurin signaling (Marban et al., 1987). Administration of the calcineurin antagonist drugs cyclosporin A or FK-506 prevents cardiac hypertrophy in transgenic animal models of familial forms of hypertrophic cardiomyopathy (Sussman et al., 1998), but the analogous clinical trials are precluded because of toxic side effects (e.g., immunosuppression and hypertension) of existing agents.

It also is possible, in some clinical situations, that faciliation of cardiac hypertrophy without other aspects of the disease could prove beneficial. Again, MCTP's involvement in this process makes it a suitable candidate for intervention, this time by antagonizing MCIP rather than calcineurin.

Calcineurin antagonists also prevent cardiac hypertrophy and heart failure in some, although not all, animal models of acquired forms of cardiomyopathy that are common in human populations (Sussman et al., 1998; Ding et al., 1999; Zhang et al., 1999), but the same limitations to clinical trials apply. The relative abundance of MCIP1 in cardiac muscle recommends it as a target for drug development to circumvent these limitations of current calcineurin antagonists.

I. MCIP Peptides and Polypeptides

The human gene (DSCR1) encoding MCIP1 is one of 50-100 genes that reside within a critical region of chromosome 21 (Fuentes et al., 1997; Fuentes et al., 1995), trisomy of which gives rise to the complex developmental abnormalities of Down syndrome, which include cardiac abnormalities and skeletal muscle hypotonia as prominent features (Epstein, 1995). ZAKI-4 was identified from a human fibroblast cell line in a screen for genes that are transcriptionally activated in response to thyroid hormone (Miyazaki et al, 1996).

Applicants provide protein sequences for human MCIP1, MCIP2 and MCIP3 (SEQ ID NOS:2, 4, 6 and 17) and mouse MCIP1 and MCIP2 (SEQ ID NOS:8 and 10). In addition to the entire MCIP1, MCIP2 and MCIP3 molecules, the present invention also relates to fragments of the polypeptides that may or may not retain various of the functions described below. Fragments, including the N-terminus of the molecule may be generated by genetic engineering of translation stop sites within the coding region (discussed below). Alternatively, treatment of the MCIPs with proteolytic enzymes, known as proteases, can produces a variety of N-terminal, C-terminal and internal fragments. Examples of fragments may include contiguous residues of SEQ ID NOS:2, 4, 6, 8, 10 and 17 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration)

A. Structural Features

MCIP1 is the product of a human gene previously called, DSCR1, and it includes several domains of proven or potential biological interest: an acidic domain (EKEEEEEME), a serine-proline motif (SPPASPP), a leucine-rich putative DNA binding domain (LHKTEFLGKEMKLYFAQTL), and regions with the characteristics of an SH3 or SH2 domain ligand (HLAPPNPDK and PEYTPI, respectively). Fuentes et al. (1997). Multiple versions of MCIP1 exist due to four alternative first exons, which are alternatively joined to Exons 5-7. It is the form of MCIP1 initiated at Exon 4 that is transcriptionally induced by calcineurin activity. MCIP2, also known as ZAKI-4, is a 192 AA polypeptide having 62% homology with MCIP 1. Proline and valine residues are found with abundance within MCIP2. Miyazaki et al. (1996).

B. Functional Aspects

MCIP1 is a binding partner for calcineurin. In addition, it is an antagonist of calcineurin-dependent transcriptional activation. MCIP1 also acts as a substrate for phosphoryalation by MAPK and GSK-3, and calcineurin's phosphatase activity. Residues 81-177 of MCIP1 retain the calcineurin inhibitory action.

Binding of MCIP1 to calcineurin does not require calmodulin, nor does MCIP interfere with calmodulin binding to calcineurin. This suggests that the surface of calcineurin to which MCIP1 bindings does not include the calmodulin binding domain. In contrast, the interaction of MCIP1 with calcineurin is disrupted by FK506:FKBP or cyclosporin:cyclophylin, indicating that the surface of calcineurin to which MCIP1 binds overlaps with that required for the activity of immunosuppressive drugs.

C. Variants of MCIP1 and MCIP2

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0 ±1); glutamate (+3.0 ±1); serine (+0.3); asparagine (+0.2) glutamine (+0.2); glycine (0); threonine (−0.4); proline (−0.5 ±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al, 1993).

The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MCIP1, MCIP2 and MCIP3, but with altered and even improved characteristics.

D. Domain Switching

As described in the examples, the present inventors have identified murine MCIP1, MCIP2 and MCIP3. Given the homology with other Midline proteins, an interesting series of mutants can be created by substituting homologous regions of various proteins. This is known, in certain contexts, as "domain switching."

Domain switching involves the generation of chimeric molecules using different but, in this case, related polypeptides. By comparing various MCIP proteins, one can make predictions as to the functionally significant regions of these molecules. It is possible, then, to switch related domains of these molecules in an effort to determine the criticality of these regions to MCIP 1, MCIP2 and MCIP3 function. These molecules may have additional value in that these "chimeras" can be distinguished from natural molecules, while possibly providing the same function.

E. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

F. Purification of Proteins

It will be desirable to purify MCIP1, MCIP2, MCIP3 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

The present invention also describes smaller MCIP-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

H. Antigen Compositions

The present invention also provides for the use of MCIP1, MCIP2 and MCIP3 proteins or peptides as antigens for the immunization of animals relating to the production of antibodies. It is envisioned that MCIP1, MCIP2, MCIP3 or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

II. Nucleic Acids

The present invention also provides, in another embodiment, genes encoding MCIP1 and MCIP2. Genes for human MCIP1 (SEQ ID NO:1), MCIP2 (SEQ ID NO:3) and MCIP3 (SEQ ID No:5 and 17) have been identified. Also provided are MCIP1 and MCIP2 from mouse (SEQ ID NOS:7 and 9). The present invention is not limited in scope to these genes, however, as one of ordinary skill in the could, using these nucleic acids, readily identify related homologs in various other species (e.g., rat, rabbit, dog, monkey, gibbon, human, chimp, ape, baboon, cow, pig, horse, sheep, cat and other species).

In addition, it should be clear that the present invention is not limited to the specific nucleic acids disclosed herein. As discussed below, an "MCIP gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of MCIP1, MCIP2 or MCIP3.

A. Nucleic Acids Encoding MCIP1, MCIP2 and MCIP3

Nucleic acids according to the present invention may encode an entire MCIP1, MCIP2 or MCIP3 gene, a domain of MCIP1, MCIP2 or MCIP3, or any other fragment of MCIP1, MCIP2 and MCIP3 as set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given MCIP from a given species may be represented by natural variants that have slightly different nucleic acid sequences but, nonetheless, encode the same protein (see Table 1 below).

As used in this application, the term "a nucleic acid encoding a MCIP" refers to a nucleic acid molecule that has been isolated free of total cellular nucleic acid. In preferred embodiments, the invention concerns a nucleic acid sequence essentially as set forth in SEQ ID NOS:1, 3, 5, 7, 9 and 16. The term "as set forth in SEQ ID NOS: 1, 3, 5, 7, 9 or 16" means that the nucleic acid sequence substantially corresponds to a portion of SEQ ID NO:1, 3, 5, 7, 9 or 16. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NOS:1, 3, 5, 7, 9 and 16 are contemplated. Sequences that are essentially the same as those set forth in SEQ ID NOS:1, 3, 5, 7, 9 and 16 also may be functionally defined as sequences that are capable of hybridizing to a nucleic acid segment containing the complement of SEQ ID NOS:1, 3, 5, 7, 9 and 16 under standard conditions.

The DNA segments of the present invention include those encoding biologically functional equivalent MCIP proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NOS:1, 3, 5, 7, 9 and 16. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NOS:1, 3, 5, 7, 9 and 16 under relatively stringent conditions such as those described herein. Such sequences may encode the entire MCIP proteins or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 3431 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to MCIP1, MCIP2, or MCIP3 or, more particularly, homologs of MCIP1, MCIP2 or MCIP3 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et a., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a MCIP polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

In certain embodiments, the native MCIP promoter will be employed to drive expression of either the corresponding MCIP gene, a heterologous MCIP gene, a screenable or selectable marker gene, or any other gene of interest. Of particular interest is the 700 bp immediately upstream of Exon 4 of the human MCIP gene. As discussed above, this region contains a high concentration of binding sites for the transcription factor NFAT and therefore is likely to play an important regulatory function, especially in light of the existence of a transcript initiating at Exon 4.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; |

TABLE 2-continued

Promoter and/or Enhancer

| Promoter/Enhancer | References |
|---|---|
| | Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immuno-deficiency Virus | Muesing et al., 1987; Hauber et al., 1988; Jakobovits et al., 1988; Feng et al., 1988; Takebe et al., 1988; Rosen et al., 1988; Berkout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al, 1996), the troponin 1 promoter (Bhavsar et al., 1996); the $Na^+/Ca^{2+}$ exchanger promoter (Barnes et al., 1997), the dystrophin promoter (Kimura et al., 1997), the creatine kinase promoter (Ritchie M. E., 1996), the alpha7 integrin promoter (Ziober &

Kramer, 1996), the brain natriuretic peptide promoter (LaPointe et al., 1996) and the alpha B-crystallin/small heat shock protein promoter (Gopal-Srivastava, R., 1995), alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham; et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1 -deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1 -coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

III. Generating Antibodies Reactive With MCIP1, MCIP2 and MCIP3

In another aspect, the present invention contemplates an antibody that is immunoreactive with a MCIP molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to MCIP-related antigen epitopes. Additionally, it is proposed that monoclonal antibodies specific to the particular MCIP of different species may be utilized in other useful applications In general, both polyclonal and monoclonal antibodies against MCIPs may be used in a variety of embodiments. For example, they may be employed in antibody cloning protocols to obtain cDNAs or genes encoding other MCIPs. They may also be used in inhibition studies to analyze the effects of MCIPs related peptides in cells or animals. MCIPs antibodies will also be useful in immunolocalization studies to analyze the distribution of MCIPs during various cellular events, for example, to determine the cellular or tissue-specific distribution of MCIPs polypeptides under different points in the cell cycle. A particularly useful application of such antibodies is in purifying native or recombinant MCIPs, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis)*, incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MCIP protein, polypeptide or peptide or cell expressing high levels of MCIP. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

IV. Diagnosing and Treating Defects in MCIPs

The inventors have shown MCIPs play an important role in the regulation of calcineurin, which in turn is a key regulator of cardiac hypetrophy. In addition, reduction in MCIP activity, which in turn can deregulate calcineurin and play in important role in cardiac disease. Thus, in another embodiment, there are provided methods for diagnosing defects in MCIP expression and function. More specifically, point mutations, deletions, insertions or regulatory pertubations relating to MCIPs may be assessed using standard technologies, as described below.

A. Genetic Diagnosis

One embodiment of the instant invention comprises a method for detecting variation in the expression of MCIP1, MCIP2 and MCIP3. This may comprises determining that level of MCIP1, MCIP2 or MCIP3 or determining specific alterations in the expressed product.

A suitable biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Various types of defects may be identified by the present methods. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of MCIP produced, both by altering the transcription of the gene or in destabilizing or otherwise altering the processing of either the transcript (mRNA) or protein.

It is contemplated that other mutations in the MCIP genes may be identified in accordance with the present invention. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the MCIP genes that may then be analyzed by direct sequencing.

(vi) Kit Components

All the essential materials and reagents required for detecting and sequencing MCIP1, MCIP2 and MCIP3 and variants thereof may be assembled together in a kit. This generally will comprise preselected primers and probes. Also included may be enzymes suitable for amplifying nucleic acids including various polymerases (RT, Taq, Sequenase ™ etc.), deoxynucleotides and buffers to provide the necessary reaction mixture for amplification. Such kits also generally will comprise, in suitable means, distinct containers for each individual reagent and enzyme as well as for each primer or probe.

B. Immunologic Diagnosis

Antibodies of the present invention can be used in characterizing the MCIP content of healthy and diseased tissues, through techniques such as ELISAs and Western blotting. This may provide a screen for the presence or absence of cardiomyopathy or as a predictor of heart disease.

The use of antibodies of the present invention, in an ELISA assay is contemplated. For example, anti-MCIP antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for MCIP1, MCIP2 or MCIP3 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

C. Treating Defects in MCIP Expression or Function

The present invention also involves, in another embodiment, the treatment of disease states related to the aberrant expression and/or function of MCIPs. In particular, it is envisioned that reduced MCIP activity plays a role in cardiac failure through deregulation of calcineurin. Thus, increasing levels of MCIPs, or compensating for mutations that reduce or eliminate the activity of MCIPs, are believed to provide therapeutic intervention in cardiomyopathies.

One of the therapeutic embodiments contemplated by the present inventors is the intervention, at the molecular level, in the events involved in cardiac failure. Specifically, the present inventors intend to provide, to a cardiac cell, an expression construct capable of providing MCIP1, MCIP2 or MCIP3 to that cell. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below. Various routes are contemplated, but local provision to the heart and systemic provision (intraarterial or intravenous) are preferred.

In another embodiment, it is contemplated that blocking of calcineurin's phosphatase activity also will prove beneficial in the treatment of heart disease. This may be accomplished in one of several ways. First, by providing a phosphorylated version of a peptide containing the Ser108 site of MCIP1, one my simply overwhelm the ability of calcineurin to remove phosphates from endogenous MCIP1. Second, using a similar approach, an analog of this same peptide, with an unremovable phosphate group may be used, effectively creating a "suicide substrate" for calcineurin. This approach also could be exploited using a mimetic (see above). Third, one could use the a peptide chimera containing MCIP1's Ser108 site as "bait," with the other portion of the chimera containing an molecule that binds to and/or cleaves calcineurin. And fourth, any of the preceding methods could be accomplished by using an expression construct encoding the Ser108 peptide.

D. Combined Therapy

In many clinical situations, it is advisable to use a combination of distinct therapies. Thus, it is envisioned that, in addition to the therapies described above, one would also wish to provide to the patient more "standard" pharmaceutical cardiac therapies. Examples of standard therapies include so-called "beta blockers", anti-hypertensives, cardiotonics, anti-thrombotics, vasodilators, hormone antagonists, endothelin antagonists, calcium channel blockers, phosphodiesterase inhibitors, angiotensin type 2 antagonists and cytokine blockers/inhibitors. Also envisioned are combinations with pharmaceuticals identified according to the screening methods described herein.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a MCIP-1 or MCIP-2 gene, or the other agent will be desired. Various combinations may be employed, where MCIP is "A" and the other agent is "B", as exemplified below:

```
A/B/A  B/A/B  B/B/A  A/A/B  B/A/A  A/B/B  B/B/B/A  B/B/A/B

A/A/B/B  A/B/A/B  A/B/B/A  B/B/A/A  B/A/B/A  B/A/A/B  B/B/B/A

A/A/A/B  B/A/A/A  A/B/A/A  A/A/B/A  A/B/B/B  B/A/B/B  B/B/A/B
```

Other combinations are contemplated as well.

E. Formulations and Routes for Administration to Patients

Where clinical applications are contemplated, it will be necessary to prepare pharmaceutical compositions—expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Methods of Making Transgenic Mice

A particular embodiment of the present invention provides transgenic animals that contain MCIP-related constructs. Transgenic animals expressing MCIP1, MCIP2 and MCIP3, recombinant cell lines derived from such animals, and transgenic embryos may be useful in methods for screening for and identifying agents that modulate the function of MCIP1, MCIP2 or MCIP3, and thereby alleviate pathology related to the over or under expression of these molecules. The use of constitutively expressed MCIPs provides a model for over- or unregulated expression. Also, transgenic animals which are "knocked out" for MCIP1, MCIP2 and/or MCIP3.

A. Methods of Producing Transgenics

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. *Manipulating the Mouse Embryo* (Cold Spring Harbor Laboratory, Cold Spring Harbor, N.Y., 1986), in Palmiter et al. Nature 300:611 (1982); in *The Qiagenologist, Application Protocols*, 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

B. Disease Models

Defects in MCIPs are believed to lead to increases in calcineurin activity. Therefore, it is contemplated that by reducing the expression and/or activity of MCIPs, the activity of calcineurin will effectively be increased. Through earlier studies, overexpression of calcineurin has been shown to cause cardiac hypertrophy. Thus, in embodiments where it is desired that levels of calcineurin not be altered, it is still possible to create a hypertrophic situation by inhibiting or blocking MCIPs expression or activity.

VI. Screening Assays

Thus, the present invention also contemplates the screening of compounds for various abilities to interact and/or affect MCIP1, MCIP2 and MCIP3 expression or function. Particularly preferred compounds will be those useful in inhibiting or promoting the binding of MCIP1, MCIP2 and MCIP3 to calcineurin. In the screening assays of the present invention, the candidate substance may first be screened for basic biochemical activity—e.g., binding to a target molecule—and then tested for its ability to inhibit modulate expression, at the cellular, tissue or whole animal level.

A. Modulators and Assay Formats i) Assay Formats

The present invention provides methods of screening for modulators of MCIP1, MCIP2 and MCIP3 expression. In one embodiments, the present invention is directed to a method of:
  (i) providing a MCIP1, MCIP2 or MCIP3 polypeptide;
  (ii) contacting the MCIP1, MCIP2 or MCIP3 polypeptide with the candidate substance;
  (iii) contacting the MCIP1, MCIP2 or MCIP3 with calcineurin; and
  (iv) determining the binding of MCIP1, MCIP2 or MCIP3 polypeptide or calcineurin.

In another embodiment, this assay can be easily modified to look at the candidate substances effects on MCIP1, MCIP2 and/or MCIP3 binding to calcineurin. Another assay screens for MCIP1 dephosphorylation:
  (a) providing a phosphorylated MCIP1 and calcineurin;
  (b) admixing the MCIP1 and calcineurin in the presence of a candidate modulator;
  (c) assessing MCIP1 phosphorylation; and
  (d) comparing the phosphorylation state of MCIP1 in step (c) with the phosphorylation state of MCIP1 in the absence of the candidate modulator.

A difference in MCIP phosphorylation in the presence of the candidate modulator, as compared to phosphorylation in the absence of said candidate modulator, identifies the candidate modulator as a modulator of MCIP phosphorylation.

In still another embodiment, the assay looks not at binding, but a MCIP expression. Such methods would comprise, for example:
  (i) providing a cell that expresses MCIP1, MCIP2 or MCIP3 polypeptide;
  (ii) contacting the cell with the candidate substance; and
  (iii) determining the effect of the candidate substance on expression of MCIP 1, MCIP2 or MICP3 polypeptide.

It is not even necessary that MCIP be screened directly. Rather, a marker gene can be linked to an MCIP promoter. Expression of the marker protein, which is much easier to assay, is used as a surrogate for MCIP expression. In still other embodiments, one would look at the effect of a candidate substance on the mRNA synthesis, although alterations in mRNA stability and translation would not be accounted for.

In still yet another embodiment, one may look at one or more characteristics of a muscle cells to which a candidate substance is provided. This cell may be engineered in a variety of manners. First, it could be engineered for over- or underexpression of an MCIP, calcineurin or both. Second, it could be engineered to contain a marker gene under the control of a promoter that is regulated by calcineurin or some transcriptional activator downstream of calcineurin.

ii) Inhibitors and Activators

An inhibitor according to the present invention may be one which exerts an inhibitory effect on the expression of function of MCIP1, MCIP2 and/or MCIP3. By the same token, an activator according to the present invention may be one which exerts a stimulatory effect on the expression of function of MCIP1, MCIP2 and/or MCIP3.

iii) Candidate Substances

As used herein, the term "candidate substance" refers to any molecule that may potentially modulate MCIP1, MCIP2 and/or MCIP3 expression or function. The candidate substance may be a protein or fragment thereof, a small molecule inhibitor, or even a nucleic acid molecule. It may prove to be the case that the most useful pharmacological compounds will be compounds that are structurally related to compounds which interact naturally with MCIP1, MCIP2 and/or MCIP3. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like a MCIP, and then design a molecule for its ability to interact with that MCIP. Alternatively, one could design a partially functional fragment of a MCIP (binding but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

In this case, there is ample evidence that demonstrates the binding of MCIPs to calcineurin. By analyzing the binding of MCIPs to this target molecule, much information can be gleaned about the ability of MCIPs to recognize calcineurin. With this information, predictions can be made regarding the structure of potential inhibitors or activators of MCIPs.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include antisense molecules, ribozymes, and antibodies (including single chain antibodies), each of which would be specific for a target located within the calcineurin pathway. Such compounds are described in greater detail elsewhere in this document.

It will, of course, be understood that all the screening methods of the present invention are useful in themselves notwithstanding the fact that effective candidates may not be found. The invention provides methods for screening for such candidates, not solely methods of finding them.

B. In vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to a MCIP1, MCIP2 or MCIP3 molecule or fragment thereof is provided.

The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as a MCIP). Competitive binding assays can be performed in which one of the agents (MCIP for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, a MCIP and washed. Bound polypeptide is detected by various methods. Purified target, such as a MCIP, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of a MCIP) to a solid phase.

C. In cyto Assays

Various cell lines that express MCIP1, MCIP2 and or MCIP3 can be utilized for screening of candidate substances. For example, cells containing a MCIP with an engineered indicators can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, $Ca^{++}$ effects). Alternatively, molecular analysis may be performed in which the function of a MCIP and related pathways may be explored. This involves assays such as those for protein expression, enzyme function, substrate utilization, mRNA expression (including differential display of whole cell or polyA RNA) and others.

D. In vivo Assays

The present invention particularly contemplates the use of various animal models. Transgenic animals may be created with constructs that permit MCIP expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for method of producing inhibitors. The methods comprising any of the preceding screening steps followed by an additional step of "producing the candidate substance identified as a modulator of" the screened activity.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Materials and Methods

Plasmid Constructs—An HA-tagged splice variant 4 of human MCIP1 (GenBank Accession No. U85267) was isolated from a human placental cDNA library by PCR using the primers:

5'-AGAACCATGCATTTTAGAAACTTTAACTACAGTTTTAG-3' and

5'-TAGAGCGTAGTCTGGGACGTCGTATGGGTAGCTGAGGTGGATCGGCG-3'

A c-myc-tagged splice variant 4 of mouse MCIP1 (GenBank Accession No. AA200984) was isolated from a mouse cardiac cDNA library by PCR using the primers:

5'-GAATTCCACCATGGAACAAAAACTTATTTCTGAAGAAGATCTGG
   ATTTTAGGGACTTTAGCTAC-3' and

5'-GGATCCTCAGTTGGACACGGAGGGTGG-3'

A c-myc-tagged splice variant 1 of mouse MCIP1 (GenBank Accession No. AA734360) was isolated from a mouse EST cDNA clone (Research Genetics, IMAGE 1223388) by PCR using the primers:

5'-GAATTCCACCATGGAACAAAAACTTATTTCTGAAGAAGATCTGGAG
   GAGGTGGATCTGCAG-3' and

5'-GGATCCTCAGTTGGACACGGAGGGTGG-3'

A c-myc-tagged mouse MCIP2 (GenBank Accession No. AU035927) was isolated from the mouse EST clone MNCb-1054 (provided by K. Hashimoto, Japanese Collection of Research Bioresources, Tokyo, Japan) by PCR using the primers:

5'-GAATTCCACCATGGAACAAAAACTTATTTCTGAAGAAGATCTGCCAG
   CCCCTAGCATGGAC-3' and

5'-GGATCCTCAGTTGGACACGGAGGGTGG-3'

The isolated PCR products described above were subcloned into mammalian expression plasmids pTARGET™ (Promega), or pEGFP-N1 (CLONTECH).

GST-MCIP1 fusions were expressed from the bacterial expression plasmid pGEX-CS (T. D. Parks, et al. 1994). Luciferase reporter plasmids, Mb-luc and IL-2-luc, were constructed in pGL3 (Promega) by inserting promoter/enhancer regions from genes encoding human myoglobin (Chin et al., 1998) or IL-2 (Clipstone et al., 1992), respectively. In addition, a synthetic enhancer consisting of three copies of a high affinity MEF2 binding sequence from the desmin promoter (Naya et al., 2000) was linked to a minimal promoter (hsp68) and inserted into pGL3 yielding the des-MEF-luc reporter. The β-galactosidase reporter plasmid pCMV-lacZ (J. Grayson, et al. 1998), and expression vectors encoding constitutively active forms of NFAT (Molkentin et al., 1998), calcineurin (CnA*) (Chin et al., 1998, O'Keefe et al., 1992), or calmodulin dependent protein kinase type IV (CaMKIV) (Ho et al., 1996), were previously described. The identity of plasmid constructions was confirmed by restriction mapping and partial DNA sequencing.

Tissue Culture, Cell Transfection, and Reporter Gene Assays—C2C12 myoblasts were grown in Dulbecco's modified Eagle's medium supplemented with 20% fetal bovine serum and antibiotics (100 units of penicillin and 100 g of streptomycin/ml). Myotube formation was induced by switching confluent cells to differentiation media (Dulbecco's modified Eagle's medium supplemented with 2% heat-inactivated horse serum) for 48-72 h. For transient transfection assays, C2C12 cells were plated 12 h before transfection in 12-well tissue culture dishes at 5×104 cells/well, and transfected with a total of 0.5 µg of plasmid DNA using LipofectAMINE Plus (Life Technologies, Inc.). Myoblasts were harvested 24 h after transfection. Myotubes were obtained by shifting cultures to differentiation media 24 h after transfection and harvesting 48 h later. To stimulate transfected cells, 1 µM ionomycin and 10 ng/ml phorbol myristate acetate (PMA) were added 4.5 h prior to harvesting. Luciferase assays of whole cell extracts were conducted as described previously (Yang et al., 1997).

In Vitro Protein-Protein Interaction Assays—GST and GST-MCIP1 fusion proteins were prepared as described previously (Grayson et al., 1998). [$^{35}$S]Methionine labeled CnA398, CnA342, and CnA266 were produced in the TNT coupled in vitro transcription/translation system (Promega). For in vitro binding assays, equivalent amounts of GST fusion proteins bound to glutathione were resuspended in 500 µl of binding buffer (20 mM Tris, pH 7.5, 100 mM KCl, 0.1 mM EDTA, 0.05% Nonidet P-40, 10% glycerol, and 1 mg/ml bovine serum albumin). [$^{35}$S]Methionine-labeled CnA proteins were added to the resuspended GST fusion proteins and incubated for 1 h. The beads were then spun down and washed three times in binding buffer. An equal volume of 2×SDS-PAGE loading buffer was added, and the suspension was boiled for 3 min. The bound proteins were then resolved on SDS-PAGE and visualized by autoradiography. $^{35}$S-Labeled luciferase protein (Promega) was used as a negative control. For estimation of binding efficiency, 25% of the radiolabeled protein was loaded as an input control.

Fluorescence Microscopy—An Olympus IMT-2 inverted fluorescence photomicroscope was used for evaluation and photography of C2C12 cells transfected with GFP expression plasmids. GFP fluorescence (excitation peak=488 nm, emission peak=507 nm) was photographed using an Optronics VI-470 CCD camera and a Power Macintosh G3 equipped with a Scion CG-7 frame grabber and Scion Image software.

Cell Fractionation—C2C12 cells in 35-mm plates were transfected with mammalian expression plasmids encoding an activated form of calcineurin (CnA*) and MCIP1-GFP. Twenty-four hours after transfection, the cells were washed twice with ice-cold phosphate-buffered saline and then scraped from plates in 55 µl of ice-cold lysis buffer (20 mM HEPES, pH 7.4, 10 mM NaCl, 1.5 mM MgCl2, 20% glycerol, 0.1% Triton X-100, 1 mM dithiothreitol, and protease inhibitor mixture (Roche Molecular Biochemicals)). The cells were spun in a microcentrifuge at 1,000 rpm for 1 min at 4° C. The supernatant contained the cytoplasmic fraction. The nuclear pellet was resuspended in 60 µl of lysis buffer, and 8.3 µl of 5 M NaCl was added to lyse the nuclei. This mixture was rotated at 4° C. for 1 h, then spun in a microcentrifuge at maximal speed for 15 min at 4° C. The supernatant contained the soluble nuclear fraction. The pellet was resuspended in 60 µl of lysis buffer. An equal volume of 2×SDS-PAGE loading buffer was added to each fraction. The samples were boiled for 3 min prior to loading on a 12.5% SDS-PAGE gel. The proteins were transferred to a nylon membrane and then probed with a mouse monoclonal GFP antibody (CLONTECH), followed by a goat anti-mouse secondary antibody coupled to horseradish peroxidase (Pierce). SuperSignal (Pierce) was used for detection.

RNA Isolation and Analysis—Total RNA was prepared from mouse tissues or C2C12 cells using RNAzol (Life Technologies, Inc.) following the manufacturer's protocol. Northern blot analysis was performed with 20 µg of total RNA in each lane and probed in Ultrahyb (Ambion) with a DNA fragment from the 3'-untranslated region of mouse MCIP1 isolated from a mouse EST clone (Research Genetics, IMAGE 1223388) by PCR using the primers (5'-GGCAT-CAGGTTATTCAGAGT-3' and 5'-GTGGAGTCCGTCG-TAGCCAT-3') or the open reading frame of mouse MCIP2 cDNA.

B. Results

Figure 1A:
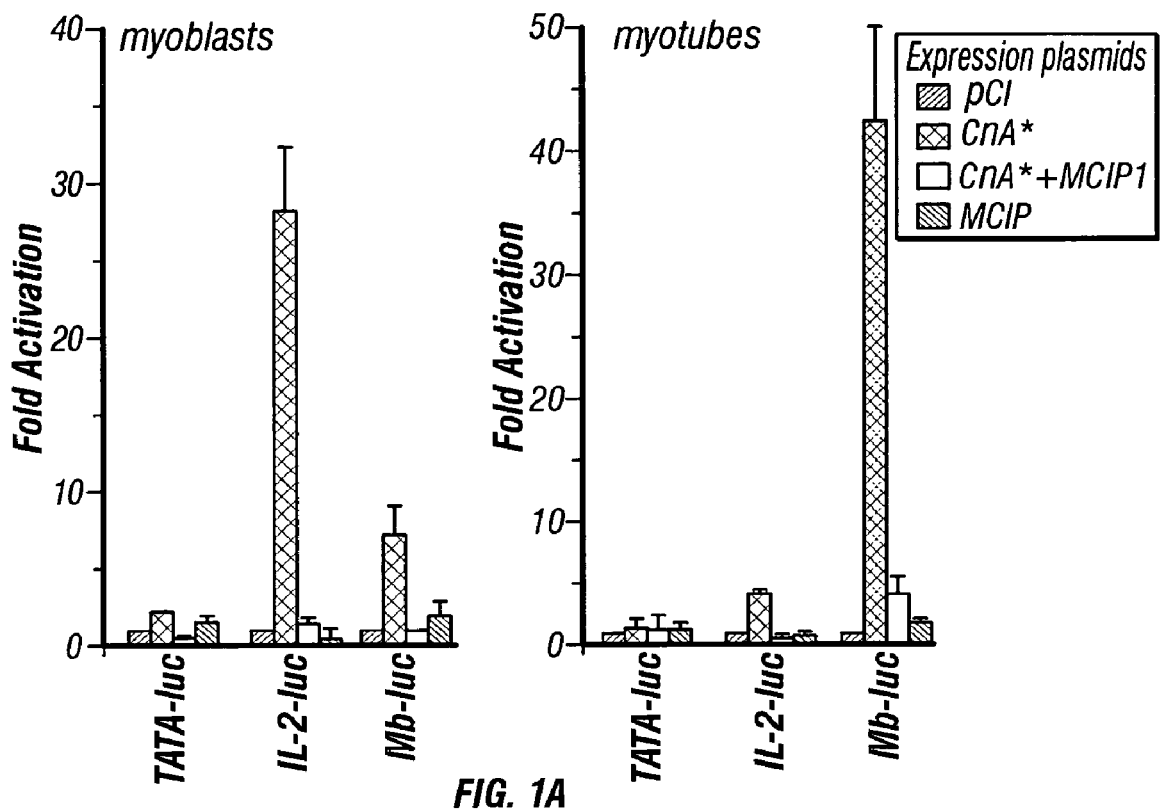
FIGS. 1A-B—MCIP1 inhibits calcineurin-dependent transcriptional responses in C2C12 myogenic cells. Luciferase reporter constructs under the control of a minimal promoter (TATA-luc) or promoter/enhancer elements from the myoglobin (Mb-luc) or interleukin-2 (IL-2-luc) genes were cotransfected into C2C12 cells along with expression plasmids containing either no insert (pCI), or CnA*, or MCIP1. Data are expressed relative to the luciferase activity observed in the control state (pCI) and represent mean values (± S.E.) of duplicate determinations from three or more independent experiments. All results are corrected for variations in transfection efficiency by normalization to expression of a co-transfected pCMV-lacZ plasmid.

Forced Expression of MCIP1 Blocks Calcineurin-Dependent Transcriptional Activation in Cultured Skeletal Myoblasts and Myotubes—To determine whether MCIP alters calcineurin signaling in mammalian muscle cells, a mouse myoblast cell line, C2C12, was transfected with plasmid DNA constructs expressing human MCIP1 and a constitutively active form of calcineurin (CnA*) (O'Keefe et al., 1992) along with luciferase reporter plasmids controlled either by a minimal promoter (TATA-luc) or two different calcineurin-responsive enhancer constructs from the human interleukin-2 (IL-2-luc) (Clipstone et al., 1992) or myoglobin (Mb-luc) (Chin et al., 1998) genes. The minimal TATA promoter was unresponsive to either CnA* or MCIP1 in both proliferating myoblasts and differentiated myotubes (FIG. 1A). Both the IL-2 and Mb enhancer constructs were activated by CnA*, and this effect was abolished by forced expression of MCIP1. MCIP1 alone had no effect on the activity of any constructs.

It is interesting to note that calcineurin-dependent activation of the IL-2 enhancer is greater in proliferating myoblasts than in differentiating myotubes. Conversely, the muscle-specific Mb enhancer is more responsive in the differentiated cell background, probably reflecting a functional collaboration between NFAT and myogenic determination factors such as MEF2. MCIP reverses calcineurin-dependent activation of either enhancer at either developmental stage, suggesting that the mechanisms of inhibition are independent of the specific downstream effectors that are transducing the calcineurin signal.

The ability of MCIP to inhibit calcineurin-dependent gene transcription was distinguished from generalized transcriptional repression by analysis of a different reporter construct that is not influenced by calcineurin signaling. C2C12 cells were transfected with a luciferase reporter plasmid under the control of a multimerized Gal4p binding motif (UASg-TATA-luc). Forced expression of a fusion protein that links the DNA binding domain of Gal4p to the potent transactivation domain of VP16 (Gal4-VP16) increased reporter gene transcription markedly (FIG. 1B), but this induction was not affected by MCIP 1.

Figure 1B:
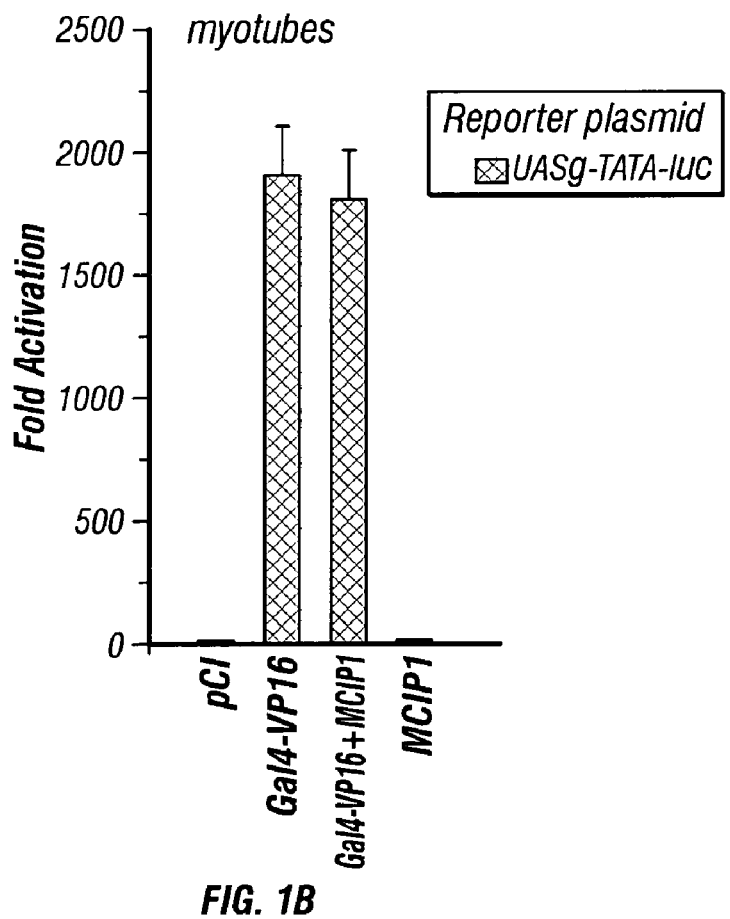

MCIP1 Inhibits Endogenous Calcineurin Activated by PMA/Ionophore Stimulation—The results in FIG. 1A-B indicate that overexpression of MCIP inhibits a constitutively active form of calcineurin, but a different design was required to determine whether this inhibitory function extends to the native protein. Endogenous calcineurin of C2C12 cells was stimulated as described previously in other cell types (Loh et al., 1996) using a combination of phorbol myristate acetate (PMA) and a Ca2+ ionophore. PMA/ionophore stimulation activated the myoglobin enhancer (Mb-luc) in both myoblasts and myotubes (FIG. 2A), and this response was inhibited by co-transfection of the MCIP1 expression plasmid. The incomplete reversal by MCIP1 of Mb enhancer activity driven by PMA/ionophore may reflect a calcineurin-independent signaling component that is triggered by this stimulus. This conclusion is supported by the observation that cyclosporin A only partially reverses the effects of PMA/ionophore stimulation in the same experimental system (data not shown).

MCIP1 Does Not Inhibit a Constitutively Active Form of NFAT—To distinguish an effect on calcineurin itself from an inhibitory mechanism acting upon downstream effectors of calcineurin signaling, the ability of MCIP1 to interfere with transcriptional activation driven by a variant form of NFAT that is constitutively active in the absence of calcineurin signaling (Rao et al., 1997) was assessed. This variant of NFATc, termed NFAT here, has been truncated to remove the amino-terminal regulatory domain, but retains DNA binding and transcriptional activation functions of the native protein. As a consequence of this truncation, NFAT is partitioned constitutively to the nuclear compartment, where it activates the IL-2 enhancer without a requirement for calcineurin activity (FIG. 2B). Forced expression of MCIP does not inhibit transcriptional activation mediated by NFAT (FIG. 2B), in contrast to its effects on calcineurin-dependent transcription (FIGS. 1A-B and 2A-C). This result is interpreted to indicate that the inhibitory action of MCIP on calcineurin signaling is based on a direct interaction with calcineurin, rather than interference with downstream components of calcineurin-dependent signaling pathways.

MCIP Inhibits Calcineurin-dependent Regulation of MEF2—Previous experiments in (Chin et al., 1998), and by others (Liu et al., 1997, Mao et al., 1999, Youn et al., 1999), have indicated that the transactivating function of MEF2 transcription factors, in addition to NFAT proteins, is modified by calcineurin activity. The precise mechanism of this response has not been elucidated, but this interaction can be demonstrated in a myocyte cell background using a MEF2-dependent reporter plasmid (des-MEF2-luc) constructed by linking three copies of a high affinity MEF2 binding site from the human desmin gene to a minimal promoter (Naya et al., 2000). Transcription of the des-MEF2-luc reporter is up-regulated synergistically in skeletal myoblasts by constitutively activated forms of calcineurin (CnA*) and calmodulin-dependent protein kinase IV (CaMKIV*) (FIG. 2C). In a manner similar to its effect on calcineurindependent activation of the myoglobin and IL-2 promoter/reporter constructs (see FIGS. 1A-B), MCIP1 inhibited activation of the des-MEF2-luc reporter by CnA* alone, or by the combination of CnA* with CaMKIV (FIG. 2C). Since the des-MEF2-luc reporter lacks an NFAT binding site, the inhibitory effect of MCIP observed with this reporter suggests that MCIP acts to inhibit the action of calcineurin on multiple substrates, rather than by interference that is limited to the NFAT:calcineurin interaction.

Figure 3:
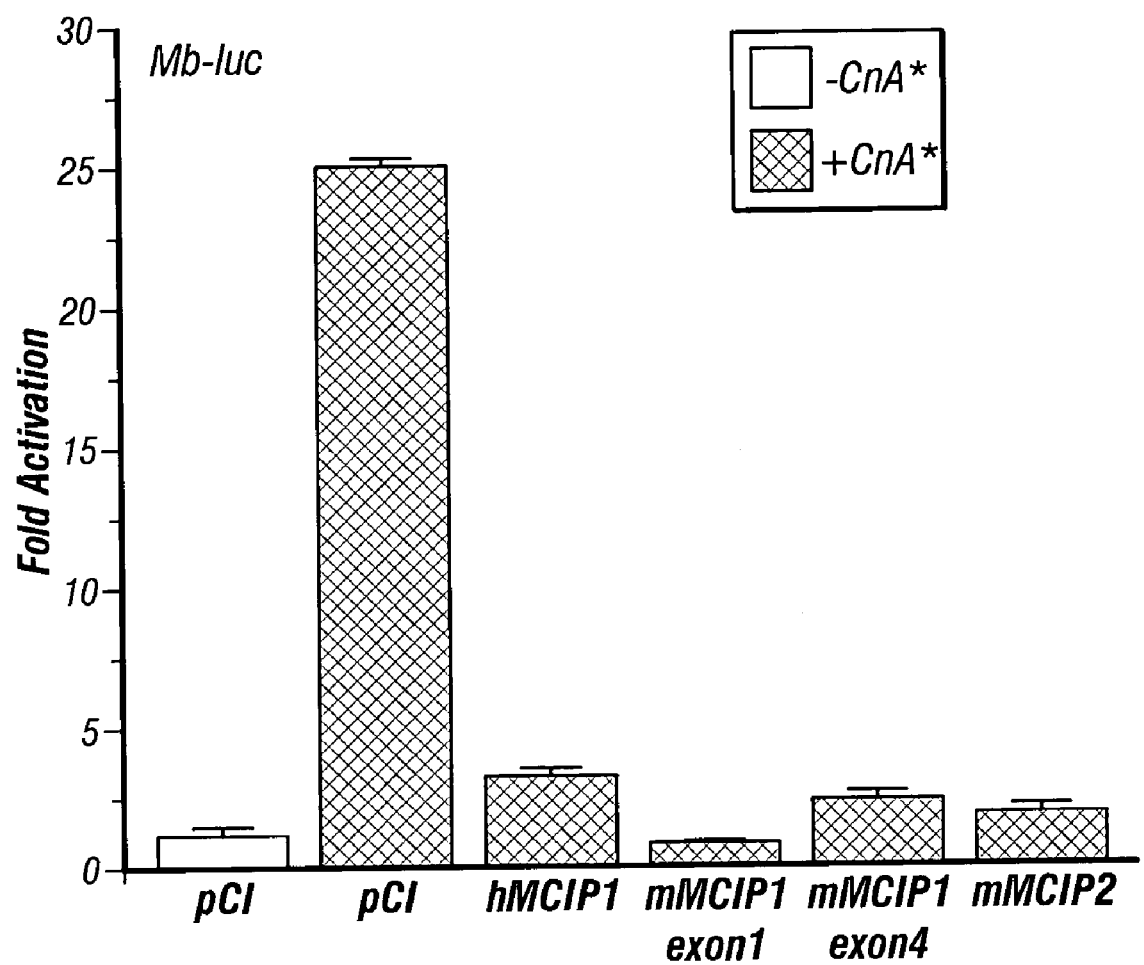
FIG. 3—Splice variants of MCIP1 and MCIP2 inhibit calcineurin signaling. C2C12 cells were cotransfected with the Mb-luc reporter plasmid, an empty control vector (pCI), or expression vectors encoding constitutively active calcineurin (CnA*), human MCIP1 (hMCIP1), two splice variants of murine MCIP1 (mMCIP1/exon 1 or mMCIP1/exon4), or murine MCIP2 (mMCIP2) as indicated. Cells were harvested 48 h after transfection. Luciferase expression was determined in the absence (open bar) or presence (filled bars) of constitutively active calcineurin (CnA*). Data were calculated as described in FIGS. 1A-B. All results are corrected for variations in transfection efficiency by normalization to expression of a co-transfected pCMV-lacZ plasmid.

Multiple Members of the Family of MCIP Proteins Can Inhibit Calcineurin—The human DSCR1 gene that encodes the protein now termed MCIP1 is composed of seven exons (Fuentes et al., 1997). In humans, there are four splice variants each starting with a different initiating exon (1, 2, 3, or 4), followed by exons 5, 6, and 7. Splice variants 1 and 4 account for the vast majority of detectable transcripts. Exons 1 and 4 each encode the first 29 amino acids of proteins encoded by this gene and are more than 70% identical. Proteins produced from all splicing variations share the regions encoded by exons 5-7. The splice variant of MCIP1 initiated by exon 4 (SEQ ID NOS: 20 and 21) was used in most of the experiments reported here. It has been determined, however, that proteins encoded by human splice variant 1 (SEQ ID NOS:18 and 19), and by murine splice variants 1 and 4 (SEQ ID NOS:12, 13, 14, 15), function similarly to inhibit calcineurin signaling to the myoglobin enhancer in a myocyte cell background (FIG. 3). Likewise, the protein now termed MCIP2, encoded by the ZAKI-4 gene, is 70% identical to MCIP1 and inhibits calcineurin-dependent transcriptional activation in this co-transfection assay (FIG. 3).

MCIP1 Interacts with the Catalytic Domain of CnA—Recombinant MCIP1 protein, or truncated forms thereof, were purified from bacterial cell lysates as fusion proteins linked to glutathione S-transferase (GST-MCIP1). Binding of GST-MCIP1 to calcineurin in a cell free environment was assessed using the constitutively active calcineurin variant (CnA398), or truncated forms thereof, that were expressed and metabolically labeled with [$^{35}$S]methionine in coupled in vitro transcription/translation reactions.

Figure 4A:
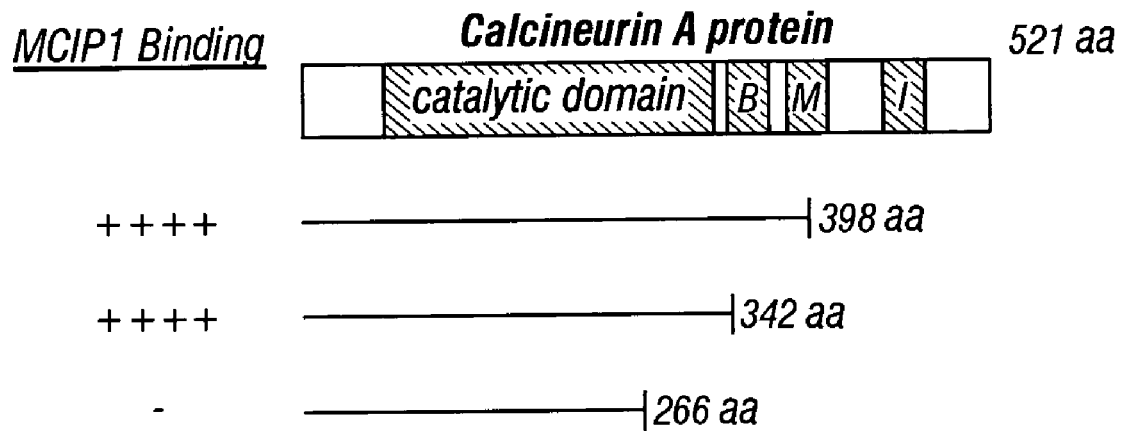
FIGS. 4A-B—MCIP1 binds the catalytic domain of calcineurin A.
Figure 4B:
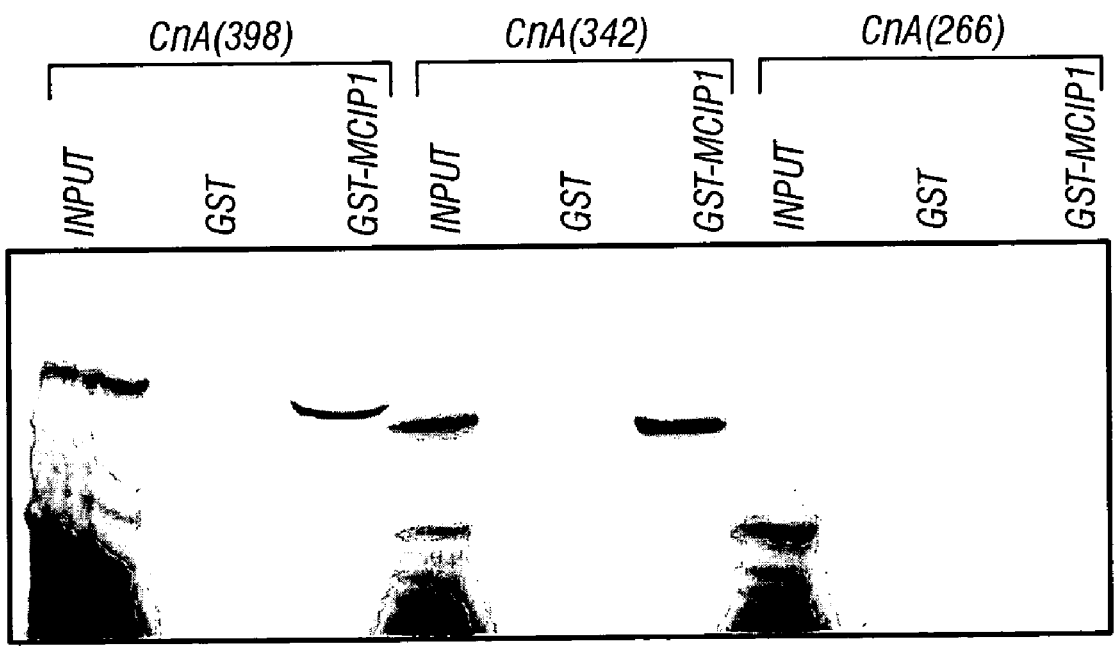

In vitro translated CnA(398) lacking the autoinhibitory domain (I) and part of the calmodulin binding site (M) forms a physical complex with GST-MCIP1 (FIGS. 4A-B). Deletion of the regions of CnA that bind calmodulin (M) and calcineurin B (B), as represented by CnA(342), did not disrupt the interaction with MCIP1. However, a protein that was truncated further to remove the carboxyl-terminal half of the catalytic domain of CAN (CnA(266)) was no longer capable of binding MCIP1. It is concluded, therefore, that MCIP interacts with the catalytic domain of calcineurin A. Binding of MCIP, therefore, may occlude the active site as a mechanism for the functional inhibition observed in vivo.

Figure 5A:
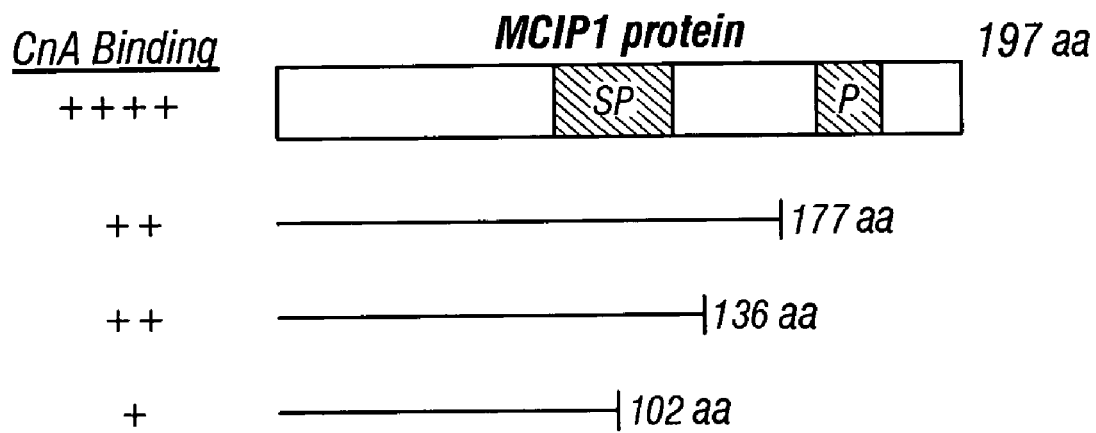
FIGS. 5A-B—Conserved regions of MCIP1 mediate the interaction with calcineurin A.
Figure 5B:
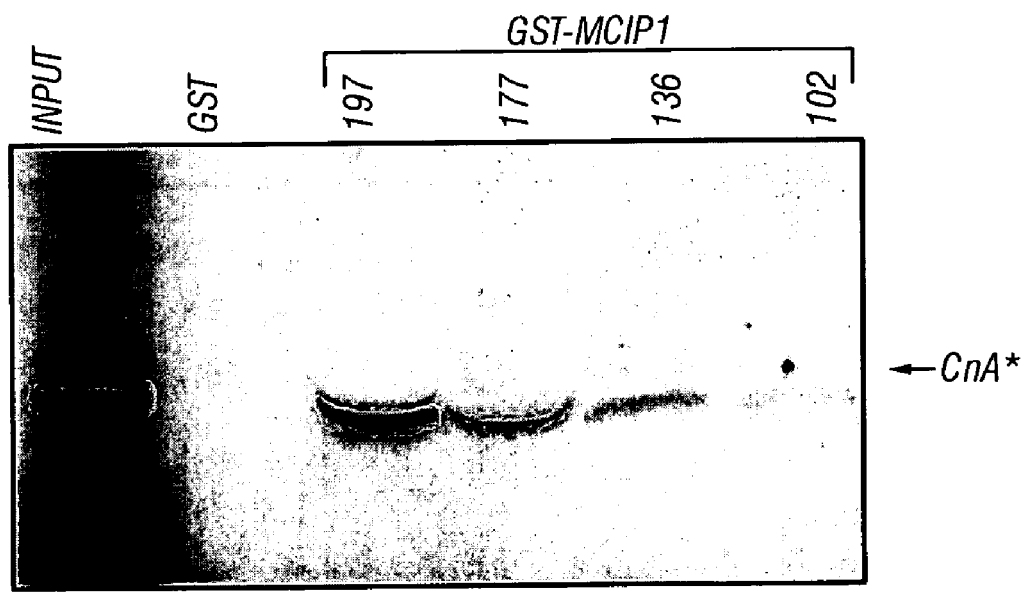

There are two regions of MCIP proteins that resemble motifs found in NFAT that mediate interactions with calcineurin (FIGS. 5A-B). The first of these is an SP repeat motif contained within a 30-amino acid region of MCIP that also is homologous to yeast REX1p (Kingsbury et al., 1998). NFAT proteins include three sets of these repeats (Masuda et al., 1995, Ho et al., 1995, Hoey et al., 1995), and it is dephosphorylation of serine residues within this region by calcineurin that results in nuclear localization and transcriptional activation by NFAT (Loh et al., 1996, Shibasaki et al., 1996, Luo et al., 1996, Beals et al., 1997 and Masuda et al., 1997). MCIP1 has only one SP repeat motif, and it differs also from NFAT by including two versus three SP pairs (SPXXSPXXXXXEE in MCIP versus SPXXSPXXSPXXXXX(E/D)(E/D) in NFAT). A second region of MCIP, PXIXXT, at amino acid residues 181-186 of MCIP1 resembles the NFAT PXIXIT motif that has been defined functionally as a calcineurin docking site (43, 44). Truncation of MCIP1 so as to delete the PXIXXT motif from the carboxyl terminus (GST-MCIP1-177) reduced binding of MCIP to CnA* but did not abolish it (FIGS. 5A-B). Further deletion of the carboxyl end of MCIP (GST-MCIP1-136), leaving the SP repeat intact, did not significantly reduce binding further. However, a truncation mutant that lacks both the PXIXXT motif and the SP repeat (GST-MCIP1-102) had lower affinity for binding calcineurin in this assay. The inventors conclude that both of these domains contribute to the calcineurin MCIP1 interaction.

Figure 6A:
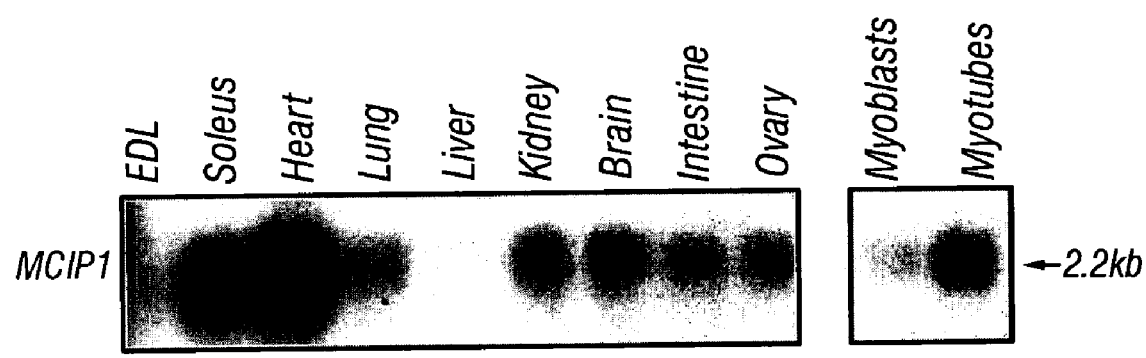
FIGS. 6A-B—Muscle-selective expression of MCIP1 and MCIP2 mRNA.
Figure 6B:
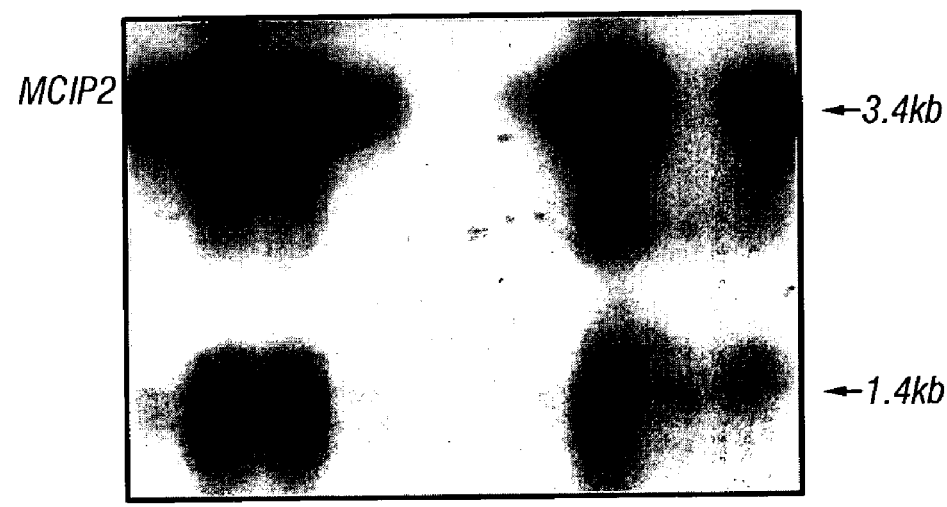

The Subcellular Localization of MCIP1 is Altered by Activated Calcineurin—A GFP-tagged human MCIP1 protein (MCIP-GFP) was expressed in C2C12 myoblasts to assess the subcellular distribution of MCIP1 in this cell background. Twenty hours after transfection, GFP-tagged MCIP1 was localized predominately to the nuclear compartment (FIG. 6A). After 48 h, very little of the MCIP-GFP protein remained. Co-transfection of plasmids encoding CnA* altered this pattern, such that after 24 h MCIP-GFP was observed predominately in the cytoplasm, and a fluorescent signal remained detectable for several days. The morphology of some cells suggested a nearly complete nuclear exclusion of MCIP-GFP in the presence of CnA* (FIG. 6B). Activation of endogenous calcineurin by addition of PMA/ionophore to the medium after transfection also resulted in the accumulation of MCIP-GFP in the cytoplasm (FIG. 6C). The subcellular distribution of native GFP was unaffected by co-expression of calcineurin.

C2C12 myoblasts transfected with MCIP-GFP were fractionated to separate cytoplasmic (C), soluble nuclear (S), and insoluble nuclear matrix (M) components. In the absence of activated calcineurin, MCIP1-GFP was present in both the nuclear soluble (S) and nuclear matrix (M) fractions. Expression of an activated form of calcineurin, CnA*, however, altered this association of MCIP1 with the nuclear matrix, such that soluble MCIP1 became detectable in both the soluble nuclear and cytoplasmic fractions (FIG. 6F). Overexpression of proteins in transfected cells can lead to a number of artifacts. Nevertheless, the effect of calcineurin expression on nuclear partitioning and chromatin binding of MCIP1 bolsters the conclusion that a physical interaction between MCIP 1 and calcineurin is pertinent to the functional interactions that have been observed.

MCIP1 and MCIP2 are Expressed Most Abundantly in Striated Myocytes, and Their Expression is Up-regulated During Muscle Differentiation—Gene-specific probes complementary to the 3'-untranslated regions of the mouse MCIP1 and MCIP2 cDNAs were used to examine expression of these genes in cultured myogenic cells and in tissues of adult mice. C2C12 myoblasts express low levels of MCIP1 mRNA transcript, but, upon differentiation of these cells into striated myotubes, expression increases severalfold (FIGS. 6A-B). In adult mice, MCIP1 and MCIP2 are expressed most abundantly in heart and skeletal muscles. MCIP2 also is highly expressed in brain, but all other tissues express lower levels of both transcripts (FIGS. 6A-B). These results are consistent with previous descriptions of transcripts derived from the DSCR1 and ZAKI-4 genes in human tissues (Miyazaki et al., 1996, Fuentes et al., 1995).

The analysis of MCIP1 and MCIP2 mRNAs in murine tissues also revealed differential expression of these transcripts among different skeletal muscle groups. The soleus muscle of the mouse (and other mammals) is enriched in slow, oxidative (Type I) myofibers, while the extensor digitorum longus is enriched in myofibers of the fast, glycolytic subtype (type IIb) (Schiaffino et al., 1996). The expression of MCIP1 and MCIP2 is markedly increased in soleus muscle relative to extensor digitorum longus (FIGS. 6A-B), suggesting a selective activation of these genes in type I fibers. This result is particularly interesting in light of the evidence that calcineurin activity is an important determinant of the slow fiber phenotype (Chin et al., 1998, Dunn et al., 1999).

Calcineurin-MCIP1 Double Transgenics Do Not Develop Cardiac Hypertrophy—As previously reported, transgenic mice that contain calcineurin transgenes under the control of the α-MHC promoter develop massive cardiac hypertrophy. The inventors constructed α-MHC-MCIP1 transgenic mice. These mice appeared normal, although their hearts were slightly smaller than their wild-type littemates.

A cross was performed between the ax-MHC-calcineurin transgenic mice and the alpha-MCH-MCIP1 transgenic mice. Mice carrying both transgenes appear normal. This striking result confirms the inventors' hypothesis that overexpression of MCIP1 is sufficient to prevent cardiac hypertrophy and heart failure. The data for two-month old male animals are as follows:

TABLE 4

| Genotype | Body Wt | Heart Wt | Heart Wt/Body Wt |
|---|---|---|---|
| α-MHC-Cal | 25.5 g | .288 g | .0113 |
| α-MHC-Cal/MCIP | 24.0 g | .176 g | .0073 |

Example 2

A. Materials and Methods

Plasmid constructions: The segment of intron 3 from the human MCIP1 (DSCR1) gene was isolated by PCR using human genomic DNA as template and primers based on sequence information from the human Chromosome 21 data bank (29). This ~900 bp fragment was subcloned into a pGL3 luciferase reporter vector (Promega). Other plasmids were previously described (Chin et al., 1998; Rothermel et al., 2000).

Tissue culture, cell transfection or infection, reporter gene assays: C2C12 myoblasts and myotubes were cultured as previously described (Grayson et al, 1995). Ionomycin (2 mM) and cyclosporin A (50 to 200 nM) were added 4 hrs prior to harvesting the cells. When included, cyclohexamide (25 mM) was added 15 min prior to ionomycin. Transient transfection with plasmids or infection with recombinant, replication-defective adenoviruses, and luciferase assays were performed as previously reported (Chin et al, 1998; Rothermel et al., 2000; Wu et al., 1973).

Animal experiments: Lines of transgenic mice in which the cc myosin heavy chain promoter is used to drive expression of a constitutively active form of calcineurin selectively in the heart were generated and described previously (Molkentin et al., 1998). Wildtype male C57Bl/6 mice were injected intraperitoneally with 3, 5, 3'-triiodothyromine (T3) (0.1 mg/g body weight) or an equal volume of 0.9% saline once a day for ten days (Robbins & Swain, 1992). All experiments involving animals were conducted using IACRAC-approved protocols.

RNA isolation and Northern blot analysis: Total RNA was prepared from mouse tissues or C2C12 cells using Tripure (Boehringer Mannheim, Inc.) following the manufacturer's protocol. Northern blot analysis was performed with 20 mg of total RNA in each lane and probed in Ultrahyb (Ambion) with complementary sequences representing the 3' UTR of MCIP1 (common to all known splicing variants), exon 1 of MCIP1, exon 4 of MCIP1, or ORF segments of MCIP2 or GAPDH cDNA. Probes were generated by PCR and labeled as described previously (Rothermel et al., 2000). Signals from Northern blots were detected on a Storm PhosphorImager (Molecular Dynamics) and quantified using ImageQuant (version 1.2).

cDNA microarray analysis of calcineurin-transgenic mice: RNA was isolated from two calcineurin-transgenic mice (Molkentin et al., 1998) at 10 weeks of age, and from a wild-type littermate. One of the transgenic mice was determined to be in heart failure, on the basis of anasarca with massive ascites, while the other appeared grossly normal. Both transgenic mice showed >100% increase in heart weight relative to the wildtype control (250 mg and 240 mg vs. 96 mg, respectively). Total body weights of the wildtype (26 g) and non-failing calcineurin transgenic mice (27.5 g) were comparable, while the calcineurin-transgenic mouse in heart failure had a greater body weight of 35.6 g, reflecting the edematous state. Microarray analyses were conducted by Incyte Genomics as described elsewhere (Schena et al., 1996). Briefly, polyA+ RNA was labeled with Cy3/Cy5 fluorescent dyes and hybridized with a mouse cDNA microarray (mouse GEM 1.14) containing 8,734 elements each (7,832 unique genes: 3336 annotated/ 4496 unannotated) genes. Differential expression was calculated as the ratio of fluorescent signals after subtraction of background.

B. Results

Calcineurin induces expression of MCIP1 but not MCIP2: Gene expression profiling by microarray analysis was conducted to identify genes that are differentially regulated in hearts of transgenic mice engineered to express a constitutively active form of calcineurin, as compared to normal controls. Calcineurin-transgenic animals α-MHC-CnA*) develop massive cardiac hypertrophy that progresses to dilated cardiomyopathy3. This analysis identified MCIP 1 as a gene that is potently up-regulated in this model (FIG. 7). Other genes known to be controlled by hypertrophic signals (e.g., atrial natriuretic factor) also were identified by this analysis, and were induced to a comparable extent (approximately 3-fold) as MCIP1 in hypertrophic, non-failing hearts of animals at 10 weeks of age, as compared to a wild-type littermate (FIG. 7, upper panel). Both MCIP1 and calcineurin A transcripts were elevated further in hearts of age-matched animals that had progressed to overt heart failure, compared to levels noted in hypertrophic, non-failing hearts (FIG. 7, lower panel). This induction of MCIP1 gene expression within the intact myocardium by activated calcineurin was confirmed by Northern blot analysis. Quantitative estimates of the extent of MCIP1 induction in aMHC-CnA* hearts (Table 5) varied among individual animals of comparable age (3- to 17-fold), perhaps reflecting different stages in disease progression. Northern blots also revealed that the MCIP2 gene was not similarly regulated. In contrast to the up-regulation of MCIP1 mRNA in this model, there was no detectable change in MCIP2 mRNA (Table 5, right hand panel).

TABLE 5

Quantitative Estimates of Changes in MC1P1 and MC1P2 mRNA in Response to Calcineurin and Thyroid Hormone

| | $A_1$ Response to Calcineurin Activation | | | | $B_1$ Response to Thyroid Hormone | | |
|---|---|---|---|---|---|---|---|
| Stimulus | Tissue | MC1P1 | MC1P2 | Stimulus | Tissue | MC1P1 | MC1P2 |
| αMHC-CnA* | Heart | 6.03 | 1.31 | T3 | Heart | 1.05 | 1.59 |
| | Heart | 3.70 | 0.79 | T3 | Heart | 0.87 | 1.81 |
| | Heart | 16.77 | 1.32 | T3 | Heart | 1.08 | 1.71 |
| CMV-CnA* | C2C12 | 1.48 | ND | T3 | Soleus | 0.78 | 1.72 |
| | C2C12 | 1.54 | 0.91 | T3 | Soleus | 1.05 | 2.21 |

TABLE 5-continued

Quantitative Estimates of Changes in MC1P1 and MC1P2 mRNA in Response to
Calcineurin and Thyroid Hormone

| A. Response to Calcineurin Activation | | | | B. Response to Thyroid Hormone | | | |
|---|---|---|---|---|---|---|---|
| Stimulus | Tissue | MC1P1 | MC1P2 | Stimulus | Tissue | MC1P1 | MC1P2 |
| Ionomycin | C2C12 | 2.42 | 0.94 | T3 | Soleus | 1.24 | 1.62 |
|  | C2C12 | 1.94 | 1.00 |  |  |  |  |
|  | C2C12 | 1.26 | 1.12 |  |  |  |  |
| Can Effect |  | $4.80 \pm 1.30$ | $1.06 \pm 0.11$ | T3 Effect |  | $1.01 \pm 0.06$ | $1.78 \pm 0.01$ |

Each line presents the fold change induced by the stimulus within a single experimental animal (heart), pooled muscles from two animals (soleus), or a single-cell culture dish (C2C12), quantified by PhosphorImager analysis of Northern blots in duplicate or triplicate, after background subtraction and normalization to a loading control (GAPDH mRNA). The aggregate effects of calcineurin (Can) and thyroid hormone (T3) are presented as mean values ($\pm$SE) of these 14 experiments.
ND indicates not determined.

The inventors also assessed the ability of calcineurin to stimulate expression of MCIP1 in C2C12 cells that differentiate into skeletal myotubes in cell culture. Increased intracellular calcium concentrations evoked by administration of the calcium ionophore ionomycin led rapidly (<4 hr) to an increased abundance of MCIP1 mRNA in C2C12 cells. MCIP1 mRNA is increased during differentiation of C2C12 cells (reported previously (Rothermel et al., 2000), not shown here), but a 2-fold induction of MCIP1 by ionomycin was evident irrespective of the stage of differentiation (myoblasts or myotubes) and the correspondingly lower or higher initial levels of MCIP1 mRNA. In contrast, expression of MCIP2 mRNA was unaffected by ionomycin (Table 5, left hand panel). To determine if the induction of MCIP1 gene expression by calcium ionophore was attributable to calcineurin activity, as opposed to other calcium-regulated signaling events, the inventors assessed the effects of cyclosporin A on this response. In a dose-dependent manner, cyclosporin A blocked the ability of ionomycin to up-regulate MCIP 1 transcript levels in C2C12 cells, and even reduced MCIP1 transcripts below the levels observed in cells untreated with either drug, presumably by blocking basal as well as ionophore-stimulated calcineurin activity. Compared to cells treated with the highest dose of cyclosporin, MCIP1 mRNA was increased 4-fold by ionomycin in the absence of cyclosporin. In addition, MCIP1 mRNA was increased 2-fold in cultured myocytes by infection with a recombinant adenoviral vector encoding a constitutively activated form of calcineurin, as compared to the effects of infection by an control virus encoding Green Fluorescent Protein (GFP). Thus, experimental strategies based on loss-of-function and gain-of-function approaches in cultured myocytes support the conclusion that MCIP1 gene expression, but not that of MCIP2, is regulated by calcineurin signaling.

Induction of MCIP1 expression by calcineurin does not require new protein synthesis: In the presence of cyclohexamide, an inhibitor of protein synthesis, activation of calcineurin by ionomycin continued to up-regulate MCIP1 mRNA in C2C12 cells, indicating that this induction is not dependent on the generation of new proteins. The magnitude of ionomycin-stimulated up-regulation of MCIP1 in the presence of cyclohexamide (~10-fold) was greater than that observed when cyclohexamide was absent (~2-fold). The inventors interpret these data to support the hypothesis that calcineurin stimulates MCIP1 gene transcription by post-translational modification of a pre-existing pool of NF-AT proteins (and possibly other transcription factors). The greater magnitude of MCIP1 induction by calcineurin when new protein synthesis is blocked is potentially attributable to abrogation of calcineurin-dependent induction of endogenous MCIP 1 synthesis, thereby eliminating negative feedback that otherwise would restrain calcineurin activity.

Thyroid hormone induces expression of MCIP2 but not MCIP1: The gene encoding MCIP2 was identified originally in a subtractive cloning experiment designed to identify genes that are up-regulated by thyroid hormone in cultured human fibroblasts (Miyazaki et al., 1996). To determine whether MCIP genes are regulated by thyroid hormone in hearts of intact animals, hyperthyroidism was induced in wildtype mice by intraperitoneal injection of T3 for ten days. As noted previously (Robbins & Swain, 1992), T3 treated hearts were uniformly hypertrophic (mean heart weight=180 mg versus 130 mg; mean heart weight/body weight ratio=7.2 mg/gm versus 4.9 mg/gm; n=4 animals in each group). In contrast to the effects of activated calcineurin in the murine heart (FIG. 7), the expression of MCIP 1 was unaltered in hyperthyroid hearts. However, MCIP2 transcript levels were increased approximately 2-fold in both heart and soleus skeletal muscles of T3-treated mice (Table 5, right hand panel). It remains to be determined whether the effects of T3 are a direct consequence of nuclear receptor binding to regulatory elements of the MCIP2 gene, or a result of indirect mechanisms.

An intragenic region located 5' to exon 4 of the MCIP1 gene is sufficient to promote a transcriptional response to calcineurin: The human MCIP1 gene (annotated initially as DSCR1) was reported to express four variant mRNAs with each of four alternative exons incorporated selectively at the 5' terminus of the expressed transcripts (Fuentes et al., 1997). The majority of these transcripts were identified to represent isoforms that include sequences encoded either by exon 1 or exon 4 (Fuentes et al., 1997). These variants have unique 5' UTR regions, and encode proteins that differ within the first 29 amino acids. The remaining 168 residues of MCIP1, encoded by exons 5-7, are identical in all MCIP1 variants (FIG. 8A). In experiments on hearts of transgenic mice, the inventors determined that expression of the exon 4 variant of MCIP1 mRNA was particularly sensitive to calcineurin activity. The increased abundance of MCIP1 mRNA detected by a probe complementary to the 3' UTR, which is included within all variants of MCIP1 (FIG. 8A), was mirrored by the increase detected with a probe complementary only to unique exon 4 sequences. In contrast, MCIP1 transcripts that include exon 1 sequences were present only at the limit of detection in wild-type murine hearts, and were not induced by the activated calcineurin transgene (not shown).

The selectively increased expression of the exon 4 variant of MCIP1 mRNA suggested the possibility of alternative promoter usage as a function of calcineurin activation, and the inventors sought to determine whether transcriptional regulatory elements involved in transducing this signal reside in proximity to exon 4 of the MCIP1 gene. Accordingly, the inventors isolated a ~900 bp genomic segment from this position (−874 to +30 relative to the first nucleotide of exon 4). This region was found to contain a remarkably dense cluster of consensus NF-AT binding motifs (T/AG-GAAANA/T/C)35 (FIG. 8A). A reporter plasmid was constructed to link this MCIP1 genomic region to a luciferase reporter gene (FIG. 8B), and this construct was tested for its ability to respond to calcineurin after transfection into C2C12 cells. Like the endogenous MCIP1 gene, expression of this transgene is increased by activated calcineurin (FIG. 8C), which has no effect on a control plasmid (minimal TATA plus luciferase; not shown). Inhibition of calcineurin activity by concomitant over-expression of MCIP1 represses this response (not shown). Luciferase reporter plasmids controlled by shorter segments of this genomic region 5' to exon 4 (−231 to +30 or −163 to +30; FIG. 8B) retain basal activity equivalent to the −874 to +30 segment, but progressively lose calcineurin responsiveness as the number of NF-AT binding sites is reduced (FIG. 8C).

Example 3

A. Materials and Methods

Plasmid constructs and generation of transgenic mice: A full length human MCIP1 cDNA encoding the exon 4 splice variant of hMCIP1 with an HA epitope tag from the human influenza hemaglutinin protein (hMCIP1-HA) was cloned 3' to a 5.5 kb segment of the α-myosin heavy chain promoter (α-MHC) and 5' to a 0.6 kb polyadenylation signal from the human growth hormone gene (FIG. 10), carried in the pBluescriptII SK+ vector (Stratagene, La Jolla, Calif.). The transgene was linearized and separated from prokaryotic sequences following digestion with NotI, and microinjected into fertilized oocytes from C57/BL6 mice, which were introduced into pseudopregnant females to generate lines of transgenic mice, using standard techniques. Animals were genotyped by Southern blot analysis of tail genomic DNA digested with EcoRI and probed with the hMCIP1 transgene. Animals carrying the α-MHC-hMCIP1 transgene were crossed with transgenic mice expressing a constitutively activated form of calcineurin, also under the control of the α-MHC promoter (Gulick et al., 1991) to produce doubly transgenic mice (α-MHC-hMCIP1×α-MHC-CnA*). MCIP expression plasmids were constructed in the pTARGET vector (Promega, Madison, Wis.) under the control of the cytomegalovirus (CMV) promoter. pCMV-hMCIP1 encodes an HA-tagged full length hMCIP1 (amino acids 1-197). pCMV-ΔhMCIP1 encodes an HA-tagged truncated hMCIP1 (amino acids 81 to 197). Other expression vectors and reporter genes have been previously described (Rothermel et al., 2000).

Cell culture studies: C2C12 myoblasts were maintained and transfected as previously described (Rothermel et al., 2000). Luciferase assays of whole cell extracts were performed as previously described (Rothermel et al., 2000). All results were corrected for variations in transfection efficiency by normalization to expression of a cotransfected pCMV-LacZ plasmid.

Intact animal studies: In addition to the genetic cross to α-MHC-CnA* animals, α-MHC-hMCIP1 transgenic mice and wild-type littermates were subjected to two independent stimuli known to provoke cardiac hypertrophy. Twelve-week old and 28-week old male mice were surgically implanted with a subcutaneous mini-osmotic pump (Alzet model 2001) that released isoproterenol in 0.9% NaCl at a rate of 28 mg per hour per 25 kg of body weight over a seven day period. Control pumps delivered a 0.9% NaCl solution. Hearts were harvested on day eight. The heart body weight ratio (htw/bw) of isoproterenol-treated, animals were compared to the mean htw/bw ratio of age matched saline-treated animals of the same genotype. For exercise-induced hypertrophy, 28-week old male animals were placed in individual cages where they had free access to a running wheel. The number of revolutions was monitored continuously for 28 days. The animals ran an average of 3 to 5 kilometers a day. The heart body weight ratios (htw/bw) of the exercised animals were compared to the mean htw/bw ratios of age-matched sedentary animals of the same genotype. A Wilcoxon rank sum test was used to determine statistically significant differences among treatment groups ($p<0.05$). All animal protocols were reviewed and approved by the appropriate institutional review boards.

RNA isolation and analysis: Total RNA was prepared from mouse heart and skeletal muscle using RNAzol (Life Technologies, Rockville, Md.) following the manufacturer's protocol. Northern blot analysis was performed with 20 mg of total RNA in each lane and probed in Ultrahyb (Ambion, Austin, Tex.) with a DNA fragment from the coding region of the human MCIP 1 transgene. RNA dot blots prepared with 2 mg of total RNA were probed with end-labeled oligonucleotides specific for mouse GAPDH, α-MHC, β-myosin heavy chain (b-MHC), α-skeletal actin or atrial natriuretic factor (ANF). Bound probes were detected on a Storm PhosphorImager (Molecular Dynamics, Sunnyvalle, Calif.) and quantified using ImageQuant (version 1.2).

Western blot analysis: Protein extracts were made by homogenizing frozen mouse heart and skeletal muscle in phosphate buffered saline plus 20% glycerol, 1% Triton-X 100 and 1 mM DTT using a polytron homogenizer (Kinematica, Lucerne, Switzerland). Samples were boiled in protein loading buffer containing SDS, then passed over glass wool to remove DNA. Extracts were prepared from tissue culture cells by lysis directly in protein loading buffer. Proteins were separated by SDS-PAGE. Epitope-tagged, transgene-derived proteins were detected using a primary rat anti-HA monoclonal antibody (Roche, Nutley, N.J.) and a horse radish peroxidase-tagged goat anti-rat secondary antibody (Bio-Rad, Hercules, Calif.).

Gross and histological analysis of hearts: Hearts were perfusion-fixed, embedded in paraffin and sectioned at 5 mm for histologic evaluation. Sections were stained with H&E and Masson's trichrome and photomicrographed using standard brightfield optics.

Transthoracic echocardiography: A 12 MHz probe (Hewlett Packard ) was applied to the shaved chest wall of mice sedated with Avertin (0.1*0.15 cc/mg body weight) and maneuvered to obtain a parasternal short axis view of the left ventricular cavity. Two-dimensional and M-mode echocardiography images were digitized and stored on an optical disc. Data was collected using a sweep speed of 150. Fractional shortening (FS) was calculated from the Left Ventricular End Diastolic Dimension (LVEDD) minus the Left Ventricular End Systolic Dimension (LVESD) divided by the LVEDD.

B. Results

Expression and function of the α-MHC-hMCIP1 transgene product: Three independent lines of α-MHC-hMCIP1 transgenic mice were established. In all three of these lines, both mRNA and protein products of the transgene were expressed in hearts of animals in the F1 generation. However, the protein produced by the transgene was 14 kD, much smaller than the predicted 24 kD full length hMCIP1 protein. Reverse transcriptase was used to generate a cDNA copy of the transgene product. The sequence of the cDNA demonstrated anomalous RNA splicing of the transgene from a cryptic splice donor site within the second non-coding exon of the (X-MHC gene to an acceptor site within the hMCIP1 cDNA (illustrated in FIG. 10), thereby removing the authentic translational initiation codon. Fortuitously, a stable but truncated protein product is initiated from an internal, in-frame methionine codon at amino acid 81. This truncated MCIP1 protein accumulates to measurable levels within the heart.

To test whether the 14 kD transgene product inhibits calcineurin activity, the C2C12 myoblast cell line was transfected with a luciferase reporter gene driven by a calcineurin-responsive IL-2 promoter (IL-2-Luc). Cotransfection of a constitutively active calcineurin expression vector (pCMV-CnA*) with either an empty control vector (pCMV-neo) or a plasmid expressing a full length hMCIP1 (pCMV-hMCIP1 ) demonstrated the ability of hMCIP1 to almost completely inhibit calcineurin induction of the IL-2-Luc reporter gene (FIG. 11). A plasmid expressing the truncated cDNA from the transgene (pCMV-ΔhMCIP1) was as effective an inhibitor of calcineurin as the wild-type, full-length MCIP1 protein (FIG. 11), verifying that the truncated 14 kD transgene product found in the hearts of the α-MHC-hMCIP1 mice is a powerful inhibitor of calcineurin activity. Western analysis comparing cardiac ΔhMCIP1 protein levels in the three founder lines showed comparable transgenic protein levels in L1 and L3, whereas in the L2 line, ΔhMCIP1 protein levels were two to three times higher (data not shown).

Strong cardiac-specific expression is initiated around the time of birth under the control of the α-MHC promoter (Gulick et al., 1991). The α-MHC-hMCIP1 transgene was inherited in a normal 1-to-1 Mendelian ratio in L1 and L3 with no evidence of deleterious effects in adult mice. Transmission of the L2 transgene was slightly reduced suggesting partial embryonic lethality, possibly due to embryonic expression of the transgene in this line. After birth however, L2 mice demonstrated normal growth and life spans. All subsequent experiments were done using animals from the L1 and L3 founder lines which performed comparably.

MCIP1 inhibits cardiac hypertrophy in a genetic model of cardiomyopathy. As reported previously (Molkentin et al., 1998), the inventors observed massive cardiac hypertrophy in α-MHC-CnA* transgenic mice. The extent of hypertrophic growth induced by the α-MHC-CnA* transgene was attenuated, however, by concomitant expression of the α-MHC-hMCIP1 transgene. Animals carrying the α-MHC-hMCIP1 transgene were viable and fertile, and exhibited no obvious cardiovascular abnormalities, with the exception of a mild (5-10%) reduction in cardiac mass compared to wild-type animals (Table 6). In mice bearing both the α-MHC-CnA* and α-MHC-hMCIP1 transgenes, the extent of cardiac hypertrophy was reduced to approximately 28% of the response noted with the α-MHC-CnA* transgene alone (Table 6). Using a Wilcoxon rank sum test for two groups of independent samples of observations the α-MHC-CnA*×α-MHC-hMCIP1 double transgenic mice developed significantly less cardiac hypertrophy than the α-MHC-CnA* transgenic mice (p<0.01). Expression of the hMCIP 1 transgene also prevented dilated cardiomyopathy induced by the CnA* transgene, as assessed by transthoractic echocardiography of a matched set of four male littermates (Table 7). Fractional shortening (FS) as an indication of the ejection volume of the heart was restored to wild-type levels in the α-MHC-hM-CIP1×α-MHC-CnA* double transgenic (FS=0.63) compared to the animal carrying the α-MHC-CnA* transgene alone, in which cardiac contractility was greatly impaired (FS=0.30). While the α-MHC-CnA* transgenic mice frequently suffer sudden death (Molkentin et al., 1998), no such early mortality was apparent in the α-MHC-hMCIP1×α-MHC-CnA* double transgenic mice. In addition to reducing the morphological and functional consequences of the α-MHC-CnA* transgene, hMCIP1 over-expression reduced the re-induction of the fetal program of gene expression that is characteristic of this and other models of cardiac hypertrophy. The levels of β-MHC, α-skeletal actin and ANF transcripts were elevated in the α-MHC-CnA* transgenic hearts compared to wild-type hearts. In the α-MHC-hMCIP1×α-MHC-CnA* double transgenic, both α-skeletal actin and ANF transcript levels were comparable to those found in wild-type hearts. Similarly, β-MHC expression, while greater than wild-type levels, was reduced relative to the levels detected in the hearts of α-MHC-CnA* mice.

TABLE 6

Heart Weight/Body Weight Ratios of Transgenic Mice

| wild type | α-MHC-hMCIP1 | α-MHC-CnA* | α-MHC-CnA* X α-MHC-hMCIP1 |
|---|---|---|---|
| 4.33 ± 0.09 (n = 16) | 4.10 ± 0.23 (n = 26) | 9.92 ± 1.06 (n = 5) | 5.69 ± 0.35 (n = 7) |

Data are calculated as heart weight/body weight (mg/g; mean ± SEM). The numbers of animals of each genotype that were tested are shown in parentheses. Wild type and α-MHC-hMCIP1 mice were 12-15 weeks of age. Median age of α-MHC-CnA* and α-MHC-hMCIP1 X α-MHC-CnA* mice was 12 weeks.

TABLE 7

Echocardiographic Assessment of the Left Ventricular Chamger

| Genotype | LVEDD† (cm) | LVESD (cm) | FS |
|---|---|---|---|
| wild type | 0.237 | 0.081 | 0.66 |
| α-MHC-hMCIP1 | 0.253 | 0.098 | 0.62 |
| α-MHC-CnA* | 0.479 | 0.339 | 0.30 |
| α-MHC-CnA*Xα-MHC-hMCIP1 | 0.298 | 0.113 | 0.63 |

Data collected from 20 week old male littermates.
†LVEDD, left centricular end-diastolic dimension; LVESD, left ventricular end-systolic dimension: FS, fractional shortening; FS = (LVEDD-LVESD)/LVEDD MCIP1 limits hypertrophic responses to other stimuli in intact animals. Calcineurin activation has been implicated in the progression of both pathological and adaptive cardiac hypertrophy (Eto et al., 2000). Chronic administration, over a seven day period, of the β-adrenergic receptor agonist isoproterenol using implantable osmotic minipumps produced a modest degree of cardiac hypertrophy in male wild-type animals, as described previously (Friddle et al., 2000) (22.8±1.95 percent increase in heart weight to body weight ratio). This hypertrophic response was diminished, though not abolished, by transgenic over-expression of hMCIP1 (9.4±0.87% increase) (FIG. 12). Similarly, physiological adaptive hypertrophy resulting from 28 days of nocturnal wheel running in wild-type male mice was reduced in animals carrying the α-MHC-hMCIP1 transgene (29.2±4.23% increase in wild-type versus 12.3±4.15% increase in the transgenic animals) (FIG. 12). Using a Wilcoxon rank sum test for two groups of independent samples of observations the α-MHC-hMCIP1 mice developed significantly less cardiac hypertrophy in response to either isoproterenol or exercise (p<0.05).

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EPO Patent No. 320 308
EPO Patent No. 0273085
U.S. Pat. No. 4,196,265
U.S. Pat. No. 4,554,101
U.S. Pat. No. 4,683,195
U.S. Pat. No. 4,683,202
U.S. Pat. No. 4,800,159
U.S. Pat. No. 4,873,191
U.S. Pat. No. 4,883,750
U.S. Pat. No. 5,279,721
U.S. Pat. No. 5,354,855
WO Patent No. 84/03564
WO Patent No. 90/07641
Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," *Mol. Cell. Biol.*, 7:2256, 1987a.
Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell*, 49:729, 1987b
Atchison and Perry, "Tandem Kappa Immunoglobulin Promoters are Equally Active in the Presence of the Kappa Enhancer: Implications for Model of Enhancer Function," *Cell*, 46:253, 1986.
Atchison and Perry, "The Role of the Kappa Enhancer and its Binding Factor NF-kappa B in the Developmental Regulation of Kappa Gene Transcription," *Cell*, 48:121, 1987.
Baichwal and Sugden, "Vectors for gene transfer derived from animal DNA viruses: Transient and stable expression of transferred genes", In: *Gene Transfer*, Kucherlapati R, ed., New York, Plenum Press, pp. 117-148, 1986.
Banerji et al., "Expression of a Beta-Globin Gene is Enhanced by Remote SV40 DNA Sequences," *Cell*, 27:299, 1981.
Banerji, Olson, and Schaffner, "A lymphocyte-specific cellular enhancer is located downstream of the joining region in immunoglobulin heavy-chain genes," *Cell*, 35:729, 1983.
Barany and Merrifield, The Peptides, Gross and Meienhofer, eds., Academic Press, New York, pp. 1-284, 1979.
Barnes K V, Cheng G, Dawson M M, Menick D R, "Cloning of cardiac, kidney, and brain promoters of the feline ncx1 gene," *J Biol Chem*, 272(17):11510-7, 1997.
Beals, Clipstone, Ho, Crabtree, *Genes Dev.*, 11:824-834, 1997.
Berkhout, Silverman, and Jeang, "Tat Trans-activates the Human Immunodeficiency Virus Through a Nascent RNA Target," *Cell*, 59:273, 1989.
Bhavsar P K, Brand N J, Yacoub M H, Barton P J R, "Isolation and characterization of the human cardiac troponin I gene (TNNI3)," *Genomics*, 35(1):11-23, 1996.
Blanar, Baldwin, Flavell, and Sharp, "A gamma-interferon-induced factor that binds the interferon response sequence of the MHC class I gene, H-2Kb," *EMBO J.*, 8:1139, 1989.
Bodine and Ley, "An enhancer element lies 3' to the human a gamma globin gene," *EMBO J.*, 6:2997, 1987.
Boshart, Weber, Jahn, Dorsch-Hasler, Fleckenstein, and Schaffner, "A very strong enhancer is located upstream of an immediate early gene of human cytomegalovirus," *Cell*, 41:521, 1985.
Bosze, Thiesen, and Charnay, "A transcriptional enhancer with specificity for erythroid cells is located in the long terminal repeat of the friend murine leukemia virus," *EMBO J.*, 5:1615, 1986.
Braddock, Chambers, Wilson, Esnouf, Adams, Kingsman, and Kingsman, "HIV-I Tat activates presynthesized RNA in the nucleus," *Cell*, 58:269, 1989.
Brinster et al., *Proc. Nat'l Acad. Sci. USA*, 82: 4438-4442, 1985.
Bulla and Siddiqui, "The hepatitis B virus enhancer modulates transcription of the hepatitis B virus surface-antigen gene from an internal location," *J. Virol.*, 62:1437, 1986.
Campbell and Villarreal, "Functional analysis of the individual enhancer core sequences of polyoma virus: cell-specific uncoupling of DNA replication from transcription," *Mol Cell. Biol.*, 8:1993, 1988.
Campere and Tilghman, "Postnatal repression of the alpha-fetoprotein gene is enhancer independent," *Genes and Dev.*, 3:537, 1989.
Campo, Spandidos, Lang, Wilkie, "Transcriptional control signals in the genome of bovine papilloma virus type 1," *Nature*, 303:77, 1983.
Capaldi et al., *Biochem. Biophys. Res. Comm.*, 76:425, 1977
Celander and Haseltine, "Glucocorticoid Regulation of Murine Leukemia Virus Transcription Elements is Specified by Determinants Within the Viral Enhancer Region," *J. Virology*, 61:269, 1987.
Celander, Hsu, and Haseltine, "Regulatory Elements Within the Murine Leukemia Virus Enhancer Regions Mediate Glucocorticoid Responsiveness," *J. Virology*, 62:1314, 1988.
Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.
Chang et al., "Foreign gene delivery and expression in hepatocytes using a hepatitis B virus vector", *Hepatology*, 14:124A, 1991.
Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.
Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc Natl. Acad Sci. U.S.A.,* 86:9114, 1989.

Timmerman, Clipstone, Ho, Northrop, Crabtree, *Nature,* 383:837-840, 1996.

Chen and Okayama, "High-efficiency transfection of mammalian cells by plasmid DNA", *Mol. Cell Biol.,* 7:2745-2752, 1987.

Chin, Olson, Richardson, Yang, Humphries, Shelton, Wu, Zhu, Bassel-Duby, Williams, "A calcineurin-dependent transcriptional pathway controls skeletal muscle fiber type," *Genes Dev.,* 12:2499-2509, 1998.

Choi, Chen, Kriegler, and Roninson, "An altered pattern of cross-resistance in multi-drug-resistant human cells results from spontaneous mutations in the mdr-1 (p-glycoprotein) gene," *Cell,* 53:519, 1988.

Clipstone and Crabtree, *Nature,* 357:695-697, 1992.

Coffin, Retroviridae and Their Replication. In: *Virology,* Fields et al., eds., Raven Press, New York, pp. 1437-1500, 1990.

Cohen, Walter, and Levinson, "A Repetitive Sequence Element 3' of the Human c-Ha-ras1 Gene Has Enhancer Activity," J. Cell. Physiol., 5:75, 1987.

Cook et al., "In vitro splicing of the ribosomal RNA precursor of Tetrahymena: involvement of a guanosine nucleotide in the excision of the intervening sequence," *Cell,* 27:487-496, 1981.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.,* 8:81, 1988.

Couch et al., "Immunization with types 4 and 7 adenovirus by selective infection of the intestinal tract," *Am. Rev. Resp. Dis.,* 88:394-403, 1963.

Coupar et al., "A general method for the construction of recombinant vaccinia virus expressing multiple foreign genes", *Gene,* 68:1-10, 1988.

Crabtree, "Generic signals and specific outcomes: signaling through Ca2+, calcineurin, and NF-AT," *Cell,* 96:611-614, 1999.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.,* 6:3745, 1987.

Culotta and Hamer, "Fine Mapping of a Mouse Metallothionein Gene Metal-Response Element," *Mol. Cell. Biol.,* 9:1376, 1989.

Dandolo, Blangy, and Kamen, "Regulation of Polyma Virus Transcription in Murine Embryonal Carcinoma Cells," *J. Virology,* 47:55, 1983.

De Villiers, Schaffner, Tyndall, Lupton, and Kamen, "Polyoma Virus DNA Replication Requires an Enhancer," *Nature,* 312:242, 1984.

Deschamps, Meijlink, and Verma, "Identification of a Transcriptional Enhancer Element Upstream From the Proto-Oncogene Fos," *Science,* 230:1174, 1985.

Ding, Price, Borg, Weinberg, Halloran, Lorell, "Pressure overload induces severe hypertrophy in mice treated with cyclosporine, an inhibitor of calcineurin," *Circ Res.,* 84:729-734, 1999.

Dubensky et al., "Direct transfection of viral and plasmid DNA into the liver or spleen of mice", *Proc. Nat'l Acad. Sci. USA,* 81:7529-7533, 1984.

Dunn, Burns, Michel, "Calcineurin is required for skeletal muscle hypertrophy," *J Biol Chem.,* 274:21908-21912, 1999.

Edbrooke, Burt, Cheshire, and Woo, "Identification of cis-acting sequences responsible for phorbol ester induction of human serum amyloid a gene expression via a nuclear-factor-kappa β-like transcription factor," *Mol. Cell. Biol.,* 9:1908, 1989.

Edlund, Walker, Barr, and Rutter, "Cell-specific expression of the rat insulin gene: evidence for role of two distinct 5' flanking elements," *Science,* 230:912, 1985.

Epstein, In *The Metabolic and MolecularBases of Inherited Disease: in Down Syndrome* (Trisomy 21), Scriver, Beaudet, Valle, (eds), 7th Ed., Vol. 1, pp. 749-794, McGraw-Hill, Inc., New York, 1995.

Eto, Yonekura, Sonoda, Arai, Sata, Sugiura, Takenaka, Gualberto, Hixon, Wagner, Aoyagi, *Circulation,* 101:2134-2137, 2000.

Fechheimer et al., "Transfection of mammalian cells with plasmid DNA by scrape loading and sonication loading", *Proc. Nat'l Acad. Sci. USA,* 84:8463-8467, 1987.

Feng and Holland, "HIV-I Tat Trans-Activation Requires the Loop Sequence Within Tar," *Nature,* 334:6178, 1988.

Ferkol et al., "Regulation of the phosphoenolpyruvate carboxykinase/human factor IX gene introduced into the livers of adult rats by receptor-mediated gene transfer", *FASEB J.,* 7:1081-1091, 1993.

Firak and Subramanian, "Minimal Transcription Enhancer of Simian Virus 40 is a 74-Base-Pair Sequence that Has Interacting Domains," *Mol. Cell. Biol.,* 6:3667, 1986.

Foecking and Hofstetter, "Powerful and Versatile Enhancer-Promoter Unit for Mammalian Expression Vectors," *Gene,* 45(1):101-105, 1986.

Forster and Symons, "Self-cleavage of plus and minus RNAs of a virusoid and a structural model for the active sites," *Cell,* 49:211-220, 1987.

Fraley et al., "Entrapment of a bacterial plasmid in phospholipid vesicles: Potential for gene transfer", *Proc. Nat'l Acad. Sci. USA,* 76:3348-3352, 1979.

Franz W M, et al.,"Characterization of a cardiac-selective and developmentally upregulated promoter in transgenic mice," *Cardioscience,* 5(4):235-43, 1994.

Freifelder, *Physical Biochemistry Applicationsto Biochemistry and Molecular Biology,* 2nd ed. Wm. Freeman and Co., New York, N.Y., 1982.

Friddle, Koga, Rubin, Bristow, *Proc. Natl. Acad. Sci. USA,* 97:6745-6750, 2000.

Friedmann, "Progress toward human gene therapy", *Science,* 244:1275-1281, 1989.

Fuentes, Pritchard, Estivill, "Genomic organization, alternative splicing, and expression patterns of the DSCR1 (Down syndrome candidate region 1) gene," *Genomics,* 44:358-361, 1997.

Fuentes, Pritchard, Planas, Bosch, Ferrer, Estivill, *Hum. Mol. Genet.,* 4:1935-1944, 1995.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell,* 49:357, 1987.

Gerlach et al., "Construction of a plant disease resistance gene from the satellite RNA of tobacco rinspot virus," *Nature (London),* 328:802-805, 1987.

Ghosh and Bachhawat, Targeting of Liposomes to Hepatocytes. In: *Liver Diseases, Targeted Diagnosisand Therapy Using SpecificReceptors and Ligands.* Wu et al., eds., Marcel Dekker, New York, pp. 87-104, 1991.

Ghosh-Choudhury et al., "Protein IX, a minor component of the human adenovirus capsid, is essential for the packaging of full-length genomes," *EMBO J.,* 6:1733-1739, 1987.

Gilles, Morris, Oi, and Tonegawa, "A tissue-specific transcription enhancer element is located in the major intron of a rearranged immunoglobulin heavy-chain gene," *Cell*, 33:717, 1983.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goding, 1986, In: *Monoclonal Antibodies: Principles and Practice*, 2d ed., Academic Press, Orlando, Fla., pp. 60-61, and 71-74, 1986.

Gomez-Foix et al., *J. Biol. Chem.*, 267:25129-25134, 1992.

Goodbourn and Maniatis, "Overlapping Positive and Negative Regulatory Domains of the Human β-Interferon Gene," *Proc. Natl. Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transfection, and cotransfection of suspension cell cultures", *Mol. Cell Biol.*, 5:1188-1190, 1985.

Gopal-Srivastava R, Haynes J I 2nd, Piatigorsky, J, "Regulation of the murine alpha B-crystallin/small heat shock protein gene in cardiac muscle," *Mol Cell Biol* 15(12): 7081--90, 1995.

Graef, Mermelstein, Stankunas, Neilson, Deisseroth, Tsien, Crabtree, *Nature*, 401:703-8, 1999.

Graham and Prevec, In: *Methods in Molecular Biology: Gene Transfer and Expression Protocol*, E. J. Murray, ed., Humana Press, Clifton, N.J., 7:109-128, 1991.

Graham and van der Eb, "A new technique for the assay of infectivity of human adenovirus 5 DNA", *Virology*, 52:456-467, 1973.

Grayson, Bassel-Duby, Williams, *J. Cell. Biochem.*, 70:366-375, 1998.

Grayson, Williams, Yu, Bassel-Duby, "Synergistic interactions between heterologous upstream activation elements and specific TATA sequences in a muscle-specific promoter," *Mol Cell Biol.*, 15:1870-1878, 1995.

Greene, Bohnlein, and Ballard, "HIV-1, and Normal T-Cell Growth: Transcriptional Strategies and Surprises," *Immunology Today*, 10:272, 1989.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector", *Seminar in Virology*, 3:237-252, 1992.

Gulick, Subramaniam, Neumann, Robbins, *J. Biol. Chem.*, 266:9180-9185, 1991.

Harland and Weintraub, "Translation of mammalian mRNA injected into Xenopus oocytes is specifically inhibited by antisense RNA", *J. Cell Biol.*, 101:1094-1099, 1985.

Harlow and Lane, Antibodies: A Laboratory manual, Cold Spring Harbor Laboratory, 1988.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activiation-Responsive Region of the Human Immunodeficiency Virus Type I Long Terminal Repeat," *J. Virology*, 62:673, 1988.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321: 249, 1986.

Hensel, Meichle, Pfizenmaier, and Kronke, "PMA-Responsive 5' Flanking Sequences of the Human TNF Gene," *Lymphokine Res.*, 8:347, 1989.

Hermonat and Muzycska, "Use of adenoassociated virus as a mammalian DNA cloning vector: Transduction of neomycin resistance into mammalian tissue culture cells", *Proc. Nat. Acad. Sci. USA*, 81:6466-6470, 1984.

Herr and Clarke, "The SV40 Enhancer is Composed of Multiple Functional Elements That Can Compensate for One Another," *Cell*, 45:461, 1986.

Hersdorffer et al., *DNA Cell Biol.*, 9:713-723, 1990.

Herz and Gerard, *Proc. Nat'l Acad. Sci. USA*, 90:2812-2816, 1993.

Hirochika, Browker, and Chow, "Enhancers and Trans-Acting E2 Transcriptional Factors of Papilloma Viruses," *J. Virol.*, 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.*, 10:1959,1990.

Ho, Gullberg, Chatila, *J. Exp. Med.*, 184:101-112, 1996a.

Ho, Hodge, Rooney, Glimcher, *Cell*, 85:973-983, 1996b.

Ho, Thomas, Timmerman, Li, Francke, Crabtree, *J. Biol. Chem.*, 270:19898-19907, 1995.

Hoey, Sun, Williamson, Xu, *Immunity*, 2:461-472, 1995.

Hogan et al. *Manipulating the Mouse Embryo* (Cold Spring Harbor Laboratory, Cold Spring Harbor, N.Y., 1986)

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Horwich, et al., "Synthesis of hepadnavirus particles that contain replication-defective duck hepatitis B virus genomes in cultured HuH7 cells", *J. Virol.*, 64:642-650, 1990.

Huang, Ostrowski, Berard, and Hagar, "Glucocorticoid regulation of the ha-musv p21 gene conferred by sequences from mouse mammary tumor virus," *Cell*, 27:245, 1981.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa, Chiu, and Karin, "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323: 555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Innis et al., *PCR Protocols,* Academic Press, Inc., San Diego Calif., 1990.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.*, 8:62, 1988.

Johnson et al., Peptide Turn Mimetics"IN: *Biotechnology And Pharmacy,* Pezzuto et al., eds., Chapman and Hall, New York, 1993.

Johnson, Wold, and Hauschka, "Muscle creatine kinase sequence elements regulating skeletal and cardiac muscle expression in transgenic mice," *Mol. Cell. Biol.*, 9:3393, 1989.

Jones and Shenk, *Cell,* 13:181-188, 1978.

Joyce, "RNA evolution and the origins of life," *Nature,* 338: 217-244, 1989.

Kadesch and Berg, "Effects of the Position of the Simian Virus 40 Enhancer on Expression of Multiple Transcription Units in a Single Plasmid," *Mol. Cell. Biol.*, 6:2593, 1986.

Kaneda et al., "Increased expression of DNA cointroduced with nuclear protein in adult rat liver", *Science,* 243:375-378, 1989.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Karlsson et al, *EMBO J.,* 5:2377-2385, 1986.

Kashishian, Howard, Loh, Gallatin, Hoekstra, Lai, *J. Biol. Chem.*, 273:27412-27419, 1998.

Katinka, Vasseur, Montreau, Yaniv, and Blangy, "Polyoma DNA Sequences Involved in the Control of Viral Gene Expression in Murine Embryonal Carcinoma Cells," *Nature,* 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell,* 20:393, 1980.

Kato et al., "Expression of hepatitis B virus surface antigen in adult rat liver", *J. Biol. Chem.*, 266:3361-3364, 1991.

Kawamoto, Makino, Niw, Sugiyama, Kimura, Anemura, Nakata, and Kakunaga, "Identification of the Human Beta-Actin Enhancer and its Binding Factor," *Mol. Cell. Biol.*, 8:267, 1988.

Kelly R, Alonso S, Tajbakhsh S, Cossu G, Buckingham M, "Myosin light chain 3F regulatory sequences confer regionalized cardiac and skeletal muscle expression in transgenic mice," *J Cell Biol,* 129(2):383-96, 1995.

Kiledjian, Su, Kadesch, "Identification and characterization of two functional domains within the murine heavy-chain enhancer," *Mol. Cell. Biol.*, 8:145, 1988.

Kim and Cook, "Three dimensional model of the active site of the self-splicing rRNA precursor or Tetrahymena," *Proc. Nat'l Acad. Sci. USA,* 84:8788-8792, 1987.

Kimura et al. "A 900 bp genomic region from the mouse dystrophin promoter directs lacZ reporter expression only to the right heart of transgenic mice," *Dev Growth Differ.* 39(3):257-65, 1997.

Kingsbury and Cunningham, Yeast Genetics and Molecular Meeting, Abstract , p. 98, Genetics Society of America, Bethesda, Md., 1998.

Klamut, Gangopadyhay, Worton, and Ray, "Molecular and Functional Analysis of the Muscle-Specific Promoter Region of the Duchenne Muscular Dystrophy Gene," *Mol. Cell. Biol.*, 10:193, 1990.

Klauck, Faux, Labudda, Langeberg, Jaken, Scott, "Coordination of three signaling enzymes by AKAP79, a mammalian scaffold protein," *Science,* 271:1589-1592, 1996.

Klee, Ren, Wang, *J. Biol. Chem.,* 273:13367-13370, 1998.

Klein et al., "High-velocity microprojectiles for delivering nucleic acids into living cells", *Nature,* 327:70-73, 1987.

Koch, Benoist, and Mathis, "Anatomy of a new β-cell-specific enhancer," *Mol. Cell. Biol.*, 9:303, 1989.

Kriegler and Botchan, "A retrovirus LTR contains a new type of eukaryotic regulatory element," In: *Eukaryotic Viral Vectors,* Gluzman (ed.), Cold Spring Harbor, Cold Spring Harbor Laboratory, NY, 1982.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler et al, "Promoter substitution and enhancer augmentation increases the penetrance of the sv40a gene to levels comparable to that of the harvey murine sarcoma virus ras gene in morphologic transformation," In: *Gene Expression,* Alan Liss (Ed.), Hamer and Rosenberg, New York, 1983.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes,* Van de Woude et al. (eds), Cold Spring Harbor, Cold Spring Harbor Laboratory, 1984.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell,* 53:45, 1988.

Kriegler, Perez, Hardy and Botchan, "Transformation mediated by the sv40 t antigens: separation of the overlapping sv40 early genes with a retroviral vector," *Cell,* 38:483, 1984.

Kuhl, De La Fuenta, Chaturvedi, Parinool, Ryals, Meyer, and Weissman, "Reversible Silencing of Enhancers by Sequences Derived From the Human IFN-alpha Promoter," *Cell,* 50:1057, 1987.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.,* 17:1121, 1989.

Kyte and Doolittle, *J. Mol Biol.,* 157(1):105-132, 1982.

Lai, Burnett, Wolosker, Blackshaw, Snyder, "Cain, a novel physiologic protein inhibitor of calcineurin," *J. Biol. Chem.,* 273:18325-18331, 1998.

LaPointe M C, Wu G, Garami M, Yang X P, Gardner D G, "Tissue-specific expression of the human brain natriuretic peptide gene in cardiac myocytes," *Hypertension* 27(3 Pt 2):715-22, 1996.

LaPointe, Wu, Greenberg, Gardner, *J. Biol. Chem.,* 263(19): 9075-8, 1988.

Larsen, Harney, and Moore, "Repression medaites cell-type-specific expression of the rat growth hormone gene," *Proc Natl. Acad. Sci. USA.*, 83:8283, 1986.

Laspia, Rice, and Mathews, "HIV-1 Tat protein increases transcriptional initiation and stabilizes elongation," *Cell*, 59:283, 1989.

Latimer, Berger, and Baumann, "Highly conserved upstream regions of the alpha..sub.1-antitrypsin gene in two mouse species govern liver-specific expression by different mechanisms," *Mol. Cell. Biol.*, 10:760, 1990.

Le Gal La Salle et al., "An adenovirus vector for gene transfer into neurons and glia in the brain," *Science*, 259:988-990, 1993.

Lee, Mulligan, Berg, and Ringold, "Glucocorticoids Regulate Expression of Dihydrofolate Reductase cDNA in Mouse Mammary Tumor Virus Chimaeric Plasmids," *Nature*, 294:228, 1981.

Levinson, Khoury, VanDeWoude, and Gruss, "Activation of SV40 Genome by 72-Base-Pair Tandem Repeats of Moloney Sarcoma Virus," *Nature*, 295:79, 1982.

Levrero et al., "Defective and nondefective adenovirus vectors for expressing foreign genes in vitro and in vivo," *Gene*, 101:195-202, 1991.

Lin, Cross, Halden, Dragos, Toledano, and Leonard, "Delineation of an enhancerlike positive regulatory element in the interleukin-2 receptor .alpha.-chain gene," *Mol. Cell. Biol.*, 10:850, 1990.

Liu, Liu, Borras, Chatila, Speck, *EMBO J.*, 16:143-153, 1997.

Loh, Shaw, Carew, Viola, Luo, Perrino, Rao, *J. Biol. Chem.*, 271:10884-10891, 1996.

Luo, Shaw, Raghavan, Aramburu, Garcia-Cozar, Perrino, Hogan, Rao, *Proc. Nat'l Acad. Sci. USA*, 93:8907-8912, 1996.

Luria, Gross, Horowitz, and Givol, "Promoter Enhancer Elements in the Rearranged Alpha-Chain Gene of the Human T-Cell Receptor," *EMBO J.*, 6:3307, 1987.

Lusky and Botchan, "Transient Replication of Bovine Papilloma Virus Type 1 Plasmids: cis and trans Requirements," *Proc Natl. Acad. Sci. U.S.A.*, 83:3609, 1986.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Macejak and Sarnow, "Internal initiation of translation mediated by the 5' leader of a cellular mRNA," *Nature*, 353:90-94, 1991.

Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.*, 80:5866, 1983.

Manipulating the Mouse Embryo: A Laboratory Manual, 2nd ed., Hogan et al., eds., Cold Spring Harbor Laboratory Press, 1994.

Mann et al., "Construction of a retrovirus packaging mutant and its use to produce helper-free defective retrovirus", *Cell*, 33:153-159, 1983.

Mao and Wiedmann, *J. Biol. Chem.*, 274:31102-31107, 1999.

Mao, Bonni, Xia, Nadal-Vicens, Greenberg, *Science*, 286: 785-790, 1999.

Marban, Kitakaze, Kusuoka, Porterfield, Yue, Chacko, *Proc. Nat'l Acad. Sci. USA*, 84:6005-6009,1987.

Markowitz et al., "A safe packaging line for gene transfer: Separating viral genes on two different plasmids," *J. Virol*, 62:1120-1124, 1988.

McNeall, Sanchez, Gray, Chesterman, and Sleigh, "Hyperinducible Gene Expression From a Metallotionein Promoter Containing Additional Metal-Responsive Elements," *Gene*, 76:81, 1989.

Merrifield, Science, 232: 341-347, 1986.

Mesaeli, Nakamura, Zvaritch, Dickie, Dziak, Krause, Opas, MacLennan, Michalak, *J. Cell Biol.*, 144:857-868, 1999.

Michel and Westhof, "Modeling of the three-dimensional architecture of group I catalytic introns based on comparative sequence analysis," *J. Mol. Biol.*, 216:585-610, 1990.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Miyazaki, Kanou, Murata, Ohmori, Niwa, Maeda, Yamamura, Seo, "Molecular cloning of a novel thyroid hormone-responsive gene, ZAKI-4, in human skin fibroblasts," *J Biol Chem.*, 271:14567-14571, 1996.

Molkentin, Lu, Antos, Markham, Richardson, Robbins, Grant, Olson, "A calcineurin-dependent transcriptional pathway for cardiac hypertrophy," *Cell*, 93:215-228, 1998.

Mordacq and Linzer, "Co-localization of Elements Required for Phorbol Ester Stimulation and Glucocorticoid Repression of Proliferin Gene Expression," *Genes and Dev.*, 3:760, 1989.

Moreau, Hen, Wasylyk, Everett, Gaub, and Chambon, "The SV40 base-repair repeat has a striking effect on gene expression both in sv40 and other chimeric recombinants," *Nucl. Acids Res.*, 9:6047, 1981.

Moss J B, Olson E N, Schwartz R J, "The myogenic regulatory factor MRF4 represses the cardiac alpha-actin promoter through a negative-acting N-terminal protein domain," *J Biol Chem*, 271(49):31688-94, 1996.

Mulligan, *Science*, 260:926-932, 1993.

Musaro A, McCullagh K J, Naya F J, Olson E N, Rosenthal N. IGF-1 induces skeletal myocyte hypertrophy through calcineurin in association with GATA-2 and NF-ATcl. Nature. 1999;400:581-585.

Musesing, Smith, and Capon, "Regulation of mRNA Accumulation by a Human Immunodeficiency Virus Trans-Activator Protein," *Cell*, 48:691, 1987.

Naya, Mercer, Shelton, Richardson, Williams, Olson, "Stimulation of slow skeletal muscle fiber gene expression by calcineurin in vivo," *J. Biol. Chem.*, 275:4545-4548, 2000.

Ng, Gunning, Liu, Leavitt, and Kedes, "Regulation of the Human Beta-Actin Promoter by Upstream and Intron Domains," *Nuc. Acids Res.*, 17:601, 1989.

Nicolas and Rubinstein, In: *Vectors: A survey of molecular-cloning vectors and their uses*, Rodriguez and Denhardt, eds., Stoneham: Butterworth, pp. 494-513, 1988.

Nicolau and Sene, "Liposome-mediated DNA transfer in eukaryotic cells", *Biochim. Biophys. Acta*, 721:185-190, 1982.

Nicolau et al, "Liposomes as carriers for in vivo gene transfer and expression," *Methods Enzymol.*, 149:157-176, 1987.

O'Keefe, Tamura, Kincaid, Tocci, O'Neill, *Nature*, 357:692-694, 1992.

Omitz, Hammer, Davison, Brinster, and Palmiter, "Promoter and enhancer elements from the rat elastase i gene function independently of each other and of heterologous enhancers," Mol. Cell. Biol. 7:3466, 1987.

Ondek, Sheppard, and Herr, "Discrete Elements Within the SV40 Enhancer Region Display Different Cell-Specific Enhancer Activities," *EMBO J.*, 6:1017, 1987. Palmiter et al. *Nature* 300:611, 1982.

Palmiter, Chen, and Brinster, "Differential regulation of metallothionein-thymidine kinase fusion genes in transgenic mice and their offspring," *Cell*, 29:701, 1982.

Paskind et al., "Dependence of moloney murine leukemia virus production on cell growth", *Virology*, 67:242-248, 1975.

Pech, Rao, Robbins, and Aaronson, "Functional identification of regulatory elements within the promoter region of platelet-derived growth factor 2, " *Mol. Cell. Biol.*, 9:396, 1989.

Pelletier and Sonenberg, "Internal initiation of translation of eukaryotic mRNA directed by a sequence derived from poliovirus RNA," *Nature*, 334:320-325, 1988.

Perales et al., "Gene transfer in vivo: Sustained expression and regulation of genes introduced into the liver by receptor-targeted uptake", *Proc. Nat'l Acad. Sci.* 91:4086-4090, 1994.

Perez-Stable and Constantini, "Roles of fetal γ-globin promoter elements and the adult β-globin 3' enhancer in the stage-specific expression of globin genes," *Mol. Cell. Biol.*, 10:1116, 1990.

Picard and Schaffner, "A Lymphocyte-Specific Enhancer in the Mouse Immunoglobulin Kappa Gene," *Nature*, 307:83, 1984.

Pignon, Vinatier, Fanen, Jonveaux, Tournilhac, Imbert, Rochant, Goossens, "Exhaustive analysis of the P53 gene coding sequence by denaturing gradient gel electrophoresis: application to the detection of point mutations in acute leukemias," *Hum. Mutant.*, 3: 126-132, 1994.

Pinkert, Omitz, Brinster, and Palmiter, "An albumin enhancer located 10 kb upstream functions along with its promoter to direct efficient, liver-specific expression in transgenic mice," *Genes and Dev.*, 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.*, 82:1020, 1985.

Porton, Zaller, Lieberson, and Eckhardt, "Immunoglobulin heavy-chain enhancer is required to maintain transfected .gamma.2a gene expression in a pre-b-cell line," *Mol. Cell. Biol.*, 10:1076, 1990.

Potter et al., "Enhancer-dependent expression of human k immunoglobulin genes introduced into mouse pre-B lymphocytes by electroporation," *Proc. Nat'l Acad. Sci. USA*, 81:7161-7165, 1984.

Queen and Baltimore, "Immunoglobulin Gene Transcription is Activated by Downstream Sequence Elements," *Cell*, 35:741, 1983.

Quinn, Farina, Gardner, Krutzsch, and Levens, "Multiple components are required for sequence recognition of the ap1 site in the gibbon ape leukemia virus enhancer," *Mol. Cell. Biol.*, 9:4713, 1989.

Racher et al., *Biotechnology Techniques*, 9:169-174, 1995.

Ragot et al., *Nature*, 361:647-650, 1993.

Rao, Luo, Hogan, "Transcription factors of the NFAT family: regulation and function," *Annu Rev Immunol.*, 15:707-747, 1997.

Redondo, Hata, Brocklehurst, and Krangel, "A T-Cell-Specific Transcriptional Enhancer Within the Human T-Cell Receptor .delta. Locus," *Science*, 247:1225, 1990.

Reinhold-Hurek & Shub, "Self-splicing introns in tRNA genes of widely divergent bacteria," *Nature*, 357:173-176, 1992.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.*, 9:3571, 1989.

Remington's Pharmaceutical Sciences, 15th Edition, Chapter 61, pages 1035-1038 and 1570-1580.

Renan, "Cancer genes: Current status, future prospects and applications in radiotherapy/oncology," *Radiother. Oncol.*, 19:197-218, 1990.

Resendez Jr., Wooden, and Lee, "Identification of highly conserved regulatory domains and protein-binding sites in the promoters of the rat and human genes encoding the stress-inducible 78-kilodalton glucose-regulated protein," *Mol. Cell. Biol.*, 8:4579, 1988.

Rich et al., "Development and analysis of recombinant adenoviruses for gene therapy of cystic fibrosis," *Hum. Gene Ther.*, 4:461-476, 1993.

Ridgeway, Mammalian Expression Vectors, In: *Vectors: A Survey of Molecular Cloning Vectors and Their Uses*, Rodriguez et al., eds., Stoneham: Butterworth, pp. 467-492, 1988.

Ripe, Lorenzen, Brenner, and Breindl, "Regulatory elements in the 5' flanking region and the first intron contribute to transcriptional control of the mouse alpha-1-type collagen gene," *Mol. Cell. Biol.*, 9:2224, 1989.

Rippe et al., "DNA-mediated gene transfer into adult rat hepatocytes in primary culture," *Mol. Cell Biol.*, 10:689-695, 1990.

Rittling, Coutinho, Amarm, and Kolbe, "AP-1/jun-binding Sites Mediate Serum Inducibility of the Human Vimentin Promoter," *Nuc. Acids Res.*, 17:1619, 1989.

Robbins and Swain, "C-myc protooncogene modulates cardiac hypertrophic growth in transgenic mice," *Am J Physiol.*, 262:H590-597, 1992.

Rosen, Sodroski, and Haseltine, "The location of cis-acting regulatory sequences in the human t-cell lymphotropic virus type III (HTLV-111/LAV) long terminal repeat," *Cell*, 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant .alpha. 1-antitrypsin gene to the lung epithelium in vivo," *Science*, 252:431-434,1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143-155,1992.

Rothermel, Vega, Yang, Wu, Bassel-Duby, Williams, "A protein encoded within the Down syndrome critical region is enriched in striated muscles and inhibits calcineurin signaling," *J Biol Chem.*, 275:8719-8725, 2000.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA*, 86:9079-9083, 1989.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Sambrook et al., In: *Molecular Cloning: A Laboratory Manual*, 2d Ed., Cold Spring Harbor Laboratory Press, Cold Spring Harbor, N.Y., 1989.

Sarver, et al, "Ribozymes as potential anti-HIV-1 therapeutic agents," *Science*, 247:1222-1225, 1990.

Satake, Furukawa, and Ito, "Biological activities of oligonucleotides spanning the f9 point mutation within the enhancer region of polyoma virus DNA," *J. Virology*, 62:970, 1988.

Scanlon et al., "Ribozyme-mediated cleavages of c-fos mRNA reduce gene expression of DNA synthesis enzymes and metallothionein," *Proc. Nat'l Acad. Sci. USA*, 88:10591-10595, 1991.

Schaffner, Schirm, Muller-Baden, Wever, and Schaffner, "Redundancy of Information in Enhancers as a Principle of Mammalian Transcription Control," *J. Mol. Biol.*, 201:81, 1988.

Schena, Shalon, Heller, Chai, Brown, Davis, "Parallel human genome analysis: microarray-based expression monitoring of 1000 genes," *Proc Natl Acad Sci USA*, 93:10614-10619, 1996.

Schiaffino and Reggiani, *Physiol. Rev.*, 76:371-423, 1996.

Searle, Stuart, and Palmiter, "Building a metal-responsive promoter with synthetic regulatory elements," *Mol. Cell. Biol.*, 5:1480, 1985.

Seidman and Seidman, *Basic Res. Cardiol.*, 93:13-16, 1998.

Semsarian, Wu, Ju, Marciniec, Yeoh, Allen, Harvey, Graham, "Skeletal muscle hypertrophy is mediated by a Ca2+-dependent calcineurin signalling pathway," *Nature*, 400:576-581, 1999.

Sharp and Marciniak, "HIV Tar: an RNA Enhancer?," *Cell*, 59:229, 1989.

Shaul and Ben-Levy, "Multiple Nuclear Proteins in Liver Cells are Bound to Hepatitis B Virus Enhancer Element and its Upstream Sequences," *EMBO J.*, 6:1913, 1987.

Sherman, Basta, Moore, Brown, and Ting, "Class II Box Consensus Sequences in the HLA-DR.alpha. Gene: Transcriptional Function and Interaction with Nuclear Proteins," *Mol. Cell. Biol.*, 9:50, 1989.

Shibasaki, Price, Milan, McKeon, *Nature*, 382:370-373, 1996.

Sigal, Dumont, Durette, Siekierka, Peterson, Rich, Dunlap, Staruch, Melino, Koprak, et al., *J. Exp. Med.*, 173:619-628, 1991.

Sleigh and Lockett, "SV40 Enhancer Activation During Retinoic-Acid-Induced Differentiation of F9 Embryonal Carcinoma Cells," *J. EMBO*, 4:3831, 1985.

Spalholz, Yang, and Howley, "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J.*, 2:1193, 1983.

Stephens and Hentschel, "The Bovine Papilloma Virus Genome and its Uses as a Eukaryotic Vector," *Biochem. J.*, 248:1, 1987.

Stewart and Young, Solid Phase Peptide Synthesis, 2d. ed., Pierce Chemical Co., 1984.

Stratford-Perricaudet and Perricaudet, Gene transfer into animals: the promise of adenovirus. In: *Human Gene Transfer*, O. Cohen-Haguenauer et al., eds., John Libbey Eurotext, France, pp. 51-61, 1991.

Stratford-Perricaudet et al., "Evaluation of the transfer and expression in mice of an enzyme-encoding gene using a human adenovirus vector", *Hum. Gene. Ther.*, 1:241-256, 1990.

Stuart, Searle, and Palmiter, "Identification of Multiple Metal Regulatory Elements in Mouse Metallothionein-I Promoter by Assaying Synthetic Sequences," *Nature*, 317:828, 1985.

Sullivan and Peterlin, "Transcriptional Enhancers in the HLA-DQ Subregion," *Mol. Cell. Biol.*, 7:3315, 1987.

Sun, Youn, Loh, Stolow, He, Liu, "Cabin 1, a negative regulator for calcineurin signaling in T lymphocytes," *Immunity*, 8:703-711, 1998.

Sussman, Lim, Gude, Taigen, Olson, Robbins, Colbert, Gualberto, Wieczorek, Molkentin, "Prevention of cardiac hypertrophy in mice by calcineurin inhibition," *Science*, 281:1690-1693, 1998.

Swartzendruber and Lehman, "Neoplastic Differentiation: Interaction of Simian Virus 40 and Polyoma Virus with Murine Teratocarcinoma Cells," *J. Cell. Physiology*, 85:179, 1975.

Takebe, Seiki, Fujisawa, Hoy, Yokota, Arai, Yoshida, and Arai, "SR.alpha. Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466, 1988.

Tam et al., *J. Am. Chem. Soc.*, 105:6442, 1983.

Tavernier, Gheysen, Duerinck, Can Der Heyden, and Fiers, "Deletion Mapping of the Inducible Promoter of Human IFN-beta Gene," *Nature*, 301:634, 1983.

Taylor and Kingston, "E1A Trans-Activation of Human HSP70 Gene Promoter Substitution Mutants is Independent of the Composition of Upstream and TATA Elements," *Mol. Cell. Biol.*, 10:176, 1990.

Taylor and Kingston, "Factor Substitution in a Human HSP70 Gene Promoter: TATA-Dependent and TATA-Independent Interactions," *Mol. Cell. Biol.*, 10:165, 1990.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.*, 264:15160, 1989.

Temin, Retrovirus vectors for gene transfer: Efficient integration into and expression of exogenous DNA in vertebrate cell genome. In: *Gene Transfer*, Kucherlapati R, ed., New York, Plenun Press, pp. 149-188, 1986. *The Qiagenologist, Application Protocols*, 3rd edition, published by Qiagen, Inc., Chatsworth, Calif.;

Thiesen, Bosze, Henry, and Charnay, "A DNA Element Responsible for the Different Tissue Specificities of Friend and Moloney Retroviral Enhancers," *J. Virology*, 62:614, 1988.

Top et al., "Immunization with live types 7 and 4 adenovirus vaccines. II. Antibody response and protective effect against acute respiratory disease due to adenovirus type 7," *J. Infect. Dis.*, 124:155-160, 1971.

Treisman, "Transient Accumulation of c-fos RNA Following Serum Stimulation Requires a Conserved 5' Element and c-fos 3' Sequences," *Cell*, 42:889, 1986.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.*, 9:4759, 1989.

Tronche, Rollier, Herbomel, Bach, Cereghini, Weiss, and Yaniv, "Anatomy of the Rat Albumin Promoter," *Mol. Biol. Med.*, 7:173, 1990.

Trudel and Constantini, "A 3' Enhancer Contributes to the Stage-Specific Expression of the human Beta-Globin Gene," *Genes and Dev.*, 6:954, 1987.

Tur-Kaspa et al., "Use of electroporation to introduce biologically active foreign genes into primary rat hepatocytes", *Mol. Cell Biol.*, 6:716-718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Vannice and Levinson, "Properties of the Human Hepatitis B Virus Enhancer: Position Effects and Cell-Type Nonspecificity," *J. Virology,* 62:1305, 1988.

Varmus et al., *Cell,* 25:23-36, 1981.

Vasseur, Kress, Montreau, and Blangy, "Isolation and Characterization of Polyoma Virus Mutants Able to Develop in Multipotential Murine Embryonal Carcinoma Cells," *Proc Natl. Acad. Sci. U.S.A.,* 77:1068, 1980.

Wagner et al., *Proc. Nat'l Acad. Sci. USA* 87(9):3410-3414, 1990.

Wang et al., *Biochimica et Biophysica Acta* 888(2):225-36, 1986.

Wang, Pathan, Ethell, Krajewski, Yamaguchi, Shibasaki, McKeon, Bobo, Franke, Reed, "Ca2+-induced apoptosis through calcineurin dephosphorylation of BAD," *Science,* 284:339-343, 1999.

Weber, DeVilliers, and Schaffner, "An SV40 'Enhancer Trap' Incorporates Exogenous Enhancers or Generates Enhancers From its Own Sequences," *Cell,* 36:983, 1984.

Weinberger et al. "Localization of a Repressive Sequence Contributing to B-cell Specificity in the Immunoglobulin Heavy-Chain Enhancer," *Mol. Cell. Biol.,* 8:988, 1984.

Winoto and Baltimore, "αβ-lineage-specific Expression of the α T-Cell Receptor Gene by Nearby Silencers," *Cell,* 59:649, 1989.

Wong et al., "Appearance of b-lactamase activity in animal cells upon liposome mediated gene transfer", *Gene,* 10:87-94, 1980.

Wu and Wu, "Evidence for targeted gene delivery to HepG2 hepatoma cells in vitro " *Biochemistry,* 27:887-892, 1988.

Wu and Wu, "Receptor-mediated in vitro gene transfections by a soluble DNA carrier system", *J. Biol. Chem.,* 262: 4429-4432, 1987.

Wu and Wu, *Adv. Drug Delivery Rev.,* 12:159-167, 1993.

Wu et al., *Genomics,* 4:560, 1989.

Wu, Naya, McKinsey, Mercer, Shelton, Chin, Simard, Michel, Bassel-Duby, Olson, Williams, "MEF2 responds to multiple calcium-regulated signals in the control of skeletal muscle fiber type," *EMBO J.,* 19:1963-1973, 2000.

Yamauchi-Takihara, Sole, Liew, Ing, Liew, "Characterization of human cardiac myosin heavy chain genes," *Proc. Nat'l Acad. Sci. USA,* 86(10):3504-8, 1989.

Yang et al., In vivo and in vitro gene transfer to mammalian somatic cells by particle bombardment. *Proc. Nat'l Acad. Sci. USA,* 87:9568-9572, 1990.

Yang, Bassel-Duby, Williams, *Mol. Cell. Biol.,* 17:5236-5243, 1997.

Youn, Sun, Prywes, Liu, *Science,* 286:790-793, 1999.

Yutzey, Kline, and Konieczny, "An Internal Regulatory Element Controls Troponin I Gene Expression," *Mol. Cell. Biol.,* 9:1397, 1989.

Zelenin et al., "High-velocity mechanical DNA transfer of the chloramphenicol acetyltransferase gene into rodent liver, kidney and mammary gland cells in organ explants and in vivo", *FEBS Lett.,* 280:94-96, 1991.

Zhang, Kowal, Rusnak, Sikkink, Olson, Victor, "Failure of calcineurin inhibitors to prevent pressure-overload left ventricular hypertrophy in rats," *Circ Res.,* 84:722-728, 1999.

Zhuo, Zhang, Son, Mansuy, Sobel, Seidman, Kandel, *Proc. Nat'l Acad. Sci. USA,* 96:4650-4655, 1999.

Ziober BL, Kramer RH, "Identification and characterization of the cell type-specific and developmentally regulated alpha7 integrin gene promoter," *J Biol Chem,* 271(37): 22915-22, 1996.

What is claimed is:

1. A method of modulating muscle cell growth in striated muscle cells in a human subject comprising:
   (a) identifying a human subject in need of striated muscle cell growth modulation;
   (b) assaying a small molecule for its ability to modulate Muscle Selective Calcineurin Interacting Protein (MCIP1) expression; and
   (c) administering said small molecule which is shown to modulate MCIP1 expression in step (b) to said human subject,
   whereby administration of said small molecule results in modulation of striated muscle cell growth by modulating said MCIP1 expression in said human subject.

2. The method of claim 1, wherein said small molecule is an agonist of muscle cell growth.

3. The method of claim 1, wherein said small molecule is an antagonist of muscle cell growth.

4. The method of claim 1, further comprising administering to said human subject a pharmaceutical agent used to treat cardiac disease.

* * * * *

UNITED STATES PATENT AND TRADEMARK OFFICE
CERTIFICATE OF CORRECTION

| | |
|---|---|
| PATENT NO. | : 7,629,308 B2 |
| APPLICATION NO. | : 09/782953 |
| DATED | : December 8, 2009 |
| INVENTOR(S) | : Williams et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this
Eleventh Day of January, 2011

David J. Kappos
*Director of the United States Patent and Trademark Office*

```
                             SEQUENCE LISTING

<160> NUMBER OF SEQ ID NOS: 27

<210> SEQ ID NO 1
<211> LENGTH: 599
<212> TYPE: DNA
<213> ORGANISM: Mus musculus

<400> SEQUENCE: 1
gaggtgcaaa ggaacctcca gcttgggctt gactgagaga gcgagtcgtt cgttaagcgt      60
ctgccccgtg aaaaagcaga atgatttag ggactttagc tacaatttta gctccctgat     120
tgcttgtgtg gcaaacgatg atgtcttcag cgaaagtgag accagggcca aatttgaatc     180
cctcttcaga acatatgaca aggacaccac cttccagtat tttaagagct tcaaacgtgt     240
ccggataaac ttcagcaacc ccttatctgc agccgatgcc aggctgcggc tgcacaagac     300
cgagttcctg gggaaggaaa tgaagttgta ttttgctcag actttacaca taggaagttc     360
acacctggct ccgccaatcc cgacaaacag ttcctcatct cccctccggc ctctcctccc     420
gttggctgga aacaagtaga agatgccacc cccgtcataa attacgatct tttatatgcc     480
atctccaagc tggggccagg agagaagtat gaactgcatg cagcgacaga caccactccc     540
agtgtggtgg tccacgtgtg tgagagtgac caagagaatg aggaggaaga ggaagagat     599

<210> SEQ ID NO 2
```

<211> LENGTH: 597
<212> TYPE: DNA
<213> ORGANISM: Mus musculus
<220> FEATURE:
<221> NAME/KEY: CDS
<222> LOCATION: (1)..(594)

<400> SEQUENCE: 2

```
atg gag gag gtg gat ctg cag gac ctg ccg agc gcc acc atc gcc tgc      48
Met Glu Glu Val Asp Leu Gln Asp Leu Pro Ser Ala Thr Ile Ala Cys
 1               5                  10                  15 cac ctg gac ccg cgc gtg ttc gtg gac ggc ctg tgc cgg gcc aaa ttt      96
His Leu Asp Pro Arg Val Phe Val Asp Gly Leu Cys Arg Ala Lys Phe
             20                  25                  30 gaa tcc ctc ttc aga aca tat gac aag gac acc acc ttc cag tat ttt     144
Glu Ser Leu Phe Arg Thr Tyr Asp Lys Asp Thr Thr Phe Gln Tyr Phe
         35                  40                  45 aag agc ttc aaa cgt gtc cgg ata aac ttc agc aac ccc tta tct gca     192
Lys Ser Phe Lys Arg Val Arg Ile Asn Phe Ser Asn Pro Leu Ser Ala
     50                  55                  60 gcc gat gcc agg ctg cgg ctg cac aag acc gag ttc ctg ggg aag gaa     240
Ala Asp Ala Arg Leu Arg Leu His Lys Thr Glu Phe Leu Gly Lys Glu
 65                  70                  75                  80 atg aag ttg tat ttt gct cag act tta cac ata gga agt tca cac ctg     288
Met Lys Leu Tyr Phe Ala Gln Thr Leu His Ile Gly Ser Ser His Leu
                 85                  90                  95 gct ccg ccc aat ccc gac aaa cag ttc ctc atc tcc cct ccg gcc tct     336
Ala Pro Pro Asn Pro Asp Lys Gln Phe Leu Ile Ser Pro Pro Ala Ser
            100                 105                 110 cct ccc gtt ggc tgg aaa caa gta gaa gat gcc acc ccc gtc ata aat     384
Pro Pro Val Gly Trp Lys Gln Val Glu Asp Ala Thr Pro Val Ile Asn
        115                 120                 125 tac gat ctt tta tat gcc atc tcc aag ctg ggg cca gga gag aag tat     432
Tyr Asp Leu Leu Tyr Ala Ile Ser Lys Leu Gly Pro Gly Glu Lys Tyr
    130                 135                 140 gaa ctg cat gca gcg aca gac ccc act ccc agt gtg gtg gtc cac gtg     480
Glu Leu His Ala Ala Thr Asp Pro Thr Pro Ser Val Val Val His Val
145                 150                 155                 160 tgt gag agt gac caa gag aat gag gag gaa gag gaa gag atg gag aga     528
Cys Glu Ser Asp Gln Glu Asn Glu Glu Glu Glu Glu Glu Met Glu Arg
                165                 170                 175 atg aag aga ccc aag ccc aaa atc atc cag aca cgg aga ccg gag tac     576
Met Lys Arg Pro Lys Pro Lys Ile Ile Gln Thr Arg Arg Pro Glu Tyr
            180                 185                 190 aca ccg atc cac ctt agc tga                                         597
Thr Pro Ile His Leu Ser
        195
```

<210> SEQ ID NO 3
<211> LENGTH: 198
<212> TYPE: PRT
<213> ORGANISM: Mus musculus

<400> SEQUENCE: 3

```
Met Glu Glu Val Asp Leu Gln Asp Leu Pro Ser Ala Thr Ile Ala Cys
 1               5                  10                  15

His Leu Asp Pro Arg Val Phe Val Asp Gly Leu Cys Arg Ala Lys Phe
             20                  25                  30

Glu Ser Leu Phe Arg Thr Tyr Asp Lys Asp Thr Thr Phe Gln Tyr Phe
         35                  40                  45

Lys Ser Phe Lys Arg Val Arg Ile Asn Phe Ser Asn Pro Leu Ser Ala
```

-continued

```
                50                  55                  60
Ala Asp Ala Arg Leu Arg Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
                100                 105                 110

Pro Pro Val Gly Trp Lys Gln Val Glu Asp Ala Thr Pro Val Ile Asn
            115                 120                 125

Tyr Asp Leu Leu Tyr Ala Ile Ser Lys Leu Gly Pro Gly Glu Lys Tyr
130                 135                 140

Glu Leu His Ala Ala Thr Asp Pro Thr Pro Ser Val Val His Val
145                 150                 155                 160

Cys Glu Ser Asp Gln Glu Asn Glu Glu Glu Glu Met Glu Arg
                165                 170                 175

Met Lys Arg Pro Lys Pro Lys Ile Ile Gln Thr Arg Arg Pro Glu Tyr
            180                 185                 190

Thr Pro Ile His Leu Ser
            195
```

<210> SEQ ID NO 4
<211> LENGTH: 198
<212> TYPE: PRT
<213> ORGANISM: Mus musculus

<400> SEQUENCE: 4

```
Met Glu Glu Val Asp Leu Gln Asp Leu Pro Ser Ala Thr Ile Ala Cys
 1               5                  10                  15

His Leu Asp Pro Arg Val Phe Val Asp Gly Leu Cys Arg Ala Lys Phe
                20                  25                  30

Glu Ser Leu Phe Arg Thr Tyr Asp Lys Asp Thr Thr Phe Gln Tyr Phe
             35                  40                  45

Lys Ser Phe Lys Arg Val Arg Ile Asn Phe Ser Asn Pro Leu Ser Ala
 50                  55                  60

Ala Asp Ala Arg Leu Arg Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
                100                 105                 110

Pro Pro Val Gly Trp Lys Gln Val Glu Asp Ala Thr Pro Val Ile Asn
            115                 120                 125

Tyr Asp Leu Leu Tyr Ala Ile Ser Lys Leu Gly Pro Gly Glu Lys Tyr
130                 135                 140

Glu Leu His Ala Ala Thr Asp Pro Thr Pro Ser Val Val His Val
145                 150                 155                 160

Cys Glu Ser Asp Gln Glu Asn Glu Glu Glu Glu Met Glu Arg
                165                 170                 175

Met Lys Arg Pro Lys Pro Lys Ile Ile Gln Thr Arg Arg Pro Glu Tyr
            180                 185                 190

Thr Pro Ile His Leu Ser
            195
```

<210> SEQ ID NO 5
<211> LENGTH: 597

```
<212> TYPE: DNA
<213> ORGANISM: Mus musculus
<220> FEATURE:
<221> NAME/KEY: CDS
<222> LOCATION: (1)..(594)

<400> SEQUENCE: 5 atg gat ttt agg gac ttt agc tac aat ttt agc tcc ctg att gct tgt        48
Met Asp Phe Arg Asp Phe Ser Tyr Asn Phe Ser Ser Leu Ile Ala Cys
 1               5                  10                  15 gtg gca aac gat gat gtc ttc agc gaa agt gag acc agg gcc aaa ttt        96
Val Ala Asn Asp Asp Val Phe Ser Glu Ser Glu Thr Arg Ala Lys Phe
            20                  25                  30 gaa tcc ctc ttc aga aca tat gac aag gac acc acc ttc cag tat ttt       144
Glu Ser Leu Phe Arg Thr Tyr Asp Lys Asp Thr Thr Phe Gln Tyr Phe
        35                  40                  45 aag agc ttc aaa cgt gtc cgg ata aac ttc agc aac ccc tta tct gca       192
Lys Ser Phe Lys Arg Val Arg Ile Asn Phe Ser Asn Pro Leu Ser Ala
    50                  55                  60 gcc gat gcc agg ctg cgg ctg cac aag acc gag ttc ctg ggg aag gaa       240
Ala Asp Ala Arg Leu Arg Leu His Lys Thr Glu Phe Leu Gly Lys Glu
65                  70                  75                  80 atg aag ttg tat ttt gct cag act tta cac ata gga agt tca cac ctg       288
Met Lys Leu Tyr Phe Ala Gln Thr Leu His Ile Gly Ser Ser His Leu
                85                  90                  95 gct ccg ccc aat ccc gac aaa cag ttc ctc atc tcc cct ccg gcc tct       336
Ala Pro Pro Asn Pro Asp Lys Gln Phe Leu Ile Ser Pro Pro Ala Ser
            100                 105                 110 cct ccc gtt ggc tgg aaa caa gta gaa gat gcc acc ccc gtc ata aat       384
Pro Pro Val Gly Trp Lys Gln Val Glu Asp Ala Thr Pro Val Ile Asn
        115                 120                 125 tac gat ctt tta tat gcc atc tcc aag ctg ggg cca gga gag aag tat       432
Tyr Asp Leu Leu Tyr Ala Ile Ser Lys Leu Gly Pro Gly Glu Lys Tyr
    130                 135                 140 gaa ctg cat gca gcg aca gac ccc act ccc agt gtg gtg gtc cac gtg       480
Glu Leu His Ala Ala Thr Asp Pro Thr Pro Ser Val Val Val His Val
145                 150                 155                 160 tgt gag agt gac caa gag aat gag gag gaa gag gaa gag atg gag aga       528
Cys Glu Ser Asp Gln Glu Asn Glu Glu Glu Glu Glu Glu Met Glu Arg
                165                 170                 175 atg aag aga ccc aag ccc aaa atc atc cag aca cgg aga ccg gag tac       576
Met Lys Arg Pro Lys Pro Lys Ile Ile Gln Thr Arg Arg Pro Glu Tyr
            180                 185                 190 aca ccg atc cac ctt agc tga                                          597
Thr Pro Ile His Leu Ser
        195

<210> SEQ ID NO 6
<211> LENGTH: 198
<212> TYPE: PRT
<213> ORGANISM: Mus musculus

<400> SEQUENCE: 6

Met Asp Phe Arg Asp Phe Ser Tyr Asn Phe Ser Ser Leu Ile Ala Cys
 1               5                  10                  15

Val Ala Asn Asp Asp Val Phe Ser Glu Ser Glu Thr Arg Ala Lys Phe
            20                  25                  30

Glu Ser Leu Phe Arg Thr Tyr Asp Lys Asp Thr Thr Phe Gln Tyr Phe
        35                  40                  45

Lys Ser Phe Lys Arg Val Arg Ile Asn Phe Ser Asn Pro Leu Ser Ala
    50                  55                  60
```

```
Ala Asp Ala Arg Leu Arg Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Pro Thr Pro Ser Val Val Val His Val
145                 150                 155                 160

Cys Glu Ser Asp Gln Glu Asn Glu Glu Glu Glu Glu Met Glu Arg
                165                 170                 175

Met Lys Arg Pro Lys Pro Lys Ile Ile Gln Thr Arg Arg Pro Glu Tyr
            180                 185                 190

Thr Pro Ile His Leu Ser
        195

<210> SEQ ID NO 7
<211> LENGTH: 198
<212> TYPE: PRT
<213> ORGANISM: Mus musculus

<400> SEQUENCE: 7

Met Asp Phe Arg Asp Phe Ser Tyr Asn Phe Ser Ser Leu Ile Ala Cys
  1               5                  10                  15

Val Ala Asn Asp Val Phe Ser Glu Ser Glu Thr Arg Ala Lys Phe
                 20                  25                  30

Glu Ser Leu Phe Arg Thr Tyr Asp Lys Asp Thr Thr Phe Gln Tyr Phe
             35                  40                  45

Lys Ser Phe Lys Arg Val Arg Ile Asn Phe Ser Asn Pro Leu Ser Ala
     50                  55                  60

Ala Asp Ala Arg Leu Arg Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Pro Thr Pro Ser Val Val Val His Val
145                 150                 155                 160

Cys Glu Ser Asp Gln Glu Asn Glu Glu Glu Glu Glu Met Glu Arg
                165                 170                 175

Met Lys Arg Pro Lys Pro Lys Ile Ile Gln Thr Arg Arg Pro Glu Tyr
            180                 185                 190

Thr Pro Ile His Leu Ser
        195

<210> SEQ ID NO 8
<211> LENGTH: 594
<212> TYPE: DNA
```

<213> ORGANISM: Mus musculus
<220> FEATURE:
<221> NAME/KEY: CDS
<222> LOCATION: (1)..(591)

<400> SEQUENCE: 8

```
atg cca gcc cct agc atg gac tgt gat gtt tcc act ctg gtc gcc tgt      48
Met Pro Ala Pro Ser Met Asp Cys Asp Val Ser Thr Leu Val Ala Cys
 1               5                  10                  15 gtg gtg gat gtg gag gtc ttt acc aat cag gag gtt aag gaa aaa ttc      96
Val Val Asp Val Glu Val Phe Thr Asn Gln Glu Val Lys Glu Lys Phe
             20                  25                  30 gag gga ctg ttc cgg acc tat gat gaa tgt gtg acg ttc cag ctg ttt     144
Glu Gly Leu Phe Arg Thr Tyr Asp Glu Cys Val Thr Phe Gln Leu Phe
         35                  40                  45 aag agt ttc cga cgg gtt cga ata aat ttc agc cat ccc aaa tct gca     192
Lys Ser Phe Arg Arg Val Arg Ile Asn Phe Ser His Pro Lys Ser Ala
     50                  55                  60 gcc cgt gcc cgg ata gag ctt cat gag act cag ttc aga ggg aag aag     240
Ala Arg Ala Arg Ile Glu Leu His Glu Thr Gln Phe Arg Gly Lys Lys
 65                  70                  75                  80 cta aaa ctc tac ttc gcc cag gtc cag acc cca gag aca gat gga gac     288
Leu Lys Leu Tyr Phe Ala Gln Val Gln Thr Pro Glu Thr Asp Gly Asp
                 85                  90                  95 aaa ctg cat ttg gca cct cca cag cct gcc aaa cag ttc ctc atc tca     336
Lys Leu His Leu Ala Pro Pro Gln Pro Ala Lys Gln Phe Leu Ile Ser
            100                 105                 110 ccc cct tca tct cct cct gtt ggc tgg aag cct atc agc gat gcc aca     384
Pro Pro Ser Ser Pro Pro Val Gly Trp Lys Pro Ile Ser Asp Ala Thr
        115                 120                 125 cca gtc ctc aac tat gac ctt ctt tat gct gtg gcc aaa cta gga cca     432
Pro Val Leu Asn Tyr Asp Leu Leu Tyr Ala Val Ala Lys Leu Gly Pro
    130                 135                 140 gga gag aaa tat gag ctg cac gct gga act gag tct aca ccg agc gtc     480
Gly Glu Lys Tyr Glu Leu His Ala Gly Thr Glu Ser Thr Pro Ser Val
145                 150                 155                 160 gtg gtg cat gtg tgt gac agc gac atg gag gag gag gag gac cca aag     528
Val Val His Val Cys Asp Ser Asp Met Glu Glu Glu Glu Asp Pro Lys
                165                 170                 175 act tcc ccc aag cca aaa atc att cag acc cgg cgt ccg ggc ttg cca     576
Thr Ser Pro Lys Pro Lys Ile Ile Gln Thr Arg Arg Pro Gly Leu Pro
            180                 185                 190 ccc tcc gtg tcc aac tga                                              594
Pro Ser Val Ser Asn
        195
```

<210> SEQ ID NO 9
<211> LENGTH: 197
<212> TYPE: PRT
<213> ORGANISM: Mus musculus

<400> SEQUENCE: 9

```
Met Pro Ala Pro Ser Met Asp Cys Asp Val Ser Thr Leu Val Ala Cys
 1               5                  10                  15

Val Val Asp Val Glu Val Phe Thr Asn Gln Glu Val Lys Glu Lys Phe
             20                  25                  30

Glu Gly Leu Phe Arg Thr Tyr Asp Glu Cys Val Thr Phe Gln Leu Phe
         35                  40                  45

Lys Ser Phe Arg Arg Val Arg Ile Asn Phe Ser His Pro Lys Ser Ala
     50                  55                  60
```

Ala Arg Ala Arg Ile Glu Leu His Glu Thr Gln Phe Arg Gly Lys Lys
65                  70                  75                  80

Leu Lys Leu Tyr Phe Ala Gln Val Gln Thr Pro Glu Thr Asp Gly Asp
                85                  90                  95

Lys Leu His Leu Ala Pro Pro Gln Pro Ala Lys Gln Phe Leu Ile Ser
            100                 105                 110

Pro Pro Ser Ser Pro Pro Val Gly Trp Lys Pro Ile Ser Asp Ala Thr
        115                 120                 125

Pro Val Leu Asn Tyr Asp Leu Leu Tyr Ala Val Ala Lys Leu Gly Pro
    130                 135                 140

Gly Glu Lys Tyr Glu Leu His Ala Gly Thr Glu Ser Thr Pro Ser Val
145                 150                 155                 160

Val Val His Val Cys Asp Ser Asp Met Glu Glu Glu Asp Pro Lys
                165                 170                 175

Thr Ser Pro Lys Pro Lys Ile Ile Gln Thr Arg Arg Pro Gly Leu Pro
                180                 185                 190

Pro Ser Val Ser Asn
        195

<210> SEQ ID NO 10
<211> LENGTH: 197
<212> TYPE: PRT
<213> ORGANISM: Mus musculus

<400> SEQUENCE: 10

Met Pro Ala Pro Ser Met Asp Cys Asp Val Ser Thr Leu Val Ala Cys
1               5                   10                  15

Val Val Asp Val Glu Val Phe Thr Asn Gln Glu Val Lys Glu Lys Phe
                20                  25                  30

Glu Gly Leu Phe Arg Thr Tyr Asp Glu Cys Val Thr Phe Gln Leu Phe
            35                  40                  45

Lys Ser Phe Arg Arg Val Arg Ile Asn Phe Ser His Pro Lys Ser Ala
        50                  55                  60

Ala Arg Ala Arg Ile Glu Leu His Glu Thr Gln Phe Arg Gly Lys Lys
65                  70                  75                  80

Leu Lys Leu Tyr Phe Ala Gln Val Gln Thr Pro Glu Thr Asp Gly Asp
                85                  90                  95

Lys Leu His Leu Ala Pro Pro Gln Pro Ala Lys Gln Phe Leu Ile Ser
            100                 105                 110

Pro Pro Ser Ser Pro Pro Val Gly Trp Lys Pro Ile Ser Asp Ala Thr
        115                 120                 125

Pro Val Leu Asn Tyr Asp Leu Leu Tyr Ala Val Ala Lys Leu Gly Pro
    130                 135                 140

Gly Glu Lys Tyr Glu Leu His Ala Gly Thr Glu Ser Thr Pro Ser Val
145                 150                 155                 160

Val Val His Val Cys Asp Ser Asp Met Glu Glu Glu Asp Pro Lys
                165                 170                 175

Thr Ser Pro Lys Pro Lys Ile Ile Gln Thr Arg Arg Pro Gly Leu Pro
                180                 185                 190

Pro Ser Val Ser Asn
        195

<210> SEQ ID NO 11
<211> LENGTH: 2331
<212> TYPE: DNA
<213> ORGANISM: Homo sapiens

```
<220> FEATURE:
<221> NAME/KEY: CDS
<222> LOCATION: (144)..(734)

<400> SEQUENCE: 11
tttttttttc cccagggagt gggggctggc ccttactgct ttataagcac cagctcaaga    60
aggaacctac agcctcttgg aaaggaatct cactagggc ttgactgcgt gggtctgtag   120
cgctttcact gtaagaaagc aag atg cat ttt aga aac ttt aac tac agt ttt  173
                         Met His Phe Arg Asn Phe Asn Tyr Ser Phe
                           1               5                  10 agc tcc ctg att gcc tgt gtg gca aac agt gat atc ttc agc gaa agt    221
Ser Ser Leu Ile Ala Cys Val Ala Asn Ser Asp Ile Phe Ser Glu Ser
                 15                  20                  25 gaa acc agg gcc aaa ttt gag tcc ctc ttt agg acg tat gac aag gac    269
Glu Thr Arg Ala Lys Phe Glu Ser Leu Phe Arg Thr Tyr Asp Lys Asp
         30                  35                  40 atc acc ttt cag tat ttt aag agc ttc aaa cga gtc aga ata aac ttc    317
Ile Thr Phe Gln Tyr Phe Lys Ser Phe Lys Arg Val Arg Ile Asn Phe
     45                  50                  55 agc aac ccc ttc tcc gca gca gat gcc agg ctc cag ctg cat aag act    365
Ser Asn Pro Phe Ser Ala Ala Asp Ala Arg Leu Gln Leu His Lys Thr
 60                  65                  70 gag ttt ctg gga aag gaa atg aag tta tat ttt gct cag acc tta cac    413
Glu Phe Leu Gly Lys Glu Met Lys Leu Tyr Phe Ala Gln Thr Leu His
 75                  80                  85                  90 ata gga agc tca cac ctg gct ccg cca aat cca gac aag cag ttt ctg    461
Ile Gly Ser Ser His Leu Ala Pro Pro Asn Pro Asp Lys Gln Phe Leu
             95                 100                 105 atc tcc cct ccc gcc tct ccg cca gtg gga tgg aaa caa gtg gaa gat    509
Ile Ser Pro Pro Ala Ser Pro Pro Val Gly Trp Lys Gln Val Glu Asp
        110                 115                 120 gcg acc cca gtc ata aac tat gat ctc tta tat gcc atc tcc aag ctg    557
Ala Thr Pro Val Ile Asn Tyr Asp Leu Leu Tyr Ala Ile Ser Lys Leu
    125                 130                 135 ggg cca ggg gaa aag tat gaa ttg cac gca gcg act gac acc act ccc    605
Gly Pro Gly Glu Lys Tyr Glu Leu His Ala Ala Thr Asp Thr Thr Pro
140                 145                 150 agc gtg gtg gtc cat gta tgt gag agt gat caa gag aag gag gaa gaa    653
Ser Val Val Val His Val Cys Glu Ser Asp Gln Glu Lys Glu Glu Glu
155                 160                 165                 170 gag gaa atg gaa aga atg agg aga cct aag cca aaa att atc cag acc    701
Glu Glu Met Glu Arg Met Arg Arg Pro Lys Pro Lys Ile Ile Gln Thr
                175                 180                 185 agg agg ccg gag tac acg ccg atc cac ctc agc tgaactggca cgcgacgagg  754
Arg Arg Pro Glu Tyr Thr Pro Ile His Leu Ser
            190                 195 acgcattcca aatcatactc acgggaggaa tctttactg tggaggtggc tggtcacgac    814
ttcttcggag gtggcagccg agatcggggt ggcagaaatc ccagttcatg ttgctcagaa   874
gagaatcaag gccgtgtccc cttgttctaa tgctgcacac cagttactgt tcatggcacc   934
cgggaatgac ttgggccaat cactgagttt gtggtgatcg cacaaggaca tttgggactg   994
tcttgagaaa acagataatg atagtgtttt gtacttgttc ttttctggta ggttctgtct  1054
gtgccaaggg caggttgatc agtgagctca ggagagagct tcctgtttct aagtggcctg  1114
caggggccac tctctactgg taggaagagg taccacagga agccgcctag tgcagagagg  1174
ttgtgaaaac agcagcaatg caatgtggaa attgtagcgt ttccttttct ccctcatgtt  1234
ctcatgtttg tgcatgtata ttactgattt acaagactaa cctttgttcg tatataaagt  1294
```

```
tacaccgttg ttgttttaca tcttttggga agccaggaaa gcgtttggaa aacgtatcac    1354
ctttcccaga ttctcggatt ctcgactctt tgcaacagca cttgcttgcg gaactcttcc    1414
tggaatgcat tcactcagca tccccaaccg tgcaacgtgt aacttgtgct tttgcaaaag    1474
aagttgatct gaaattcctc tgtagaattt agcttataca attcagagaa tagcagtttc    1534
actgccaact tttagtgggt gagaaatttt agtttaggtg tttgggatcg gacctcagtt    1594
tctgttgttt cttttatgtg gtggtttcta tacatgaatc atagccaaaa actttttggg    1654
aaactgttgg ttgagatagt tggttctttt acccccacgaa gacatcaaga tacacttgta   1714
aataaagctg atagcatata ttcatacctg ttgtacactt gggtgaaaag tatggcagtg    1774
ggagactaag atgtattaac ctacctgtga atcatatgtt gtaggaaaag ctgttcccat    1834
gtctaacagg acttgaattc aaagcatgtc aagtggatag tagatctgtg gcgatatgag    1894
agggatgcag tgcctttccc cattcattcc tgatggaatt gttatactag gttaacattt    1954 gtaattttt tctagttgta atgtgtatgt ctggtaaata ggtattatat tttggcctta    2014
caataccgta acaatgtttg tcattttgaa atacttaatg ccaagtaaca atgcatgctt    2074
tggaaatttg gaagatggtt ttattctttg agaagcaaat atgtttgcat taaatgcttt    2134
gattgttcat atcaagaaat tgattgaacg ttctcaaacc ctgtttacgg tacttggtaa    2194
gagggagccg gtttgggaga gaccattgca tcgctgtcca agtgtttctt gttaagtgct    2254
tttaaactgg agaggctaac ctcaaaatac ttttttttaac tgcattctat aataaatggg    2314
cacagtatgc tccttac                                                  2331
```

<210> SEQ ID NO 12
<211> LENGTH: 197
<212> TYPE: PRT
<213> ORGANISM: Homo sapiens

<400> SEQUENCE: 12

```
Met His Phe Arg Asn Phe Asn Tyr Ser Phe Ser Ser Leu Ile Ala Cys
  1               5                  10                  15

Val Ala Asn Ser Asp Ile Phe Ser Glu Ser Thr Arg Ala Lys Phe
             20                  25                  30

Glu Ser Leu Phe Arg Thr Tyr Asp Lys Asp Ile Thr Phe Gln Tyr Phe
         35                  40                  45

Lys Ser Phe Lys Arg Val Arg Ile Asn Phe Ser Asn Pro Phe Ser Ala
     50                  55                  60

Ala Asp Ala Arg Leu Gln Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Thr Thr Pro Ser Val Val His Val
145                 150                 155                 160

Cys Glu Ser Asp Gln Glu Lys Glu Glu Glu Met Glu Arg Met
                165                 170                 175

Arg Arg Pro Lys Pro Lys Ile Ile Gln Thr Arg Arg Pro Glu Tyr Thr
```

```
                180                 185                 190

Pro Ile His Leu Ser
        195

<210> SEQ ID NO 13
<211> LENGTH: 197
<212> TYPE: PRT
<213> ORGANISM: Homo sapiens

<400> SEQUENCE: 13

Met His Phe Arg Asn Phe Asn Tyr Ser Phe Ser Ser Leu Ile Ala Cys
1               5                   10                  15

Val Ala Asn Ser Asp Ile Phe Ser Glu Ser Glu Thr Arg Ala Lys Phe
            20                  25                  30

Glu Ser Leu Phe Arg Thr Tyr Asp Lys Asp Ile Thr Phe Gln Tyr Phe
        35                  40                  45

Lys Ser Phe Lys Arg Val Arg Ile Asn Phe Ser Asn Pro Phe Ser Ala
    50                  55                  60

Ala Asp Ala Arg Leu Gln Leu His Lys Thr Glu Phe Leu Gly Lys Glu
65                  70                  75                  80

Met Lys Leu Tyr Phe Ala Gln Thr Leu His Ile Gly Ser Ser His Leu
                85                  90                  95

Ala Pro Pro Asn Pro Asp Lys Gln Phe Leu Ile Ser Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Thr Thr Pro Ser Val Val Val His Val
145                 150                 155                 160

Cys Glu Ser Asp Gln Glu Lys Glu Glu Glu Met Glu Arg Met
                165                 170                 175

Arg Arg Pro Lys Pro Lys Ile Ile Gln Thr Arg Arg Pro Glu Tyr Thr
            180                 185                 190

Pro Ile His Leu Ser
        195

<210> SEQ ID NO 14
<211> LENGTH: 2212
<212> TYPE: DNA
<213> ORGANISM: Homo sapiens
<220> FEATURE:
<221> NAME/KEY: CDS
<222> LOCATION: (25)..(615)

<400> SEQUENCE: 14
gactggagct tcattgactg cgag atg gag gag gtg gac ctg cag gac ctg         51
                          Met Glu Glu Val Asp Leu Gln Asp Leu
                            1               5 ccc agc gcc acc atc gcc tgt cac ctg gac ccg cgc gtg ttc gtg gac        99
Pro Ser Ala Thr Ile Ala Cys His Leu Asp Pro Arg Val Phe Val Asp
 10                  15                  20                  25 ggc ctg tgc cgg gcc aaa ttt gag tcc ctc ttt agg acg tat gac aag       147
Gly Leu Cys Arg Ala Lys Phe Glu Ser Leu Phe Arg Thr Tyr Asp Lys
                 30                  35                  40 gac atc acc ttt cag tat ttt aag agc ttc aaa cga gtc aga ata aac       195
Asp Ile Thr Phe Gln Tyr Phe Lys Ser Phe Lys Arg Val Arg Ile Asn
             45                  50                  55
```

```
ttc agc aac ccc ttc tcc gca gca gat gcc agg ctc cag ctg cat aag      243
Phe Ser Asn Pro Phe Ser Ala Ala Asp Ala Arg Leu Gln Leu His Lys
         60                  65                  70 act gag ttt ctg gga aag gaa atg aag tta tat ttt gct cag acc tta      291
Thr Glu Phe Leu Gly Lys Glu Met Lys Leu Tyr Phe Ala Gln Thr Leu
 75                  80                  85 cac ata gga agc tca cac ctg gct ccg cca aat cca gac aag cag ttt      339
His Ile Gly Ser Ser His Leu Ala Pro Pro Asn Pro Asp Lys Gln Phe
 90                  95                 100                 105 ctg atc tcc cct ccc gcc tct ccg cca gtg gga tgg aaa caa gtg gaa      387
Leu Ile Ser Pro Pro Ala Ser Pro Pro Val Gly Trp Lys Gln Val Glu
                110                 115                 120 gat gcg acc cca gtc ata aac tat gat ctc tta tat gcc atc tcc aag      435
Asp Ala Thr Pro Val Ile Asn Tyr Asp Leu Leu Tyr Ala Ile Ser Lys
                125                 130                 135 ctg ggg cca ggg gaa aag tat gaa ttg cac gca gcg act gac acc act      483
Leu Gly Pro Gly Glu Lys Tyr Glu Leu His Ala Ala Thr Asp Thr Thr
                140                 145                 150 ccc agc gtg gtg gtc cat gta tgt gag agt gat caa gag aag gag gaa      531
Pro Ser Val Val Val His Val Cys Glu Ser Asp Gln Glu Lys Glu Glu
        155                 160                 165 gaa gag gaa atg gaa aga atg agg aga cct aag cca aaa att atc cag      579
Glu Glu Glu Met Glu Arg Met Arg Arg Pro Lys Pro Lys Ile Ile Gln
170                 175                 180                 185 acc agg agg ccg gag tac acg ccg atc cac ctc agc tgaactggca           625
Thr Arg Arg Pro Glu Tyr Thr Pro Ile His Leu Ser
                190                 195 cgcgacgagg acgcattcca aatcatactc acgggaggaa tcttttactg tggaggtggc    685
tggtcacgac ttcttcggag gtggcagccg agatcggggt ggcagaaatc ccagttcatg    745
ttgctcagaa gagaatcaag gccgtgtccc cttgttctaa tgctgcacac cagttactgt    805
tcatggcacc cgggaatgac ttgggccaat cactgagttt gtggtgatcg cacaaggaca    865
tttgggactg tcttgagaaa acagataatg atagtgtttt gtacttgttc ttttctggta    925
ggttctgtct gtgccaaggg caggttgatc agtgagctca ggagagagct tcctgtttct    985
aagtggcctg caggggccac tctctactgg taggaagagg taccacagga agccgcctag   1045
tgcagagagg ttgtgaaaac agcagcaatg caatgtggaa attgtagcgt ttcctttctt   1105
ccctcatgtt ctcatgtttg tgcatgtata ttactgattt acaagactaa cctttgttcg   1165
tatataaagt tacaccgttg ttgttttaca tcttttggga agccaggaaa gcgtttggaa   1225
aacgtatcac ctttcccaga ttctcggatt ctcgactctt tgcaacagca cttgcttgcg   1285
gaactcttcc tggaatgcat tcactcagca tccccaaccg tgcaacgtgt aacttgtgct   1345
tttgcaaaag aagttgatct gaaattcctc tgtagaattt agcttataca attcagagaa   1405
tagcagtttc actgccaact tttagtgggt gagaaatttt agtttaggtg tttgggatcg   1465
gacctcagtt tctgttgttt cttttatgtg gtggtttcta tacatgaatc atagccaaaa   1525
acttttttgg aaactgttgg ttgagatagt tggttctttt accccacgaa gacatcaaga   1585
tacacttgta aataaagctg atagcatata ttcatacctg ttgtacactt gggtgaaaag   1645
tatggcagtg ggagactaag atgtattaac ctacctgtga atcatatgtt gtaggaaaag   1705
ctgttcccat gtctaacagg acttgaattc aaagcatgtc aagtggatag tagatctgtg   1765
gcgatatgag agggatgcag tgcctttccc cattcattcc tgatggaatt gttatactag   1825
gttaacattt gtaattttttt tctagttgta atgtgtatgt ctggtaaata ggtattatat   1885
tttggcctta caataccgta acaatgtttg tcattttgaa atacttaatg ccaagtaaca   1945
```

```
atgcatgctt tggaaatttg gaagatggtt ttattctttg agaagcaaat atgtttgcat    2005
taaatgcttt gattgttcat atcaagaaat tgattgaacg ttctcaaacc ctgtttacgg    2065
tacttggtaa gagggagccg gtttgggaga gaccattgca tcgctgtcca agtgtttctt    2125
gttaagtgct tttaaactgg agaggctaac ctcaaaatac ttttttttaac tgcattctat   2185 aataaatggg cacagtatgc tccttac                                        2212
```

```
<210> SEQ ID NO 15
<211> LENGTH: 197
<212> TYPE: PRT
<213> ORGANISM: Homo sapiens

<400> SEQUENCE: 15
```

| Met | Glu | Glu | Val | Asp | Leu | Gln | Asp | Leu | Pro | Ser | Ala | Thr | Ile | Ala | Cys |
|---|---|---|---|---|---|---|---|---|---|---|---|---|---|---|---|
| 1 | | | | 5 | | | | | 10 | | | | | 15 | |

| His | Leu | Asp | Pro | Arg | Val | Phe | Val | Asp | Gly | Leu | Cys | Arg | Ala | Lys | Phe |
| | | | 20 | | | | | 25 | | | | | 30 | | |

| Glu | Ser | Leu | Phe | Arg | Thr | Tyr | Asp | Lys | Asp | Ile | Thr | Phe | Gln | Tyr | Phe |
| | | | 35 | | | | | 40 | | | | | 45 | | |

| Lys | Ser | Phe | Lys | Arg | Val | Arg | Ile | Asn | Phe | Ser | Asn | Pro | Phe | Ser | Ala |
| | 50 | | | | | 55 | | | | | 60 | | | | |

| Ala | Asp | Ala | Arg | Leu | Gln | Leu | His | Lys | Thr | Glu | Phe | Leu | Gly | Lys | Glu |
| 65 | | | | | 70 | | | | | 75 | | | | | 80 |

| Met | Lys | Leu | Tyr | Phe | Ala | Gln | Thr | Leu | His | Ile | Gly | Ser | Ser | His | Leu |
| | | | | 85 | | | | | 90 | | | | | 95 | |

| Ala | Pro | Pro | Asn | Pro | Asp | Lys | Gln | Phe | Leu | Ile | Ser | Pro | Pro | Ala | Ser |
| | | | 100 | | | | | 105 | | | | | 110 | | |

| Pro | Pro | Val | Gly | Trp | Lys | Gln | Val | Glu | Asp | Ala | Thr | Pro | Val | Ile | Asn |
| | | | 115 | | | | | 120 | | | | | 125 | | |

| Tyr | Asp | Leu | Leu | Tyr | Ala | Ile | Ser | Lys | Leu | Gly | Pro | Gly | Glu | Lys | Tyr |
| | | 130 | | | | | 135 | | | | | 140 | | | |

| Glu | Leu | His | Ala | Ala | Thr | Asp | Thr | Thr | Pro | Ser | Val | Val | Val | His | Val |
| 145 | | | | | 150 | | | | | 155 | | | | | 160 |

| Cys | Glu | Ser | Asp | Gln | Glu | Lys | Glu | Glu | Glu | Glu | Met | Glu | Arg | Met |
| | | | | 165 | | | | | 170 | | | | | 175 |

| Arg | Arg | Pro | Lys | Pro | Lys | Ile | Ile | Gln | Thr | Arg | Arg | Pro | Glu | Tyr | Thr |
| | | | 180 | | | | | 185 | | | | | 190 | | |

| Pro | Ile | His | Leu | Ser |
| | | | 195 | |

```
<210> SEQ ID NO 16
<211> LENGTH: 197
<212> TYPE: PRT
<213> ORGANISM: Homo sapiens

<400> SEQUENCE: 16
```

| Met | Glu | Glu | Val | Asp | Leu | Gln | Asp | Leu | Pro | Ser | Ala | Thr | Ile | Ala | Cys |
|---|---|---|---|---|---|---|---|---|---|---|---|---|---|---|---|
| 1 | | | | 5 | | | | | 10 | | | | | 15 | |

| His | Leu | Asp | Pro | Arg | Val | Phe | Val | Asp | Gly | Leu | Cys | Arg | Ala | Lys | Phe |
| | | | 20 | | | | | 25 | | | | | 30 | | |

| Glu | Ser | Leu | Phe | Arg | Thr | Tyr | Asp | Lys | Asp | Ile | Thr | Phe | Gln | Tyr | Phe |
| | | | 35 | | | | | 40 | | | | | 45 | | |

| Lys | Ser | Phe | Lys | Arg | Val | Arg | Ile | Asn | Phe | Ser | Asn | Pro | Phe | Ser | Ala |
| | 50 | | | | | 55 | | | | | 60 | | | | |

| Ala | Asp | Ala | Arg | Leu | Gln | Leu | His | Lys | Thr | Glu | Phe | Leu | Gly | Lys | Glu |

```
                65                  70                  75                  80
Met Lys Leu Tyr Phe Ala Gln Thr Leu His Ile Gly Ser Ser His Leu
                    85                  90                  95

Ala Pro Pro Asn Pro Asp Lys Gln Phe Leu Ile Ser Pro Pro Ala Ser
                100                 105                 110

Pro Pro Val Gly Trp Lys Gln Val Glu Asp Ala Thr Pro Val Ile Asn
                115                 120                 125

Tyr Asp Leu Leu Tyr Ala Ile Ser Lys Leu Gly Pro Gly Glu Lys Tyr
            130                 135                 140

Glu Leu His Ala Ala Thr Asp Thr Thr Pro Ser Val Val His Val
145                 150                 155                 160

Cys Glu Ser Asp Gln Glu Lys Glu Glu Glu Met Glu Arg Met
                165                 170                 175

Arg Arg Pro Lys Pro Lys Ile Ile Gln Thr Arg Arg Pro Glu Tyr Thr
                180                 185                 190

Pro Ile His Leu Ser
            195

<210> SEQ ID NO 17
<211> LENGTH: 3184
<212> TYPE: DNA
<213> ORGANISM: Homo sapiens
<220> FEATURE:
<221> NAME/KEY: CDS
<222> LOCATION: (205)..(780)

<400> SEQUENCE: 17
ctctgctgtg ctgcctcaaa cgcggagggc tgcgtgcagt gggagcgggc tccaggagcc     60
cgagcctcca gccgtcctca gagcaaggca gcaccgagcg ctggccacag caatatccat    120
ctggaagctc ttcccttcac tcccaactct gaggttgcct aactctttat taaaaattca    180 gaaggggaa tgccagcccc tagc atg gac tgt gat gtt tcc act ctg gtt        231
                          Met Asp Cys Asp Val Ser Thr Leu Val
                            1               5 gcc tgt gtg gtg gat gtc gag gtc ttt acc aat cag gag gtt aag gaa      279
Ala Cys Val Val Asp Val Glu Val Phe Thr Asn Gln Glu Val Lys Glu
 10                  15                  20                  25 aaa ttt ggg gga ctg ttt cgg act tat gat gac tgt gtg acg ttc cag      327
Lys Phe Gly Gly Leu Phe Arg Thr Tyr Asp Asp Cys Val Thr Phe Gln
                 30                  35                  40 cta ttt aag agt ttc aga cgt gtc cgt ata aac ttc agc aat cct aaa      375
Leu Phe Lys Ser Phe Arg Arg Val Arg Ile Asn Phe Ser Asn Pro Lys
             45                  50                  55 tct gca gcc cga gct agg ata gag ctt cat gaa acc caa ttc aga ggg      423
Ser Ala Ala Arg Ala Arg Ile Glu Leu His Glu Thr Gln Phe Arg Gly
         60                  65                  70 aaa aaa tta aag ctc tac ttt gca cag gtt cag act cca gag aca gat      471
Lys Lys Leu Lys Leu Tyr Phe Ala Gln Val Gln Thr Pro Glu Thr Asp
     75                  80                  85 gga gac aaa ctg cac ttg gct cca ccc cag cct gcc aaa cag ttt ctc      519
Gly Asp Lys Leu His Leu Ala Pro Pro Gln Pro Ala Lys Gln Phe Leu
 90                  95                 100                 105 atc tcg ccc cct tcc tcc cca cct gtt agc tgg cag ccc atc aac gat      567
Ile Ser Pro Pro Ser Ser Pro Pro Val Ser Trp Gln Pro Ile Asn Asp
                110                 115                 120 gcc acg cca gtc ctc aac tat gac ctc ctc tat gct gtg gcc aaa cta      615
Ala Thr Pro Val Leu Asn Tyr Asp Leu Leu Tyr Ala Val Ala Lys Leu
                125                 130                 135
```

```
gga cca gga gag aag tat gag ctc cat gca ggg act gag tcc acc cca        663
Gly Pro Gly Glu Lys Tyr Glu Leu His Ala Gly Thr Glu Ser Thr Pro
        140                 145                 150 agt gtc gtc gtg cac gtg tgc gac agt gac ata gag gaa gaa gag gac        711
Ser Val Val Val His Val Cys Asp Ser Asp Ile Glu Glu Glu Glu Asp
155                 160                 165 cca aag act tcc cca aag cca aaa atc atc caa act cgg cgt cct ggc        759
Pro Lys Thr Ser Pro Lys Pro Lys Ile Ile Gln Thr Arg Arg Pro Gly
170                 175                 180                 185 ctg cca ccc tcc gtg tcc aac tgagctgcct gctccttctc gataatagcc           810
Leu Pro Pro Ser Val Ser Asn
                190 gtctcctctt tatcatgctt tttccccctg ttgtttgtca aaaaaaattg cctttaaatt       870 cctgggtgtt tggttgtttg agattccttc cttgttatca agcctctcgg acaaaagggc      930 taggaaaagg tgatatgtct cctgatcata tcatacccat taagtataac ccattattta     990 gaaggttcta gggaaaaaag tagtattttc ttattaaaca atcagcacag cctatatctt     1050 tgttctctca tgttgatcca agccagagac atcggtaaca aatagcacct gtgttgtttg     1110 tgaggtgttt cagtcccagt cctgatgtgt gtgcgttgtt ctctcctggc acttaaata      1170 ggaccatatg taaacttgac tttgactgca tgagatatcc ctatctggtc tcactcagtc     1230 ctctgcatcc caacattccc aggacatgca tgatcaccag catttatttt cattatttga     1290 ggatatctta taactcacag attgtcagca tccagccatg tcctatctag attaggaaaa     1350 tgatcagaat attccagctc aacaagtctg ggtatactca ctattgtgag tcaatacacc     1410 atagctctgt tgaaattcct ggaggcaaaa ttgaccttgg ccccaaagat attcctcaat     1470 agatttcaaa caccactccc ctgtagaact ctcccagcct cgttggggag gcttgtccag     1530 ggtgatagag actgatttca gacaaaccta tttattacaa aagtttcatg gtgtctgaat     1590 gattgttttc tctcttttgta tatttgtaca aatgtttcag ctgtgctttt aaaaaatctg     1650 gatgtttttt atttagtgat tgttcgacaa ttagctgctt caaaacataa tgtgcattgc     1710 ttatgaatgc cttcatatac taatacagat actctgataa tattcactc taataaggat      1770 aatgctgaat tttgaaagga cacaaaacat ctaatgccaa tatatacatg gttagccaac    1830 atctttgcta tcaagaccac ttgttttaaa taaagatgca agtgtcagtt gtagattatt     1890 gggatgaagc taaatcccca gaatgcagca gcagctgagc atgttaaaat ggggaaggat     1950 gatagctaca tgtatgccgg tcctactcac gcgacacccg tgtgctcaaa aaagttactt     2010 gttttttgtta cgtgtgattt tcctatttct ctagcccaaa gtgcattaca aagatacac     2070 ctatagaacc attaccttct gctatgtgtg ccagggctca tctactcctg tacattaatg     2130 gattacttta tgatgcaaatg cagattacaa tggagtgggg aagtactttc attacccaag    2190 cctcagaaaa acacacaaga acaataacac agcaaacaga ttgagggatt gttgtggttt     2250 ttgactaagg tgtatgttag tttcatcaga aacttaaaac atagactgat cactcagaaa     2310 ttaaagtccg ttttactgtg aatatagcaa tatagtactg gacacagtac tggtgaaact     2370 gaggagagca ttgcttgtaa atcctgagt ttccataagg aaaatgaaaa ctcctttaa       2430 aaataaaatc tgaggagtgt acaataagca tatgctttga cttttccttg ctgtggaggt     2490 ttttggtttt tcattgatga taaacgacta cagacttagt agtggagaaa tggtgtcctc     2550 tagtggaaga aatagtagct ccgctattca gatgcagagc actgcagcat ccagcctttc     2610 aaagctgact cttctcaatc atctgtgggt catttgactt gatttttaa gctaccctga     2670 atttccagaa tgcaggttct aaagaaatct agatgagaga aagtatttga aaatgatttt    2730
```

```
taaatgtttt ttaaaagaca catctgacat ttttaacaac ttagtaaaag ttgaaatgac    2790
cattctgtgt agtcataaaa gaaacacaat gaagtgtatg gcctctggag ttagtcttag    2850
taaaacttat tgctctgtgt caatgttaac ctgtctcaga tcaagtaatt ccttcactag    2910
gttgggtttg gggagggggg aaaagagggg cttttcctag gagaacgata agaaatggaa    2970
agactccttg aagtgttgca agggaacctc ctagcactgt gaaagtcaga atcgcctcag    3030
catttccatg acgcacatta tgcaaatctc tttagcacta ttttaaggtt gaaaacttta    3090
acaatgaagg ggaagggaa gatttccacc aactgaatca tttgtgcacg tgtatagctc    3150
aaagagctta gacttcaaat atatctggtg aatg                               3184
```

<210> SEQ ID NO 18
<211> LENGTH: 192
<212> TYPE: PRT
<213> ORGANISM: Homo sapiens

<400> SEQUENCE: 18

```
Met Asp Cys Asp Val Ser Thr Leu Val Ala Cys Val Val Asp Val Glu
 1               5                  10                  15

Val Phe Thr Asn Gln Glu Val Lys Glu Lys Phe Gly Gly Leu Phe Arg
                20                  25                  30

Thr Tyr Asp Asp Cys Val Thr Phe Gln Leu Phe Lys Ser Phe Arg Arg
            35                  40                  45

Val Arg Ile Asn Phe Ser Asn Pro Lys Ser Ala Ala Arg Ala Arg Ile
        50                  55                  60

Glu Leu His Glu Thr Gln Phe Arg Gly Lys Lys Leu Lys Leu Tyr Phe
 65                  70                  75                  80

Ala Gln Val Gln Thr Pro Glu Thr Asp Gly Asp Lys Leu His Leu Ala
                85                  90                  95

Pro Pro Gln Pro Ala Lys Gln Phe Leu Ile Ser Pro Pro Ser Ser Pro
            100                 105                 110

Pro Val Ser Trp Gln Pro Ile Asn Asp Ala Thr Pro Val Leu Asn Tyr
        115                 120                 125

Asp Leu Leu Tyr Ala Val Ala Lys Leu Gly Pro Gly Glu Lys Tyr Glu
    130                 135                 140

Leu His Ala Gly Thr Glu Ser Thr Pro Ser Val Val His Val Cys
145                 150                 155                 160

Asp Ser Asp Ile Glu Glu Glu Asp Pro Lys Thr Ser Pro Lys Pro
                165                 170                 175

Lys Ile Ile Gln Thr Arg Arg Pro Gly Leu Pro Pro Ser Val Ser Asn
            180                 185                 190
```

<210> SEQ ID NO 19
<211> LENGTH: 192
<212> TYPE: PRT
<213> ORGANISM: Homo sapiens

<400> SEQUENCE: 19

```
Met Asp Cys Asp Val Ser Thr Leu Val Ala Cys Val Val Asp Val Glu
 1               5                  10                  15

Val Phe Thr Asn Gln Glu Val Lys Glu Lys Phe Gly Gly Leu Phe Arg
                20                  25                  30

Thr Tyr Asp Asp Cys Val Thr Phe Gln Leu Phe Lys Ser Phe Arg Arg
            35                  40                  45

Val Arg Ile Asn Phe Ser Asn Pro Lys Ser Ala Ala Arg Ala Arg Ile
```

```
              50                  55                  60
Glu Leu His Glu Thr Gln Phe Arg Gly Lys Lys Leu Lys Leu Tyr Phe
 65                  70                  75                  80

Ala Gln Val Gln Thr Pro Glu Thr Asp Gly Asp Lys Leu His Leu Ala
                 85                  90                  95

Pro Pro Gln Pro Ala Lys Gln Phe Leu Ile Ser Pro Ser Ser Pro
            100                 105                 110

Pro Val Ser Trp Gln Pro Ile Asn Asp Ala Thr Pro Val Leu Asn Tyr
            115                 120                 125

Asp Leu Leu Tyr Ala Val Ala Lys Leu Gly Pro Gly Glu Lys Tyr Glu
130                 135                 140

Leu His Ala Gly Thr Glu Ser Thr Pro Ser Val Val His Val Cys
145                 150                 155                 160

Asp Ser Asp Ile Glu Glu Glu Asp Pro Lys Thr Ser Pro Lys Pro
                165                 170                 175

Lys Ile Ile Gln Thr Arg Arg Pro Gly Leu Pro Pro Ser Val Ser Asn
            180                 185                 190

<210> SEQ ID NO 20
<211> LENGTH: 828
<212> TYPE: DNA
<213> ORGANISM: Homo sapiens
<220> FEATURE:
<221> NAME/KEY: CDS
<222> LOCATION: (23)..(745)

<400> SEQUENCE: 20
aaaaggccca ctttggggga ta atg ctg agg gac act atg aaa tct tgg aat      52
                         Met Leu Arg Asp Thr Met Lys Ser Trp Asn
                          1               5                  10 gat agc cag tca gat ctg tgt agc act gac caa gaa gag gaa gaa gag      100
Asp Ser Gln Ser Asp Leu Cys Ser Thr Asp Gln Glu Glu Glu Glu Glu
                15                  20                  25 atg att ttt ggt gaa aat gaa gat gat ttg gat gag atg atg gat tta      148
Met Ile Phe Gly Glu Asn Glu Asp Asp Leu Asp Glu Met Met Asp Leu
         30                  35                  40 agt gat ctg cct acc tca ctt ttt gct tgc agc gtc cat gaa gca gtg      196
Ser Asp Leu Pro Thr Ser Leu Phe Ala Cys Ser Val His Glu Ala Val
     45                  50                  55 ttt gag gca cga gag cag aag gaa aga ttt gaa gca ctc ttc acc atc      244
Phe Glu Ala Arg Glu Gln Lys Glu Arg Phe Glu Ala Leu Phe Thr Ile
 60                  65                  70 tat gat gac cag gtt act ttt cag ctg ttt aaa agc ttt aga aga gtc      292
Tyr Asp Asp Gln Val Thr Phe Gln Leu Phe Lys Ser Phe Arg Arg Val
 75                  80                  85                  90 aga ata aat ttc agc aaa cct gaa gcg gca gca aga gcg cga ata gaa      340
Arg Ile Asn Phe Ser Lys Pro Glu Ala Ala Ala Arg Ala Arg Ile Glu
                 95                 100                 105 ctc cac gaa aca gac ttc aat ggg cag aag cta aag cta tat ttt gca      388
Leu His Glu Thr Asp Phe Asn Gly Gln Lys Leu Lys Leu Tyr Phe Ala
            110                 115                 120 cag gtg cag atg tcc ggc gaa gtg cgg gac aag tcc tat ctc ctg ccg      436
Gln Val Gln Met Ser Gly Glu Val Arg Asp Lys Ser Tyr Leu Leu Pro
        125                 130                 135 ccc cag cct gtc aag cag ttc ctc atc tcc cct cca gcc tct ccc cca      484
Pro Gln Pro Val Lys Gln Phe Leu Ile Ser Pro Pro Ala Ser Pro Pro
    140                 145                 150 gtg ggg tgg aag cag agc gaa gat gcg atg cct gtt ata aat tat gat      532
Val Gly Trp Lys Gln Ser Glu Asp Ala Met Pro Val Ile Asn Tyr Asp
```

```
                155                 160                 165                 170 tta ctc tgt gct gtt tcc aaa ttg gga cca gga gag aaa tat gaa ctt          580
Leu Leu Cys Ala Val Ser Lys Leu Gly Pro Gly Glu Lys Tyr Glu Leu
                    175                 180                 185 cac gcg gga aca gag tcg aca ccc agc gtg gtg gtt cat gtc tgt gaa          628
His Ala Gly Thr Glu Ser Thr Pro Ser Val Val Val His Val Cys Glu
        190                 195                 200 agt gaa act gaa gag gaa gaa gag aca aaa aac ccc aaa cag aaa att          676
Ser Glu Thr Glu Glu Glu Glu Thr Lys Asn Pro Lys Gln Lys Ile
            205                 210                 215 gcc cag aca agg cgc ccc gac cct ccg acc gca gcg ttg aat gag ccc          724
Ala Gln Thr Arg Arg Pro Asp Pro Pro Thr Ala Ala Leu Asn Glu Pro
        220                 225                 230 cag acc ttt gat tgc gcg ctg tgaggccctt ggttgtggtg cgaggcggct             775
Gln Thr Phe Asp Cys Ala Leu
235                 240 gccctggtgg gctctggcca tggcgctctg tgcctgcggc cgatgcgttg ctg               828
```

<210> SEQ ID NO 21
<211> LENGTH: 241
<212> TYPE: PRT
<213> ORGANISM: Homo sapiens

<400> SEQUENCE: 21

```
Met Leu Arg Asp Thr Met Lys Ser Trp Asn Asp Ser Gln Ser Asp Leu
 1               5                  10                  15

Cys Ser Thr Asp Gln Glu Glu Glu Glu Met Ile Phe Gly Glu Asn
            20                  25                  30

Glu Asp Asp Leu Asp Glu Met Met Asp Leu Ser Asp Leu Pro Thr Ser
        35                  40                  45

Leu Phe Ala Cys Ser Val His Glu Ala Val Phe Glu Ala Arg Glu Gln
    50                  55                  60

Lys Glu Arg Phe Glu Ala Leu Phe Thr Ile Tyr Asp Asp Gln Val Thr
65                  70                  75                  80

Phe Gln Leu Phe Lys Ser Phe Arg Arg Val Arg Ile Asn Phe Ser Lys
                85                  90                  95

Pro Glu Ala Ala Ala Arg Ala Arg Ile Glu Leu His Glu Thr Asp Phe
            100                 105                 110

Asn Gly Gln Lys Leu Lys Leu Tyr Phe Ala Gln Val Gln Met Ser Gly
        115                 120                 125

Glu Val Arg Asp Lys Ser Tyr Leu Leu Pro Pro Gln Pro Val Lys Gln
    130                 135                 140

Phe Leu Ile Ser Pro Pro Ala Ser Pro Pro Val Gly Trp Lys Gln Ser
145                 150                 155                 160

Glu Asp Ala Met Pro Val Ile Asn Tyr Asp Leu Leu Cys Ala Val Ser
                165                 170                 175

Lys Leu Gly Pro Gly Glu Lys Tyr Glu Leu His Ala Gly Thr Glu Ser
            180                 185                 190

Thr Pro Ser Val Val Val His Val Cys Glu Ser Glu Thr Glu Glu Glu
        195                 200                 205

Glu Glu Thr Lys Asn Pro Lys Gln Lys Ile Ala Gln Thr Arg Arg Pro
    210                 215                 220

Asp Pro Pro Thr Ala Ala Leu Asn Glu Pro Gln Thr Phe Asp Cys Ala
225                 230                 235                 240

Leu
```

<210> SEQ ID NO 22
<211> LENGTH: 241
<212> TYPE: PRT
<213> ORGANISM: Homo sapiens

<400> SEQUENCE: 22

```
Met Leu Arg Asp Thr Met Lys Ser Trp Asn Asp Ser Gln Ser Asp Leu
 1               5                  10                  15

Cys Ser Thr Asp Gln Glu Glu Glu Glu Met Ile Phe Gly Glu Asn
            20                  25                  30

Glu Asp Asp Leu Asp Glu Met Met Asp Leu Ser Asp Leu Pro Thr Ser
            35                  40                  45

Leu Phe Ala Cys Ser Val His Glu Ala Val Phe Glu Ala Arg Glu Gln
     50                  55                  60

Lys Glu Arg Phe Glu Ala Leu Phe Thr Ile Tyr Asp Asp Gln Val Thr
 65                  70                  75                  80

Phe Gln Leu Phe Lys Ser Phe Arg Arg Val Arg Ile Asn Phe Ser Lys
                 85                  90                  95

Pro Glu Ala Ala Ala Arg Ala Arg Ile Glu Leu His Glu Thr Asp Phe
            100                 105                 110

Asn Gly Gln Lys Leu Lys Leu Tyr Phe Ala Gln Val Gln Met Ser Gly
        115                 120                 125

Glu Val Arg Asp Lys Ser Tyr Leu Leu Pro Pro Gln Pro Val Lys Gln
    130                 135                 140

Phe Leu Ile Ser Pro Pro Ala Ser Pro Pro Val Gly Trp Lys Gln Ser
145                 150                 155                 160

Glu Asp Ala Met Pro Val Ile Asn Tyr Asp Leu Leu Cys Ala Val Ser
                165                 170                 175

Lys Leu Gly Pro Gly Glu Lys Tyr Glu Leu His Ala Gly Thr Glu Ser
            180                 185                 190

Thr Pro Ser Val Val His Val Cys Glu Ser Glu Thr Glu Glu
        195                 200                 205

Glu Glu Thr Lys Asn Pro Lys Gln Lys Ile Ala Gln Thr Arg Arg Pro
    210                 215                 220

Asp Pro Pro Thr Ala Ala Leu Asn Glu Pro Gln Thr Phe Asp Cys Ala
225                 230                 235                 240

Leu
```

<210> SEQ ID NO 23
<211> LENGTH: 720
<212> TYPE: DNA
<213> ORGANISM: Homo sapiens
<220> FEATURE:
<221> NAME/KEY: CDS
<222> LOCATION: (2)..(637)

<400> SEQUENCE: 23

```
t gac caa gaa gag gaa gaa gag atg att ttt ggt gaa aat gaa gat gat      49
  Asp Gln Glu Glu Glu Glu Glu Met Ile Phe Gly Glu Asn Glu Asp Asp
   1               5                  10                  15 ttg gat gag atg atg gat tta agt gat ctg cct acc tca ctt ttt gct      97
Leu Asp Glu Met Met Asp Leu Ser Asp Leu Pro Thr Ser Leu Phe Ala
                 20                  25                  30 tgc agc gtc cat gaa gca gtg ttt gag gca cga gag cag aag gaa aga     145
Cys Ser Val His Glu Ala Val Phe Glu Ala Arg Glu Gln Lys Glu Arg
             35                  40                  45 ttt gaa gca ctc ttc acc atc tat gat gac cag gtt act ttt cag ctg     193
```

```
Phe Glu Ala Leu Phe Thr Ile Tyr Asp Asp Gln Val Thr Phe Gln Leu
         50                  55                  60 ttt aaa agc ttt aga aga gtc aga ata aat ttc agc aaa cct gaa gcg        241
Phe Lys Ser Phe Arg Arg Val Arg Ile Asn Phe Ser Lys Pro Glu Ala
 65                  70                  75                  80 gca gca aga gcg cga ata gaa ctc cac gaa aca gac ttc aat ggg cag        289
Ala Ala Arg Ala Arg Ile Glu Leu His Glu Thr Asp Phe Asn Gly Gln
                 85                  90                  95 aag cta aag cta tat ttt gca cag tcc tat ctc ctg ccg ccc cag cct        337
Lys Leu Lys Leu Tyr Phe Ala Gln Ser Tyr Leu Leu Pro Pro Gln Pro
            100                 105                 110 gtc aag cag ttc ctc atc tcc cct cca gcc tct ccc cca gtg ggg tgg        385
Val Lys Gln Phe Leu Ile Ser Pro Pro Ala Ser Pro Pro Val Gly Trp
        115                 120                 125 aag cag agc gaa gat gcg atg cct gtt ata aat tat gat tta ctc tgt        433
Lys Gln Ser Glu Asp Ala Met Pro Val Ile Asn Tyr Asp Leu Leu Cys
130                 135                 140 gct gtt tcc aaa ttg gga cca gga gag aaa tat gaa ctt cac gcg gga        481
Ala Val Ser Lys Leu Gly Pro Gly Glu Lys Tyr Glu Leu His Ala Gly
145                 150                 155                 160 aca gag tcg aca ccc agc gtg gtg gtt cat gtc tgt gaa agt gaa act        529
Thr Glu Ser Thr Pro Ser Val Val Val His Val Cys Glu Ser Glu Thr
                165                 170                 175 gaa gag gaa gaa gag aca aaa aac ccc aaa cag aaa att gcc cag aca        577
Glu Glu Glu Glu Glu Thr Lys Asn Pro Lys Gln Lys Ile Ala Gln Thr
            180                 185                 190 agg cgc ccc gac cct ccg acc gca gcg ttg aat gag ccc cag acc ttt        625
Arg Arg Pro Asp Pro Pro Thr Ala Ala Leu Asn Glu Pro Gln Thr Phe
        195                 200                 205 gat tgc gcg ctg tgaggcccttt ggttgtggtg cgaggcggct gccctggtgg           677
Asp Cys Ala Leu
            210 gctctggcca tggcgctctg tgcctgcggc cgatgcgttg ctg                        720

<210> SEQ ID NO 24
<211> LENGTH: 212
<212> TYPE: PRT
<213> ORGANISM: Homo sapiens

<400> SEQUENCE: 24

Asp Gln Glu Glu Glu Glu Met Ile Phe Gly Glu Asn Glu Asp Asp
 1               5                  10                  15

Leu Asp Glu Met Met Asp Leu Ser Asp Leu Pro Thr Ser Leu Phe Ala
             20                  25                  30

Cys Ser Val His Glu Ala Val Phe Glu Ala Arg Glu Gln Lys Glu Arg
         35                  40                  45

Phe Glu Ala Leu Phe Thr Ile Tyr Asp Asp Gln Val Thr Phe Gln Leu
     50                  55                  60

Phe Lys Ser Phe Arg Arg Val Arg Ile Asn Phe Ser Lys Pro Glu Ala
 65                  70                  75                  80

Ala Ala Arg Ala Arg Ile Glu Leu His Glu Thr Asp Phe Asn Gly Gln
                 85                  90                  95

Lys Leu Lys Leu Tyr Phe Ala Gln Ser Tyr Leu Leu Pro Pro Gln Pro
            100                 105                 110

Val Lys Gln Phe Leu Ile Ser Pro Pro Ala Ser Pro Pro Val Gly Trp
        115                 120                 125

Lys Gln Ser Glu Asp Ala Met Pro Val Ile Asn Tyr Asp Leu Leu Cys
130                 135                 140
```

Ala Val Ser Lys Leu Gly Pro Gly Glu Lys Tyr Glu Leu His Ala Gly
145                 150                 155                 160

Thr Glu Ser Thr Pro Ser Val Val His Val Cys Glu Ser Glu Thr
                165                 170                 175

Glu Glu Glu Glu Glu Thr Lys Asn Pro Lys Gln Lys Ile Ala Gln Thr
                180                 185                 190

Arg Arg Pro Asp Pro Pro Thr Ala Ala Leu Asn Glu Pro Gln Thr Phe
                195                 200                 205

Asp Cys Ala Leu
        210

<210> SEQ ID NO 25
<211> LENGTH: 212
<212> TYPE: PRT
<213> ORGANISM: Homo sapiens

<400> SEQUENCE: 25

Asp Gln Glu Glu Glu Glu Met Ile Phe Gly Glu Asn Glu Asp Asp
 1               5                  10                  15

Leu Asp Glu Met Met Asp Leu Ser Asp Leu Pro Thr Ser Leu Phe Ala
                 20                 25                  30

Cys Ser Val His Glu Ala Val Phe Glu Ala Arg Glu Gln Lys Glu Arg
             35                  40                  45

Phe Glu Ala Leu Phe Thr Ile Tyr Asp Asp Gln Val Thr Phe Gln Leu
         50                  55                  60

Phe Lys Ser Phe Arg Arg Val Arg Ile Asn Phe Ser Lys Pro Glu Ala
 65                 70                  75                  80

Ala Ala Arg Ala Arg Ile Glu Leu His Glu Thr Asp Phe Asn Gly Gln
                85                  90                  95

Lys Leu Lys Leu Tyr Phe Ala Gln Ser Tyr Leu Leu Pro Pro Gln Pro
                100                 105                 110

Val Lys Gln Phe Leu Ile Ser Pro Pro Ala Ser Pro Pro Val Gly Trp
                115                 120                 125

Lys Gln Ser Glu Asp Ala Met Pro Val Ile Asn Tyr Asp Leu Leu Cys
130                 135                 140

Ala Val Ser Lys Leu Gly Pro Gly Glu Lys Tyr Glu Leu His Ala Gly
145                 150                 155                 160

Thr Glu Ser Thr Pro Ser Val Val His Val Cys Glu Ser Glu Thr
                165                 170                 175

Glu Glu Glu Glu Glu Thr Lys Asn Pro Lys Gln Lys Ile Ala Gln Thr
                180                 185                 190

Arg Arg Pro Asp Pro Pro Thr Ala Ala Leu Asn Glu Pro Gln Thr Phe
                195                 200                 205

Asp Cys Ala Leu
        210

<210> SEQ ID NO 26
<211> LENGTH: 1039
<212> TYPE: DNA
<213> ORGANISM: Homo sapiens

<400> SEQUENCE: 26
ggtgcttata aagcagtaag ggccagcccc cactccctgg ggaaaaaaaa agtgcagctt      60

```
ccacagcatc ctgtttggac agcaaattcc tgagtcaagt cctgcatgct tgcaggcaga      120
cagggacaaa gtgtaagttt ctactggaaa gaggtgacgt caacaccta gtcatttcc       180 ctatgctaat taactttgct tggggagaat ggaaaaaaca gctgaggttt gctccacagc      240
atcctgtttg gacagcaaat tcctgagtca agtcctgcat gcttgcaggc agacagggac     300
aaagtgtaag tttctactgg aaagaggtga cgtcaacacc ttagtcattt ccctatgct      360 aattaacttt gcttggggag aatggaaaaa acagctgagg tttgcttcac agctgcttta     420
tcaacctctc ttgcagcata gtttccactg gtagtaattc cattcagcta ctcagacaac     480
acgctcctcg gccgaatggg acgacccttc ttaagatgga aaatgttaca aaagaaaaag     540
gatgaaggtc tgtggcaata acagcaatt agactagg gaaatttcaa ggctttggga       600
aacctggaaa ccaaagtccg ggtgacatac ttgatccctg gaatttcctg aaaacctcaa     660
tcaaagtttc actttggggt attagagaaa catttgaa atctgtcttg gtcaataaaa        720
attttaaagg acaaaagag gaatcatttt gaagtgtagt taaaattttt tccccagtg       780 acatttatt ggatgaatgt cccaatttct acttgtatcc cacagtggaa tggagcaaac      840
agaacctaaa acaatcctag gattttcatt tgaaaacttc attattataa tttgagaact     900
ggggatatga aacacttcga tcattttcaa agcactactg aattcaggca aaggatacaa     960
aaacactagc cttgaaact gagcaatcta gcctttgaaa ctgagcaaag aagcattaac     1020 ccattatgc cagaggttg                                                   1039

<210> SEQ ID NO 27
<211> LENGTH: 853
<212> TYPE: DNA
<213> ORGANISM: Homo sapiens

<400> SEQUENCE: 27
caacctctgg cataaatggg ttaatgcttc tttgtccttt gcctgaattc agtagtgctt       60
tgaaaatgat cgaagtgttt catatcccca gttctcaaat tataataatg aagttttcaa     120
atgaaaatcc taggattgtt ttaggttctg tttgctccat tccactgtgg gatacaagta     180
gaaattggga cattcatcca ataaaatgtc actgggaaa aaattttaa ctacacttca      240 aaatgattcc tctttttgtc ctttaaaatt tttattgacc aagacagatt tcaaaatgtt     300
ttctctaata ccccaaagtg aaactttgat tgaggttttc aggaaattcc agggatcaag     360
tatgtcaccc ggactttggt ttccaggttt cccaaagtct tgaaatttcc ctacagtcta     420
attgctgttt attgccacag accttcatcc tttttctttt gtaacatttt ccatcttaag     480
aagggtcgtc ccattcggcc gaggagcgtg ttgtctgagt agctgaatgg aattactacg     540
agtggaaact atgctgcaag agaggttgat aaagcagctg tgaagcaaac ctcagctgtt     600
ttttccattc tccccaagca agttaatta gcatagggaa aatgactaag gtgttgacgt      660
cacctctttc cagtagaaac ttacactttg tccctgtcta cctgcaagca tgcaggactt     720
gactcaggaa tttgctgtcc aaacaggatg ctgtggaagc tgcactttt ttttccccag      780 ggagtggggg ctggccctta ctgctttata agcaccagct caagaaggaa cctacagcct     840
cttggaaagg aat                                                        853
```